(12) United States Patent
Hyde et al.

(10) Patent No.: US 8,285,367 B2
(45) Date of Patent: *Oct. 9, 2012

(54) VASCULATURE AND LYMPHATIC SYSTEM IMAGING AND ABLATION ASSOCIATED WITH A RESERVOIR

(75) Inventors: Roderick A. Hyde, Redmond, WA (US); Edward K. Y. Jung, Bellevue, WA (US); Nathan P. Myhrvold, Medina, WA (US); Clarence T. Tegreene, Bellevue, WA (US); Willard H. Wattenburg, Walnut Creek, CA (US); Lowell L. Wood, Jr., Bellevue, WA (US); Richard N. Zare, Stanford, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 505 days.

This patent is subject to a terminal disclaimer.

(21) Appl. No.: 11/973,367

(22) Filed: Oct. 5, 2007

(65) Prior Publication Data

US 2009/0093728 A1    Apr. 9, 2009

(51) Int. Cl.
*A61B 6/00* (2006.01)

(52) U.S. Cl. ...................................................... 600/476

(58) Field of Classification Search ............... 604/6.15, 604/8, 20, 27, 28, 40, 65, 328, 408, 93.01; 600/407

See application file for complete search history.

(56) References Cited

U.S. PATENT DOCUMENTS

| | | |
|---|---|---|
| 4,718,417 A | 1/1988 | Kittrell et al. |
| 4,955,857 A | 9/1990 | Shettigar |
| 5,092,886 A | 3/1992 | Dobos-Hardy |
| 5,107,422 A | 4/1992 | Kamentsky et al. |
| 5,281,199 A * | 1/1994 | Ensminger et al. ...... 604/288.03 |
| 5,338,625 A | 8/1994 | Bates et al. |
| 5,474,772 A | 12/1995 | Maddock |
| 5,594,544 A | 1/1997 | Horiuchi et al. |
| 5,681,260 A | 10/1997 | Ueda et al. |
| 5,702,432 A | 12/1997 | Chen et al. |
| 5,705,293 A | 1/1998 | Hobson |

(Continued)

FOREIGN PATENT DOCUMENTS

EP    1 550 454 A1    7/2005

(Continued)

OTHER PUBLICATIONS

PCT International Search Report; International App. No. PCT/US2008/011419; Dec. 16, 2008; pp. 1-3.

(Continued)

*Primary Examiner* — Jacqueline Cheng
(74) *Attorney, Agent, or Firm* — Workman Nydegger

(57) ABSTRACT

In an embodiment, a system includes one or one or more reservoirs responsive to control circuitry for receiving target(s) associated with one or more blood or lymph vessel of a subject. The system includes one or more first energy source associated with the one or more reservoirs for providing energy to elicit image response(s) associated with the target(s). The system includes one or more sensors associated with the one or more reservoirs for capturing the image response(s). Control circuitry is provided and coupled to the sensors for at least partially identifying the target(s) based at least partially on the captured image response(s) during an expected transit time of the target(s) through a detection area. Attachment unit(s) responsive to the control circuitry are provided for attaching the one or more reservoirs to the blood or lymph vessel.

11 Claims, 24 Drawing Sheets

U.S. PATENT DOCUMENTS

| | | | |
|---|---|---|---|
| 5,735,276 | A | 4/1998 | Lemelson |
| 5,790,691 | A | 8/1998 | Narayanswamy et al. |
| 5,934,278 | A | 8/1999 | Ishihara et al. |
| 6,030,653 | A | 2/2000 | Rosenthal |
| 6,106,477 | A | 8/2000 | Miesel et al. |
| 6,162,242 | A | 12/2000 | Peyman |
| 6,190,691 | B1 | 2/2001 | Mak |
| 6,240,312 | B1 | 5/2001 | Alfano et al. |
| 6,287,516 | B1 | 9/2001 | Matson et al. |
| 6,379,920 | B1 | 4/2002 | El-Sayed et al. |
| 6,409,719 | B1 | 6/2002 | Manning |
| 6,425,867 | B1 | 7/2002 | Vaezy et al. |
| 6,471,872 | B2 | 10/2002 | Kitaevich et al. |
| 6,733,471 | B1 | 5/2004 | Ericson et al. |
| 6,802,811 | B1 | 10/2004 | Slepian |
| 6,849,183 | B2 | 2/2005 | Gorsuch et al. |
| 6,881,584 | B1 | 4/2005 | Lenhard et al. |
| 6,939,290 | B2 | 9/2005 | Iddan |
| 6,956,961 | B2 | 10/2005 | Cong et al. |
| 7,151,847 | B2 | 12/2006 | Vaisberg et al. |
| 7,175,637 | B2 | 2/2007 | Vargas et al. |
| 7,244,232 | B2* | 7/2007 | Connelly et al. ............ 600/309 |
| 7,264,794 | B2 | 9/2007 | Georgakoudi et al. |
| 7,892,766 | B2 | 2/2011 | King et al. |
| 8,000,784 | B2* | 8/2011 | Ferren et al. ................. 607/2 |
| 2001/0051766 | A1 | 12/2001 | Gazdzinski |
| 2002/0034757 | A1 | 3/2002 | Cubicciotti |
| 2002/0049544 | A1 | 4/2002 | Nislow et al. |
| 2002/0064809 | A1 | 5/2002 | Mutz et al. |
| 2002/0090388 | A1* | 7/2002 | Humes et al. ................. 424/422 |
| 2003/0149090 | A1 | 8/2003 | Gehlsen et al. |
| 2003/0152823 | A1 | 8/2003 | Heller |
| 2003/0195415 | A1 | 10/2003 | Iddan |
| 2003/0214579 | A1 | 11/2003 | Iddan |
| 2003/0231981 | A1 | 12/2003 | Johnson et al. |
| 2004/0059280 | A1 | 3/2004 | Makower et al. |
| 2004/0191246 | A1 | 9/2004 | Connelly et al. |
| 2004/0218724 | A1 | 11/2004 | Chornenky et al. |
| 2005/0090732 | A1 | 4/2005 | Ivkov et al. |
| 2005/0121411 | A1 | 6/2005 | Cohen |
| 2005/0126916 | A1 | 6/2005 | Lockard et al. |
| 2005/0192478 | A1 | 9/2005 | Williams et al. |
| 2005/0221529 | A1 | 10/2005 | Bank et al. |
| 2005/0234440 | A1 | 10/2005 | Wood, Jr. |
| 2005/0251347 | A1 | 11/2005 | Perona et al. |
| 2005/0272972 | A1 | 12/2005 | Iddan |
| 2005/0272974 | A1 | 12/2005 | Iddan |
| 2006/0039593 | A1 | 2/2006 | Sammak et al. |
| 2006/0074479 | A1 | 4/2006 | Bailey et al. |
| 2006/0129050 | A1 | 6/2006 | Martinson et al. |
| 2006/0149348 | A1 | 7/2006 | Vogel et al. |
| 2006/0183223 | A1 | 8/2006 | King et al. |
| 2006/0200220 | A1 | 9/2006 | Brown et al. |
| 2006/0247525 | A1 | 11/2006 | Huo et al. |
| 2007/0010868 | A1* | 1/2007 | Ferren et al. ................. 623/1.15 |
| 2007/0038143 | A1 | 2/2007 | Christensen et al. |
| 2007/0066929 | A1 | 3/2007 | Ferren |
| 2007/0073135 | A1 | 3/2007 | Lee et al. |
| 2007/0073151 | A1 | 3/2007 | Lee |
| 2007/0077052 | A1 | 4/2007 | Chang |
| 2007/0093739 | A1 | 4/2007 | Brady et al. |
| 2007/0156048 | A1 | 7/2007 | Panescu et al. |
| 2007/0156211 | A1* | 7/2007 | Ferren et al. ................. 607/101 |
| 2007/0178084 | A1 | 8/2007 | King et al. |
| 2007/0179380 | A1 | 8/2007 | Grossman |
| 2007/0179552 | A1 | 8/2007 | Dennis et al. |
| 2007/0225633 | A1 | 9/2007 | Ferren et al. |
| 2007/0225634 | A1 | 9/2007 | Ferren et al. |
| 2007/0276208 | A1 | 11/2007 | Connelly et al. |
| 2007/0282190 | A1 | 12/2007 | Dekel et al. |
| 2007/0299384 | A1 | 12/2007 | Faul et al. |
| 2008/0275376 | A1 | 11/2008 | Howell et al. |
| 2009/0022768 | A1 | 1/2009 | King et al. |
| 2009/0054908 | A1 | 2/2009 | Zand et al. |
| 2010/0167372 | A1 | 7/2010 | King et al. |
| 2010/0185134 | A1 | 7/2010 | Houwen et al. |

FOREIGN PATENT DOCUMENTS

| | | |
|---|---|---|
| WO | WO 02/47032 A1 | 6/2002 |
| WO | WO 03/021967 A2 | 3/2003 |
| WO | WO 03/106966 A2 | 12/2003 |

OTHER PUBLICATIONS

U.S. Appl. No. 11/414,164, Jung et al.

"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html.

Ammor, Mohammed Salim; "Short Communication: Recent Advances in the Use of Intrinsic Fluorescence for Bacterial Identification and Characterization"; Journal of Fluorescence; bearing a dates of Dec. 20, 2006 and Mar. 12, 2007; pp. 1-5; Springer.

Anderson, John G. et al.; "Inactivation of Food-Borne Enteropathogenic Bacteria and Spoilage Fungi Using Pulsed-Light"; IEEE Transactions on Plasma Science; bearing a date of Feb. 2000; pp. 83-88; vol. 28, No. 1; IEEE.

Arndt, Dickey et al.; "Microwave Radiation-Therapeutic Application for Cure of Subcutaneous Bacterial Infections"; Space Life Sciences; pp. 1-2; located at: http://research.jsc.nasa.gov/PDF/SLiSci-7.pdf.

Baddour, R.E. et al.; "High Frequency Ultrasound Imaging of Changes in Cell Structure Including Apoptosis"; IEEE—Ultrasonic Symposium; bearing a date of 2002; pp. 1639-1644; vol. 2, No. 8-11; located at: http://ieeexplore.ieee.org/xpls/abs_all.jsp?tp=&arnumber=1192609&isnumber=26742.

Bartels, Kenneth E. et al.; "Use of Diode Laser Energy (808 nm) for Selective Photothermolysis of Contaminated Wounds"; SPIE; bearing a date of May 1995; pp. 602-606; vol. 2395; SPIE.

Bekassy, Zoltan; "Long-Term Follow-Up of Cervical Intraepithelial Neoplasia Treated With Minimal Conization by Carbon Dioxide Laser"; Lasers in Surgery and Medicine; bearing a date of 1997; pp. 461-466; vol. 20; Wiley-Liss, Inc.

Bezrouk, A.; Hanuš, J.; Záhora, J.; "Temperature Characteristics of Nitinol Spiral Stents"; Scripta Medica (BRNO); bearing a date of Oct. 2005; pp. 219-226; vol. 78, No. 4.

Bins, M. et al.; "Texture of White Blood Cells Expressed by the Counting Densitogram"; Cytometry; bearing a date of 1981; pp. 321-324; vol. 1, No. 5; Society for Analytical Cytology.

Bouchard, Alain et al.; "Optical Characterization of Pseudomonas Fluorescens on Meat Surfaces Using Time-Resolved Fluorescence"; Journal of Biomedical Optics; bearing a date of Jan./Feb. 2006; pp. 014011, 1-7; vol. 11, No. 1.

Bronk, Burt V.; "Measuring Diameters of Rod-Shaped Bacteria in Vivo with Polarized Light Scattering"; Biophysical Journal; bearing a date of Sep. 1995; pp. 1170-1177; vol. 69; Biophysical Society.

Burr, Jennifer et al.; "Interventional Technologies for Tissue Volume Reduction: A Primer"; Review Body for Interventional Procedures; bearing a date of Oct. 2004; pp. 1-10 plus i-ii.

Chan, You et al.; "Original Article: Bactericidal Effects of Different Laser Wavelengths on Periodontopathic Germs in Photodynamic Therapy"; Lasers in Medicine and Science; bearing a date of 2003; pp. 51-55; vol. 18; Springer-Verlag.

Chang, Leland et al.; "Extremely Scaled Silicon Nano-CMOS Devices"; Proceedings of the IEEE; bearing a date of Nov. 2003; pp. 1860-1873; vol. 91, No. 11; IEEE.

Chen, Haitao et al.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois.

Chen, Ting; Barton, Scott Calabrese, Binyamin, Gary; Gao, Zhiqiang; Zhang, Yongchao, Kim, Hyug-Han; Heller, Adam; "A Miniature Biofuel Cell"; Journal of the American Chemical Society; Aug. 11, 2001; pp. 8630-8631; vol. 123; 2001 American Chemical Society.

Chiou, Pei Yu et al.; "Letters: Massively Parallel Manipulation of Sigle Cells and Microparticles Using Optical Images"; Nature; bearing a date of Jul. 2005; pp. 370-372; vol. 436; Nature Publishing Group.

Choi, Wonshik et al.; "Brief Communications: Tomographic Phase Microscopy"; Nature Methods: Advanced Online Publication; bearing a date of Aug. 12, 2007; pp. 1-3; Nature Publishing Group; located at: http://www.nature.com/naturemethods.

Clavero, M. Rocelle S. et al.; "Inactivation of *Escherichia coli* O157:H7, Salmonellae, and Campylobacter Jejuni in Raw Ground Beef by Gamma Irradiation"; Applied and Environmental Microbiology; bearing a date of Jun. 1994; pp. 2069-2075; vol. 60, No. 6; American Society for Microbiology.

Colley, C.S. et al.; "Spectroscopic Imaging of Arteries and Atherosclerotic Plaques"; Biopolymers; bearing a date of Jul. 2004; pp. 328-335; vol. 74, No. 4; Wiley Periodicals, Inc.

Conrad, Christian et al.; "Automatic Identification of Subcellular Phenotypes on Human Cell Arrays"; Genome Research; bearing a date of 2004; pp. 1130-1136; vol. 14; Cold Spring Harbor Laboratory Press; located at: http://www.genome.org/cgi/content/abstract/14/6/1130.

Cowman, Alan F. et al.; "A P-glycoprotein Homologue of Plasmodium Falciparum Is Localized on the Digestive Vacuole"; The Journal of Cell Biology; bearing a date of Jun. 1991; pp. 1033-1042; vol. 113, No. 5; The Rockefeller University Press; located at: www.jcb.org.

Cristofanilli, Massimo et al.; "Original Article: Circulating Tumor Cells, Disease Progression, and Survival in Metastatic Breast Cancer"; The New England Journal of Medicine; bearing a date of Aug. 19, 2004; pp. 781-791; vol. 351, No. 8; Massachusetts Medical Society; located at: www.nejm.org.

Dempster, A.G.; "Using Granulometries in Processing Images of Malarial Blood"; Circuits and Systems ISCAS IEEE International Symposium; bearing a date of 2001; pp. 291-294; vol. 5; located at: http://ieeexplore.ieee.org/xpls/abs_all.jsp?arnumber=922042.

De Simone, Noelle A. et al.; "Research Report: Bactericidal Effect of 0.95-mW Helium-Neon and 5-mW Indium-Gallium-Aluminum-Phosphate Laser Irradiation at Exposure Times of 30, 60, and 120 Seconds on Photosensitized *Staphylococcus aureus* and *Pseudomonas aeruginosa* In Vitro"; Physical Therapy; bearing a date of Sep. 1999; pp. 839-846; vol. 79, No. 9.

Dharmadhikari, J.A. et al.; "Torque-Generating Malaria-Infected Red Blood Cells in an Optical Trap"; Optics Express; bearing a date of Mar. 22, 2004; pp. 1179-1184; vol. 12, No. 6; OSA.

Diegelmann, R.F.; "Collection of Leukocytes, Fibroblasts, and Collagen Within an Implantable Reservoir Tube During Tissue Repair"; Journal of Leukocyte Biology; bearing a date of 1987; pp. 667-672; vol. 42; Alan R. Liss, Inc.

Doornbos, R.M.P. et al.; "White Blood Cell Differentiation Using a Solid State Flow Cytometer"; Cytometry; bearing a date of 1993; pp. 589-594; vol. 14; Wiley-Liss, Inc.

Emery, Yves et al.; "DHM (Digital Holography Microscope) for Imaging Cells"; Journal of Physics: Conference Series: International Conference on Nanoscience and Technology; bearing a date of 2007; pp. 1317-1321; vol. 61; IOP Publishing Ltd.

Evans, Conor L. et al.; "Chemical Imaging of Tissue in Vivo with Video-Rate Coherent Anti-Stokes Raman Scattering Microscopy"; PNAS; bearing a date of Nov. 15, 2005; pp. 16807-16812; vol. 102, No. 46; The National Academy of Science of the USA.

Fei-Fei, Li et al.; "One-Shot Learning of Object Categories"; IEEE Transactions on Pattern Analysis and Machine Intelligence; bearing a date of Apr. 2006; pp. 594-611; vol. 28, No. 4; IEEE.

Feldman, Yuri et al.; "Time Domain Dielectric Spectroscopy Study of Biological Systems"; IEEE; bearing a date of 2003; pp. 728-753; IEEE.

Fernandez, Daniel C.; "Letters: Infrared Spectroscopic Imaging for Histopathologic Recognition"; Nature Biotechnology; bearing a date of Apr. 2005; pp. 469-474; vol. 23, No. 4; Nature Publishing Group; located at: http://www.nature.com/naturebiotechnology.

Galanzha, Ekaterina I. et al.; "Topic Highlight: Advances in Small Animal Mesentery Models for In Vivo Flow Cytometry, Dynamic Microscopy, and Drug Screening"; World Journal of Gastroenterology; bearing a date of Jan. 14, 2007; pp. 192-218; vol. 13, No. 2; The WJG Press.

Gao, Yuanfang et al.; "A Micro Sensing Probe for Detecting Individual Biological Cells"; Proceedings of the 25th Annual International Conference of the IEEE EMBS; bearing a date of Sep. 17-21, 2003; pp. 3348-3351; IEEE.

Giana, Hector Enrique et al.; "Rapid Identification of Bacterial Species by Fluorescence Spectroscopy and Classification Through Principal Components Analysis"; Journal of Fluorescence; bearing a date of Nov. 2003; pp. 489-493; vol. 13, No. 6; Plenum Publishing Corporation.

Gibson, S.C. et al.; "Original Article: Ten-Year Experience of Carbon Dioxide Laser Ablation as Treatment for Cutaneous Recurrence of Malignant Melanoma"; British Journal of Surgery; bearing a date of 2004; pp. 893-895; vol. 91; John Wiley & Sons Ltd.

Gourley, Paul L. et al.; "Ultrafast Nanolaser Flow Device for Detecting Cancer in Single Cells"; Biomedical Microdevices; bearing a date of 2005; pp. 331-339; vol. 7, No. 4; Springer Science+Business Media, Inc.

Gourley, Paul L. et al.; "Optical Phenotyping of Human Mitochondria in a Biocavity Laser"; IEEE Journal of Selected Topics in Quantum Electronics; bearing a date of Jul./Aug. 2005; pp. 818-826; vol. 11, No. 4; IEEE.

Graham, Anna R.; "Fungal Autofluorescence with Ultraviolet Illumination"; Brief Scientific Reports: A.J.C.P.; bearing a date of Feb. 1983; pp. 231-234; American Society of Clinical Pathologists.

Green, Christopher F. et al.; "Note/Note: Disinfection of Selected *Aspergillus spp*. Using Ultraviolet Germicidal Irradiation"; Can. J. Microbiol.; bearing a date of 2004; pp. 221-224; vol. 50; NRC Canada.

Gronqvist, Anders et al.; "Bactericidal Effect of Pulsed 1,064 nm Nd:YAG Laser Light on *Staphylococcus epidermidis* is of Photothermal Origin: An In Vitro Study"; Lasers in Surgery and Medicine: bearing a date of 2000; pp. 336-340; vol. 27; Wiley-Liss, Inc.

Grover, S.C. et al.; "Analysis of the Behaviour of Erythrocytes in an Optical Trapping System"; Optics Express; bearing a date of Dec. 18, 2000; pp. 533-539; vol. 7, No. 13; OSA.

Guffey, J. Stephen et al.; "Effects of Combined 405-nm and 880-nm Light on *Staphylococcus aureus* and *Pseudomonas aeruginosa* in Vitro"; Photomedicine and Laser Surgery; bearing a date of 2006; pp. 680-683; vol. 24, No. 6; Mary Ann Liebert, Inc.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hamblin, Michael R. et al.; "Rapid Control of Wound Infections by Targeted Photodynamic Therapy Monitored by In Vivo Bioluminescence Imaging"; Photochemistry and Photobiology; bearing a date of Jan. 2002; pp. 51-57; vol. 75, No. 1; American Society for Photobiology.

Hancock, Patrick et al.; "Megawatt, Pulsed Ultraviolet Photon Sources for Microbial Inactivation"; IEEE Transactions on Plasma Science; bearing a date of Oct. 2004; pp. 2026-2031; vol. 32, No. 5; IEEE.

Hanna, Darrin M.; "Using a System-on-a-Chip Implantable Device to Filter Circulating Infected Cells in Blood or Lymph"; IEEE Transactions on Nanobioscience; bearing a date of Mar. 2003; pp. 6-13; vol. 2, No. 1; IEEE.

Hansen, Gunnar et al.; "Review Article: Transbronchial Laser Ablation of Benign and Malignant Tumors"; Minimally Invasive Therapy; bearing a date of 2006; pp. 4-8; vol. 15, No. 1; Taylor & Francis.

Hauser, Barb; "Blood Tests"; International Waldenstrom's Macroglobulinemia Foundation; bearing a date of 2001; pp. 1-7; located at: http://www.iwmf.com/Blood_Tests.pdf.

He, Wei et al.; "Nucleus Shape Recognition for an Automated Hematology Analyzing System"; Proceedings of the Second Joint EMBS/BMES Conference IEEE; bearing a date of Oct. 23-26, 2002; pp. 1043-1044; IEEE.

He, Yin-Cheng et al.; "Relationship Between Nuclear Morphometry, DNA Content and Resectability of Pancreatic Cancer"; World Journal of Gastroenterology; bearing a date of 2003; pp. 1863-1865; vol. 9, No. 8; The WJG Press.

Helfinstine, Shannon L. et al.; "Inactivation of Bacillus Endospores in Envelopes by Electron Beam Irradiation"; Applied and Environmental Microbiology; bearing a date of Nov. 2005; pp. 7029-7032; vol. 71, No. 11; American Society for Microbiology.

Hilton, Peter J.; "Laser Induced Fluorescence Imaging of Bacteria"; SPIE; bearing a date of 1998; pp. 1174-1178; vol. 3491; SPIE.

Holmes, David; Morgan, Hywel; "Cell Positioning and Sorting Using Dielectrophoresis"; European Cells and Materials; bearing a date of 2002; pp. 120-122; vol. 4, Suppl. 2.

Hoon, Dave S.B.; "Are Circulating Tumor Cells an Independent Prognostic Factor in Patients with High-Risk Melanoma?"; Nature Clinical Practice: Oncology; bearing a date of Dec. 2004; pp. 74-75; vol. 1, No. 2; Nature Publishing Group; located at: www.nature.com/clinicalpractice/onc.

Hwu, Y. et al.; "Imaging Cells and Tissues with Refractive Index Radiology"; Biophysical Journal; bearing a date of Dec. 2004; pp. 4180-4187; vol. 87; Biophysical Society.

Jawhara, Samir et al.; "Original Article: Monitoring of Bactericidal Action of Laser by in Vivo Imaging of Bioluminescent *E. coli* in a Cutaneous Wound Infection"; Lasers Med Sci; bearing a date of 2006; pp. 153-159; vol. 21; Springer-Verlag London.

Jori, Giulio et al.; "Photodynamic Therapy in the Treatment of Microbial Infections: Basic Principles and Perspective Applications"; Lasers in Surgery and Medicine; bearing a date of 2006; pp. 468-481; vol. 38; Wiley-Liss, Inc.

Karrer, S. et al.; "Photodynamic Inactivation of *Staphylococci* with 5-Aminolaevulinic Acid or Photofrin"; Lasers Med Sci; bearing a date of 1999; pp. 54-61; vol. 14; Springer-Verlag London Limited.

Kennedy, J.E. et al.; "Review Article: High Intensity Focused Ultrasound: Surgery of the Future"; The British Journal of Radiology; bearing a date of 2003; pp. 590-599; vol. 76; The British Institute of Radiology.

Kim, Hea-Young et al.; "Homeland Security: Real-Time Detection of Microbial Contamination"; IEEE Engineering in Medicine and Biology Magazine; bearing a date of Jan./Feb. 2004; pp. 122-129; IEEE.

Klima, Uwe et al.; "Magnetic Vascular Port in Minimally Invasive Direct Coronary Artery Bypass Grafting"; Circulation; bearing a date of 2004; pp. II-55-II-60; vol. 110; American Heart Association.

Koenig, K. et al.; "Laser-Induced Autofluorescence for Medical Diagnosis"; Journal of Fluorescence; bearing a date of 1994; pp. 17-40; vol. 4, No. 1; Plenum Publishing Corporation.

Konoplev, Sergej; "Advances in the Pathologic Diagnosis and Biology of Acute Myeloid Leukemia"; Annals of Diagnostic Pathology' bearing a date of 2006; pp. 39-65; vol. 10; Elsevier Inc.; located at: www.sciencedirect.com.

Kovalev, Vassili A. et al.; "Robust Recognition of White Blood Cell Images"; Pattern Recognition: Proceedings of the 13th International Conference IEEE; bearing a date of Aug. 25-29, 1996; pp. 371-375; vol. 4; IEEE.

Laflamme, Christian et al.; "Short Communication: Flow Cytometry Sorting Protocol of Bacillus Spore Using Ultraviolet Laser and Autofluorescence as Main Sorting Criterion"; J. Fluoresc; bearing a date of 2006; pp. 733-737; vol. 16; Springer.

Lally, C. et al.; "Cardiovascular Stent Design and Vessel Stresses: A Finite Element Analysis"; Journal of Biomechanics; bearing a date of 2005; pp. 1574-1581; vol. 38; Elsevier Ltd.; located at: www.elsevier.com/locate/jbiomech or www.JBiomech.com.

"Lasers in Cancer Treatment: Questions and Answers"; National Cancer Institute FactSheet; bearing a date of Aug. 10, 2004; pp. 1-4; vol. 7.8.

Lee, Haeshin et al.; "Letters: A Reversible Wet/Dry Adhesive Inspired by Mussels and Geckos"; Nature; bearing a date of Jul. 19, 2007; pp. 338-341 plus reference page; vol. 448; Nature Publishing Group.

Lee, Shun et al.; "Laser-Generated Stress Waves and Their Effects on the Cell Membrane"; IEEE Journal of Selected Topics in Quantum Electronics; bearing a date of Jul./Aug. 1999; pp. 997-1003; vol. 5, No. 4; IEEE.

Liu, Shimin et al.; "Direct Visualization of Trapped Erythrocytes in Rat Brain After Focal Ischemia and Reperfusion"; Journal of Cerebral Blood Flow & Metabolism; bearing a date of 2002; pp. 1222-1230; vol. 22; Lippincott Williams & Wilkins, Inc.

Liu, Y. et al.; "An Impulse Response Flow Cytometric Technique for Blood Cell Characterisation Instrumentation and Preliminary Evaluation"; Proceedings of the 20th Annual International Conference of the IEEE Engineering in Medicine and Biology Society; bearing a date of 1998; pp. 1881-1884; vol. 20, No. 4; IEEE.

"Low Blood Cell Counts: Side Effect of Cancer Treatment"; MayoClinic.com—Tools for Healthier Lives; bearing a date of Sep. 2005 and printed on Sep. 10, 2007; pp. 1-5; located at: http://www.mayoclinic.com/health/cancer-treatment/CA00066.

"Low White Blood Cell Count (Leukopenia)"; MayhoClinic.omc—Tools for Healthier Lives; bearing a date of Oct. 9, 2006 printed on Sep. 10, 2007; pp. 1-2; located at; http://www.mayoclinic.com/health/low-white-blood-cell-count/AN00726.

Maisch, Tim; "Original Article: Anti-Microbial Photodynamic Therapy: Useful in the Future?"; Lasers Med Sci; bearing a date of 2007; pp. 83-91; vol. 22; Springer-Verlag London Limited.

Martin, David R. et al.; "Learning to Detect Natural Image Boundaries Using Local Brightness, Color, and Texture Cues"; IEEE Transactions on Pattern Analysis and Machine Intelligence; bearing a date of May 2004; pp. 530-549; vol. 26, No. 5; IEEE.

Mateus, Carolina et al.; "Adherence of Candida Albicans to Silicone Induces Immediate Enhanced Tolerance to Fluconazole"; Antimicrobial Agents and Chemotherapy; bearing a date of Sep. 2004; pp. 3358-3366; vol. 48, No. 9; American Society for Microbiology.

Mendelow, Barry V. et al.; "Automated Malaria Detection by Depolarization of Laser Light"; British Journal of Haematology; bearing a date of 1999; pp. 499-503; vol. 104; Blackwell Science Ltd.

Miller, Liron et al.; "Cancer Cells Ablation with Irreversible Electroporation"; Technology in Cancer Research & Treatment; bearing a date of Dec. 2005; pp. 1-7; vol. 4, No. 6; Adenine Press.

Mohamed, Hisham et al.; "Development of a Rare Cell Fractionation Device: Application for Cancer Detection"; IEEE Transactions on Nanobioscience; bearing a date of Dec. 2004; pp. 251-256; vol. 3, No. 4; IEEE.

Mohanty, Swomitra K. et al; "Micro Electrical Impedance Spectroscopy of Bovine Chromaffin Cells"; Microtechnologies in Medicine & Biology 2nd Annual International IEEE-EM Special Topic Conference; bearing a date of 2002; pp. 485-488; IEEE.

Moore, George E. et al.; "The Comparative Size and Structure of Tumor Cells and Clumps in the Blood, Bone Marrow, and Tumor Imprints"; Cancer; bearing dates of 1960 and Jun. 23, 2006; pp. 111-117; vol. 13, No. 1; American Cancer Society; located at http://www3.interscience.wiley.com/cgi-bin/abstract/112663324/ABSTRACT?CRETRY=1&SRETRY=0.

Moore, Lee R. et al.; "Hemoglobin Degradation in Malaria-Infected Erythrocytes Determined from Live Cell Magnetophoresis"; The FASEB Journal; bearing a date of Feb. 6, 2006; pp. 747-749; vol. 20; FASEB.

Nitzan Y. et al.; "Endogenous Porphyrin Production in Bacteria by δ-Aminolaevulinic Acid and Subsequent Bacterial Photoeradication"; Lasers Med Sci; bearing a date of 1999; pp. 269-277; vol. 14; Springer-Verlag London Limited.

Nolan, Derek P. et al; "Characterization of a Novel, Stage-Specific, Invariant Surface Protein in Trypanosoma Brucei Containing an Internal, Serine-Rich, Repetitive Motif"; The Journal of Biological Chemistry; bearing a date of Nov. 14, 1997; pp. 29212-29221; vol. 272, No. 46; The American Society for Biochemistry and Molecular Biology, Inc.

Norberto, L. et al.; "Laser Photoablation of Colorectal Adenomas"; Surgery Endoscopy; bearing a date of 2005; pp. 1045-1048; vol. 19; Springer Science + Business Media, Inc.

Nozaki, Kengo et al.; "Room Temperature Continuous Wave Operation and Controlled Spontaneous Emission in Ultrasmall Photonic Crystal Nanolaser"; Optics Express; bearing a date of Jun. 11, 2007; vol. 15, No. 12; OSA.

Nussbaum, Ethne L. et al.; "Effects of 810 nm Laser Irradiation In Vitro Growth of Bacteria: Comparison of Continuous Wave and Frequency Modulated Light"; Lasers in Surgery and Medicine; bearing a date of 2002; pp. 343-351; vol. 31; Wiley-Liss, Inc.

Nyitrai, Zsolt; Illyefalvi-Vitéz, Zsolt; Pinkola, János; "Preparing Stents with Masking & Etching Technology"; 26th International Spring Seminar on Electronics Technology; bearing dates of May 8, 2003-May 11, 2003 and 2003; pp. 321-324; IEEE.

Oberreuter, Helene et al.; "Identification of Coryneform Bacteria and Related Taxa by Fourier-Transform Infrared (FT-IR) Spectroscopy"; International Journal of Systematic and Evolutionary Microbiology; bearing a date of 2002; pp. 91-100; vol. 52; IUMS.

Olson, A.C. et al.; "Classification of Cultured Mammalian Cells by Shape Analysis and Pattern Recognition"; Cell Biology—Proceedings of the National Academy of Science; bearing a date of Mar. 1, 1980; pp. 1516-1520; vol. 77, No. 3; located at: http://www.pnas.org/cgi/content/abstract/77/3/1516.

Ost, V. et al.; "Flow Cytometric Differentiation of Erythrocytes and Leukocytes in Dilute Whole Blood by Light Scattering"; Cytometry; bearing a date of 1998; pp. 191-197; vol. 32; Wiley-Liss, Inc.

Ouellette, Jennifer; "Seeing With Sound"; The Industrial Physicist; bearing a date of Jun./Jul. 2004; pp. 14-17; American Institute of Physics.

Podgorsak, E.B.; "Treatment Machines for External Beam Radiotherapy"; pp. 123-160; Chapter 5; located at: http://www-naweb.iaea.org/nahu/dmrp/pdf_filed/Chapter5.pdf.

"Quantum Dot Lasers—1 Dot Makes All the Difference"; Physorg.com; bearing a date of Apr. 12, 2007; pp. 1-2; located at: http://www.physorg.com/news95617101.html.

"Radiation Therapy for Cancer: Questions and Answers"; National Cancer Institute FactSheet; bearing a date of Aug. 25, 2004; pp. 1-11; vol. 7.1.

Ranzato, M. et al.; Automatic Recognition of Biological Particles in Microscopic Images; Pattern Recognition Letters; bearing a date of Jan. 1, 2007; pp. 31-39; vol. 28, No. 1; located at: http://www.cs.nyu.edu/~ranzato/publications/ranzato-prl06.pdf.

Rolland, Jean-Paul et al., "MACS: Automatic Counting of Objects Based on Shape Recognition"; Cabios Applications Note; bearing a date of 1997; pp. 563-564; vol. 13, No. 5; Oxford University Press.

Ross, Gillian; "Commentary: Accelerated Partial Breast Irradiation: Technically Feasible But Who Will Benefit?"; Breast Cancer Research; bearing a date of May 2005; pp. 110-112; vol. 7, No. 3; BioMed Central Ltd.

Rylander, Christopher G. et al.; "Quantitative Phase Contrast Imaging of Cells with Phase Sensitive Optical Coherence Microscopy"; Optics Letters; bearing a date of 2004; pp. 1509-1511; vol. 29, No. 13; Optical Society of America.

Sage, Andrew et al.; "A Rapid and Nondestructive Method for Microbiological Testing in Pharmaceutical Manufacturing"; American Biotechnology Laboratory; bearing a date of Nov./Dec. 2006; pp. 20-23.

Sarjeant, K.C. et al.; "The Effect of Electron Beam Irradiation on the Survivial of *Salmonella enterica* Serovar Typhimurium and Psychrotrophic Bacteria on Raw Chicken Breasts Stored at Four Degrees Celsius for Fourteen Days"; Poultry Science; bearing a date of 2005; pp. 955-958; vol. 84, No. 6; Poultry Science Association.

Schenk, Eric A.; "Acoustic Microscopy of Red Blood Cells"; The Journal of Histochemistry and Cytochemistry; bearing a date of 1988; pp. 1341-1351; vol. 36, No. 10; The Histochemical Society, Inc.

Schneider, G. et al.; "Automated Image Processing System for Shape Recognition of Single Red Blood Cells Based on Out-of-Focus Images"; Biorheology—Free Communications: Methodology; bearing a date of Mar. 1995; pp. 237-238; vol. 32, No. 2; located at: http://www.ingentaconnect.com/els/0006355x/1995/00000032/00000002/art92151.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

Shapiro, David et al.; "Biological Imaging by Soft-X-Ray Diffraction Microscopy"; PNAS—Applied Physical Sciences; bearing a date of Oct. 25, 2005; pp. 15343-15346; vol. 102, No. 43; National Academy of Sciences USA.

Sikder, Shameema et al.; "Noninvasive Mitochondrial Imaging in Live Cell Culture"; Photochemistry and Photobiology; bearing a date of Nov. 2005; pp. 1569-1571; vol. 81, No. 6.

Snow, E.S.; Perkins, F.K.; Houser, E.J.; Badescu, S.C.; Reinecke, T.L.; "Chemical Detection with a Single-Walled Carbon Nanotube Capacitor"; Science; Mar. 25, 2005; pp. 1942-1945; vol. 307; www.sciencemag.org.

Sun, Tao et al.; "Broadband Impedance Spectroscopy for Single Particle in High Throughput Microfluidic Cytometer"; Proceedings of International Conference on Bio-nano-Informatics Fusion & International Forum on Biochip Technologies; bearing a date of Feb. 6, 2007; pp. 1-2.

Sun, Tao et al.; "Broadband Single Cell Impedance Spectroscopy Using Maximum Length Sequences: Theoretical Analysis and Practical Considerations"; Measurement Science and Technology; bearing a date of 2007; pp. 2859-2868; IOP Publishing.

Terstappen, L.W.M.M. et al.; "Four-Parameter White Blood Cell Differential Counting Based on Light Scattering Measurements"; Cytometry; bearing a date of 1988; pp. 39-43; vol. 9; Alan R. Liss, Inc.

Thacker, W. Lanier et al.; "Notes: Characterization of a Legionella Anisa Strain Isolated from a Patient with Pneumonia"; Journal of Clinical Microbiology; bearing a date of Jan. 1990; pp. 122-123; vol. 28, No. 1; American Society for Microbiology.

Tolomeo, M. et al.; "Mitochondrial Disruption and Apoptosis in Lymphocytes of an HIV Infected Patient Affected by Lactic Acidosis After Treatment With Highly Active Antiretroviral Therapy"; J. Clin. Pathol.; bearing a date of 2003; pp. 147-151; vol. 56; located at: www.jclinpath.com.

Tsen, K.T. et al.; "Fast Track Communication: Inactivation of Viruses with a Very Low Power Visible Femtosecond Laser"; Journal of Physics Condensed Matter; bearing a date of 2007; pp. 322102: 1-9; vol. 19; IOP Publishing.

Tsen, K.T. et al.; "Research: Inactivation of Viruses by Coherent Excitations with a Low Power Visible Femtosecond Laser"; Virology Journal; bearing a date of 2007; pp. 1-5; BioMed Central; located at: http://www.virologyj.com/content/pdf/1743-422X-4-50.pdf.

Tseng, Chun-Chieh et al.; "Inactivation of Viruses on Surfaces by Ultraviolet Germicidal Irradiation"; Journal of Occupational and Environmental Hygiene; bearing a date of Jun. 2007; pp. 400-405; vol. 4; JOEH, LLC.

Uebele, Volkmar et al.; "A Neural-Network-Based Fuzzy Classifier"; IEEE Transactions on Systems Man and Cybernetics; bearing a date of Feb. 1995; pp. 353-361; vol. 25, No. 2; IEEE.

Vidriales, M.B. et al.; "Light Scatter Characteristics of Blast Cells in Acute Myeloid Leukaemia: Association With Morphology and Immunophenotype"; Journal of Clinical Pathology; bearing a date of 1995; pp. 456-462; vol. 48; located at: http://jcp.bmj.com/cgi/content/abstract/48/5/456.

Wissing, Frank et al.; "Illumination of the Malaria Parasite Plasmodium Falciparum Alters Intracellular pH"; The Journal of Biological Chemistry; bearing a date of 2002; pp. 37747-37755; vol. 277, No. 40; The American Society for Biochemistry and Molecular Biology, Inc.; located at: http://www.jbc.org.

Wygant, I.O.; "Photoacoustic Imaging Using a Two-Dimensional CMUT Array"; IEEE Ultrasonics Symposium; bearing a date of 2005; pp. 1921-1924; IEEE.

Yeo, C.B. Allen et al.; "Bactericidal Effects of High-Power Nd:YAG Laser Radiation"; Pure Appl. Opt.; bearing a date of 1998; pp. 643-655; Vo. 7; IOP Publishing Ltd.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com/nature.

Zharov, Vladimir P. et al.; "In Vivo High-Speed Imaging of Individual Cells in Fast Blood Flow"; Journal of Biomedical Optics; bearing a date of Sep./Oct. 2006; pp. 054034: 1-4; vol. 11, No. 5; SPIE.

Zharov, Vladimir P. et al.; "In Vivo Photothermal Flow Cytometry: Imaging and Detection of Individual Cells in Blood and Lymph Flow"; Journal of Cellular Biochemistry; bearing a date of 2006; pp. 916-932; vol. 97; Wiley-Liss, Inc.

Zharov, Vladimir et al.; "Photoacoustic Flow Cytometry Monitors Cells Circulating in Vivo"; SPIE: The International Society for Optical Engineering; bearing a date of 2006; pp. 1-3; located at: http://spie.org/x8596.xml?highlight=x2416.

Zheng, Siyang et al.; "Design and Fabrication of a Micro Coulter Counter with Thin Film Electrodes"; Proceedings of 2006 International Conference on Microtechnologies in Medicine and Biology; bearing a date of May 9-12, 2006; pp. 16-19; IEEE.

Zimmerman, Peter A. et al.; "Diagnosis of Magnetic Deposition Microscopy"; The American Journal of Tropical Medicine and Hygiene; bearing a date of 2006; pp. 568-572; vol. 74, No. 4; The American Society of Tropical Medicine and Hygiene; located at: http://www.ajtmh.org/cgi/content/abstract/74/4/568.

European Search Report; European App. No. EP 08 83 4851; Dec. 2, 2010 (received by our Agent on Dec. 14, 2010); pp. 1-6.

* cited by examiner

FIG. 12
FIG. 12A
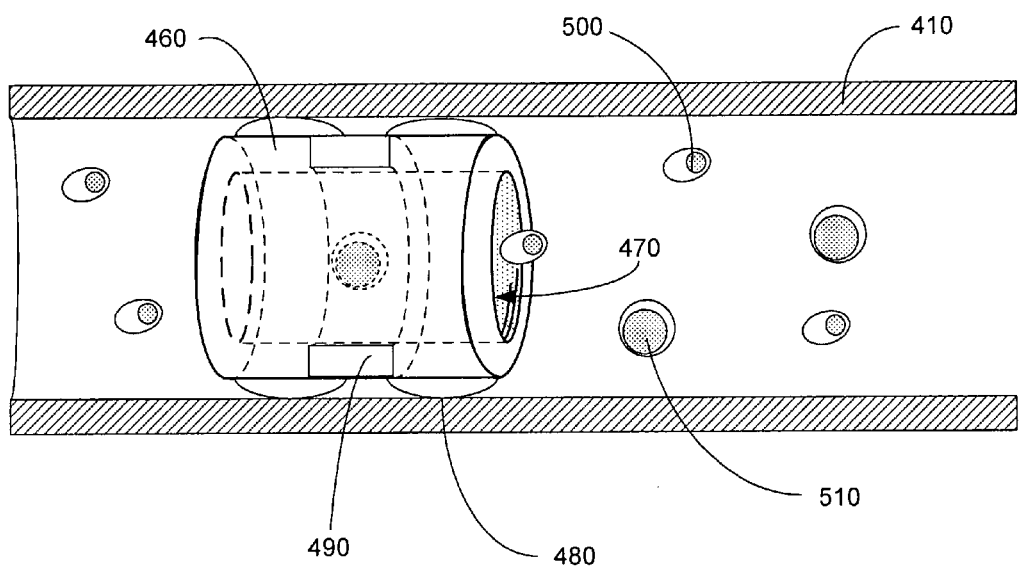
FIG. 12B
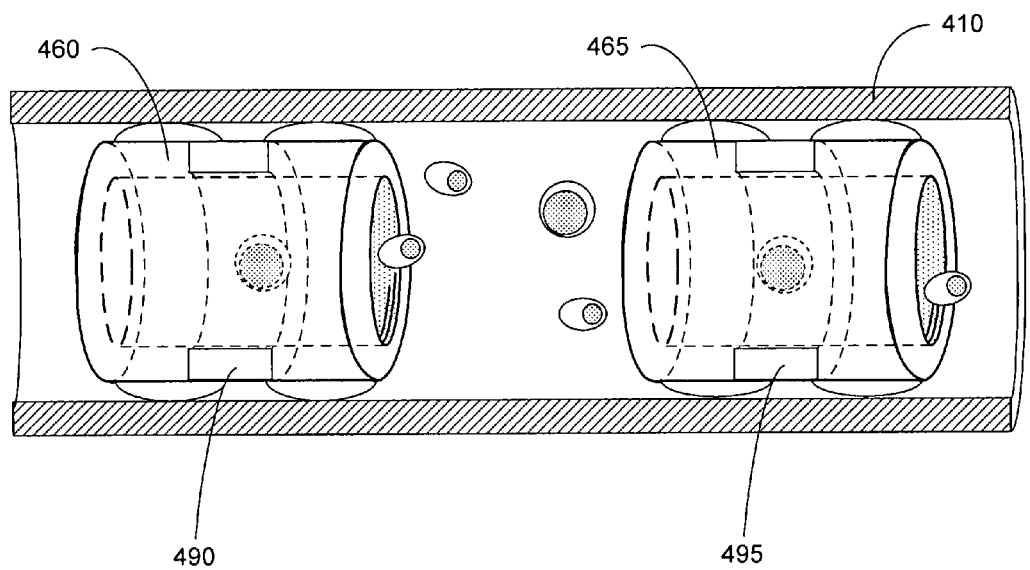

FIG. 13
FIG. 13A
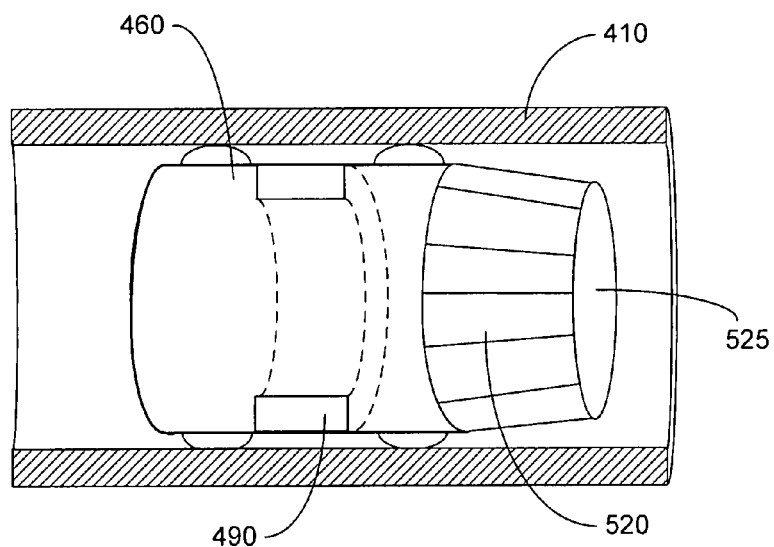
FIG. 13B
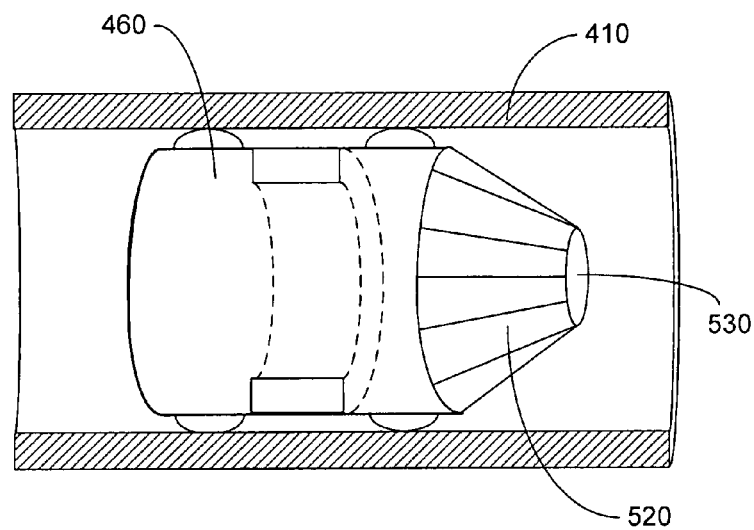

FIG. 15
FIG. 15A
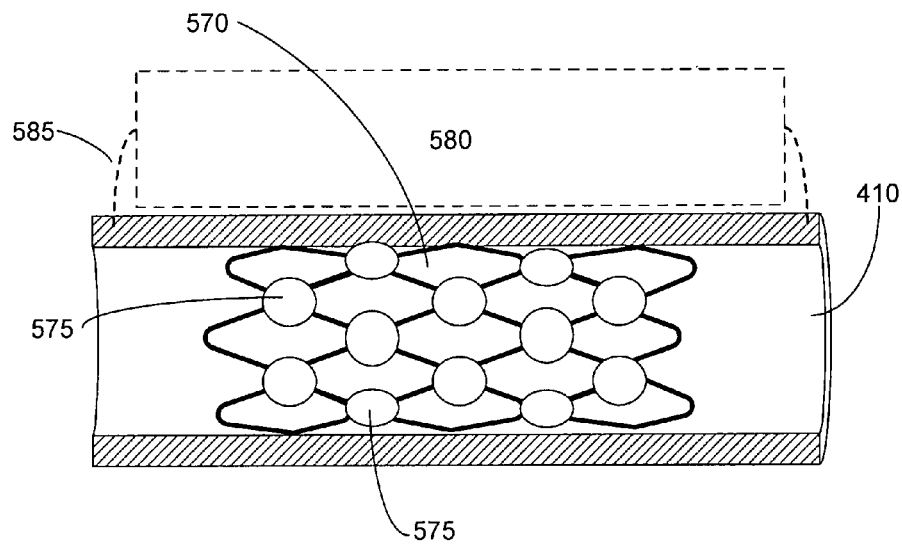
FIG. 15B
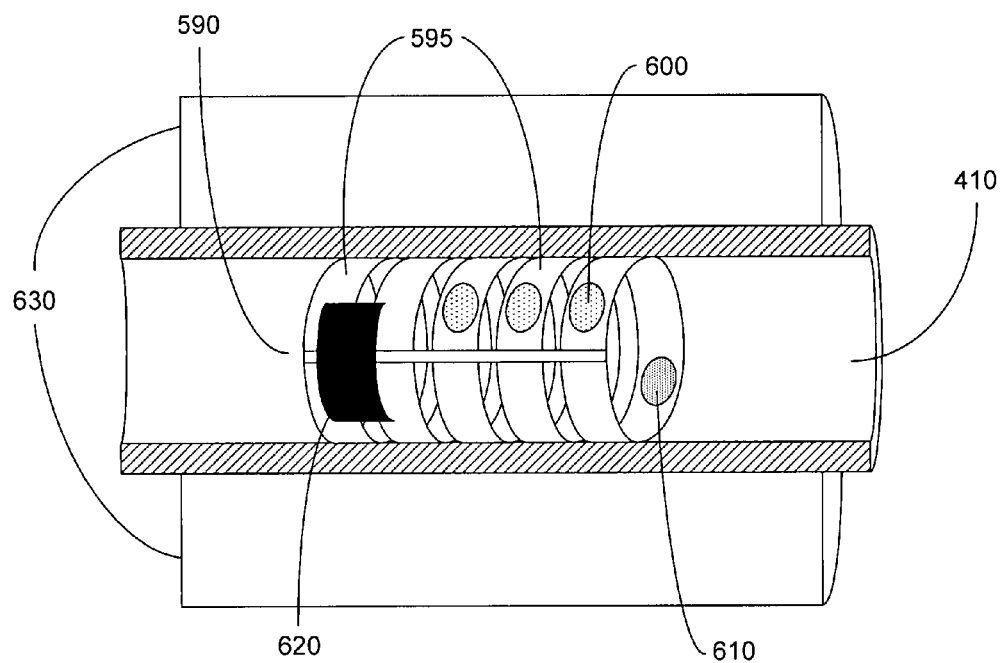

FIG. 16
FIG. 16A
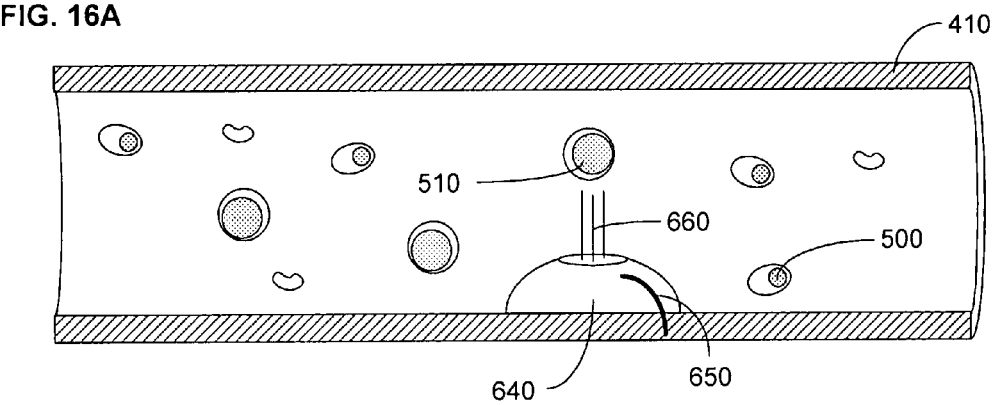
FIG. 16B
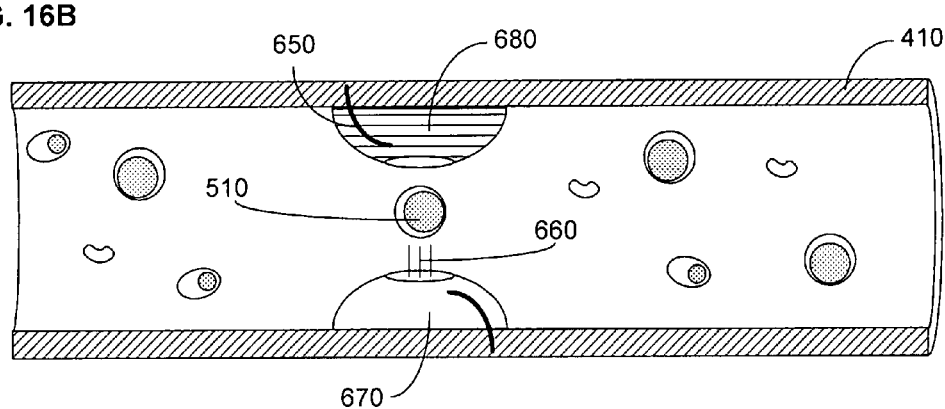
FIG. 16C
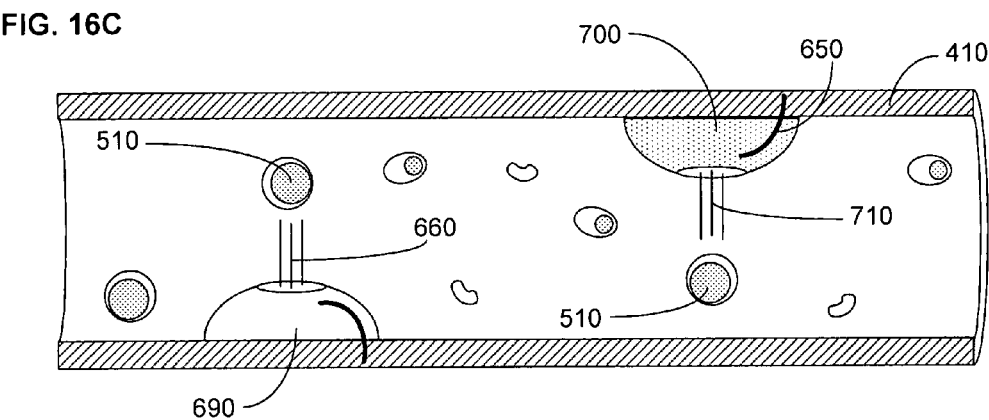

FIG. 17
FIG. 17A
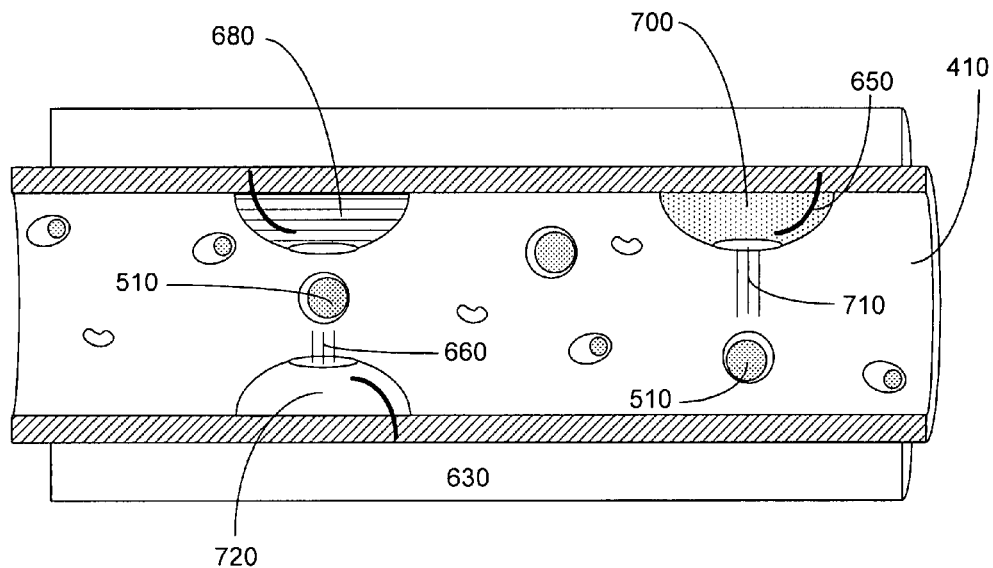
FIG. 17B
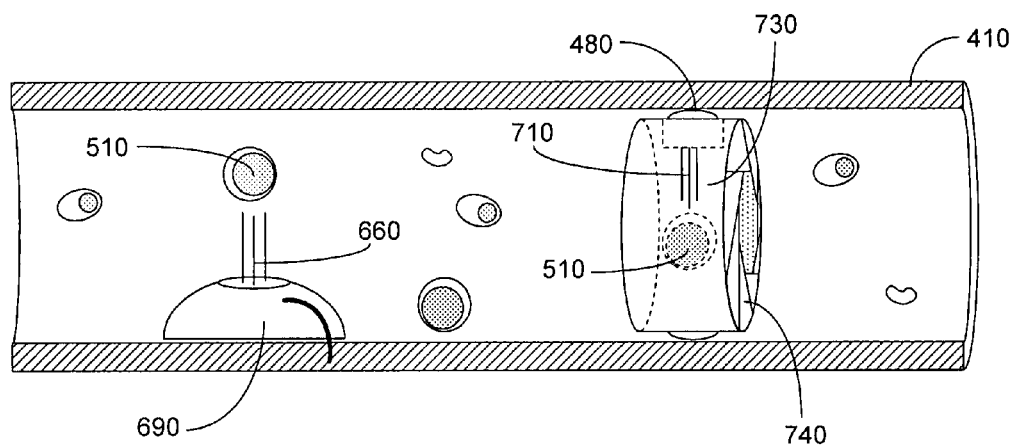

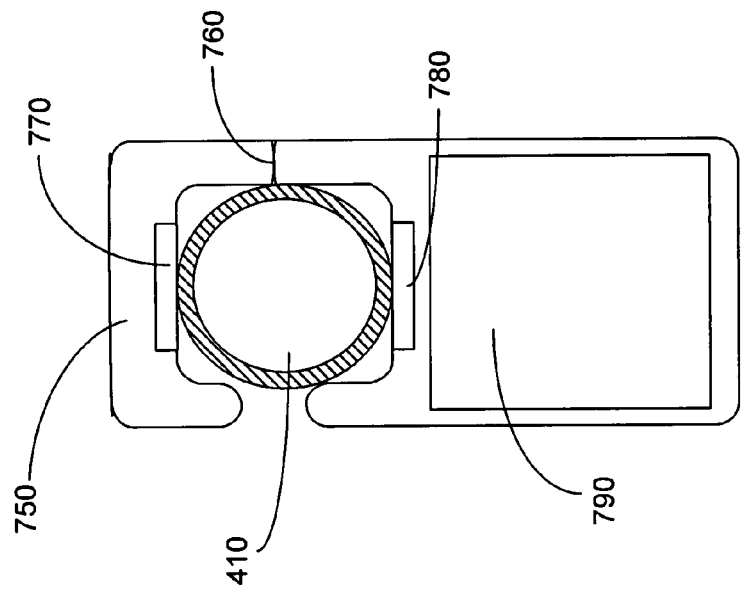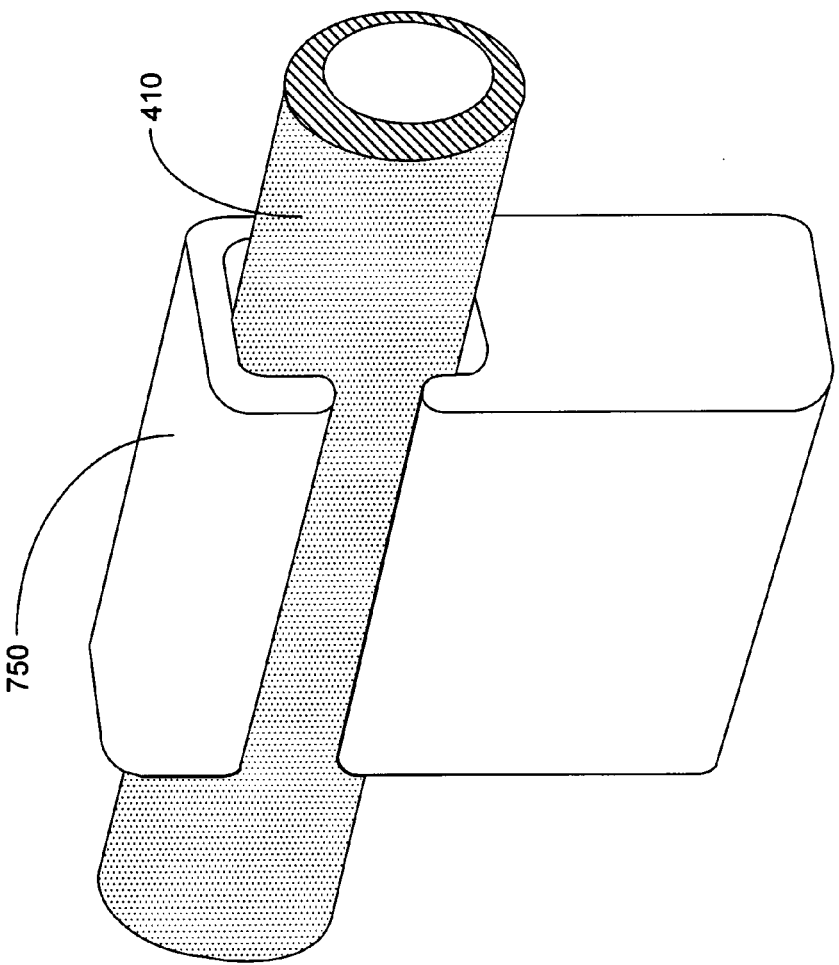

FIG. 19
FIG. 19A
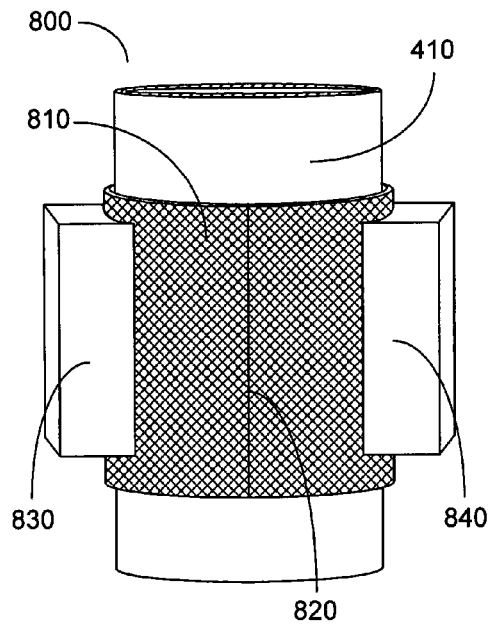
FIG. 19B
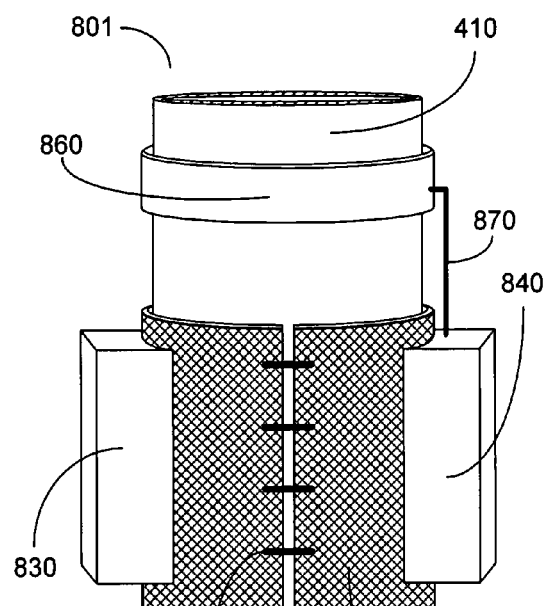
FIG. 19C
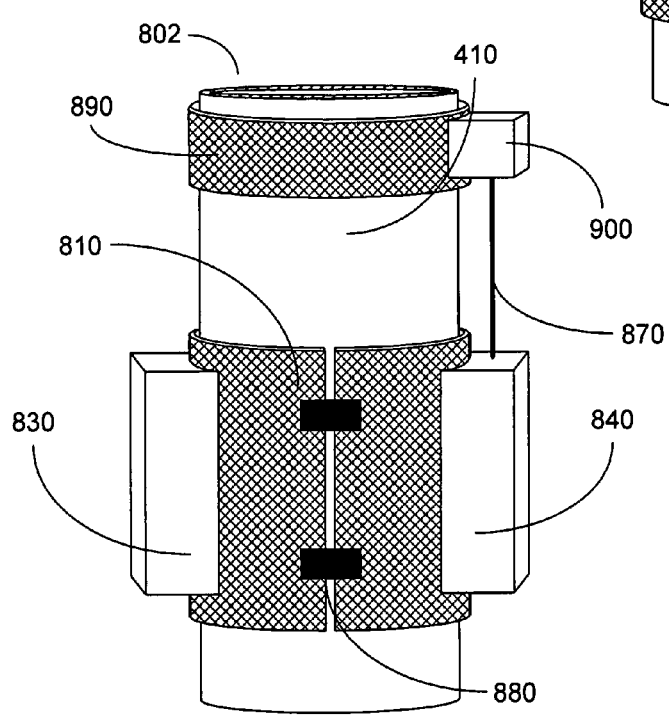

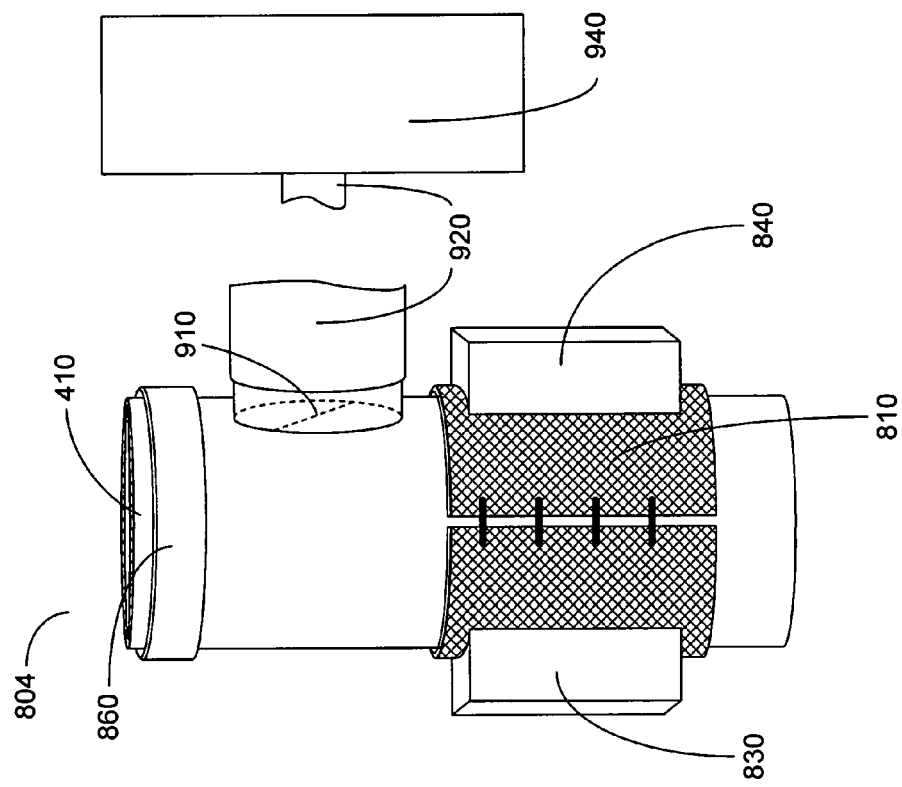
FIG. 20
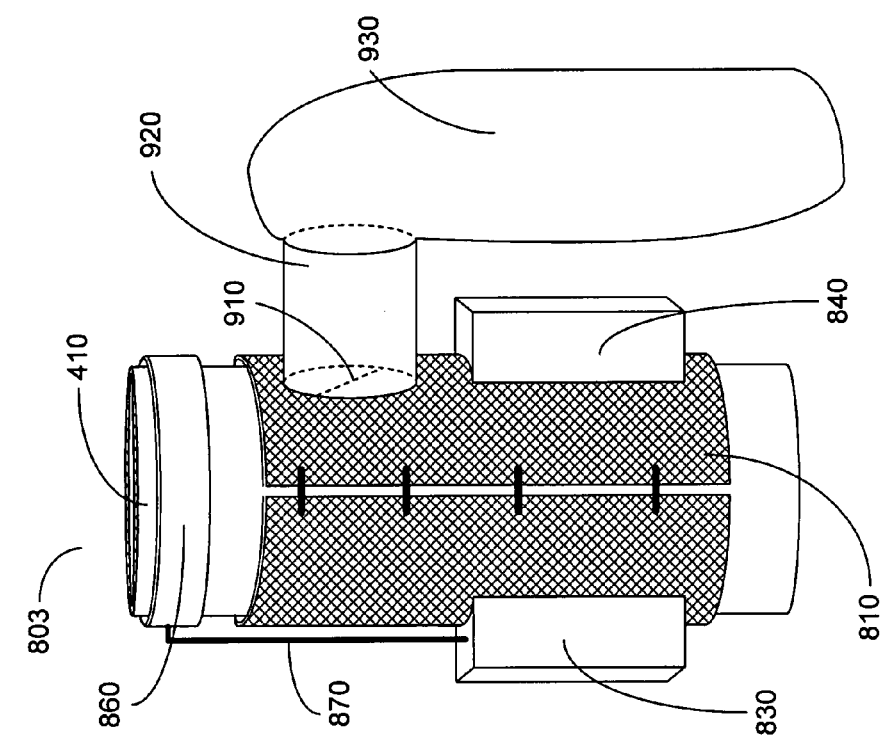
FIG. 20A
FIG. 20B

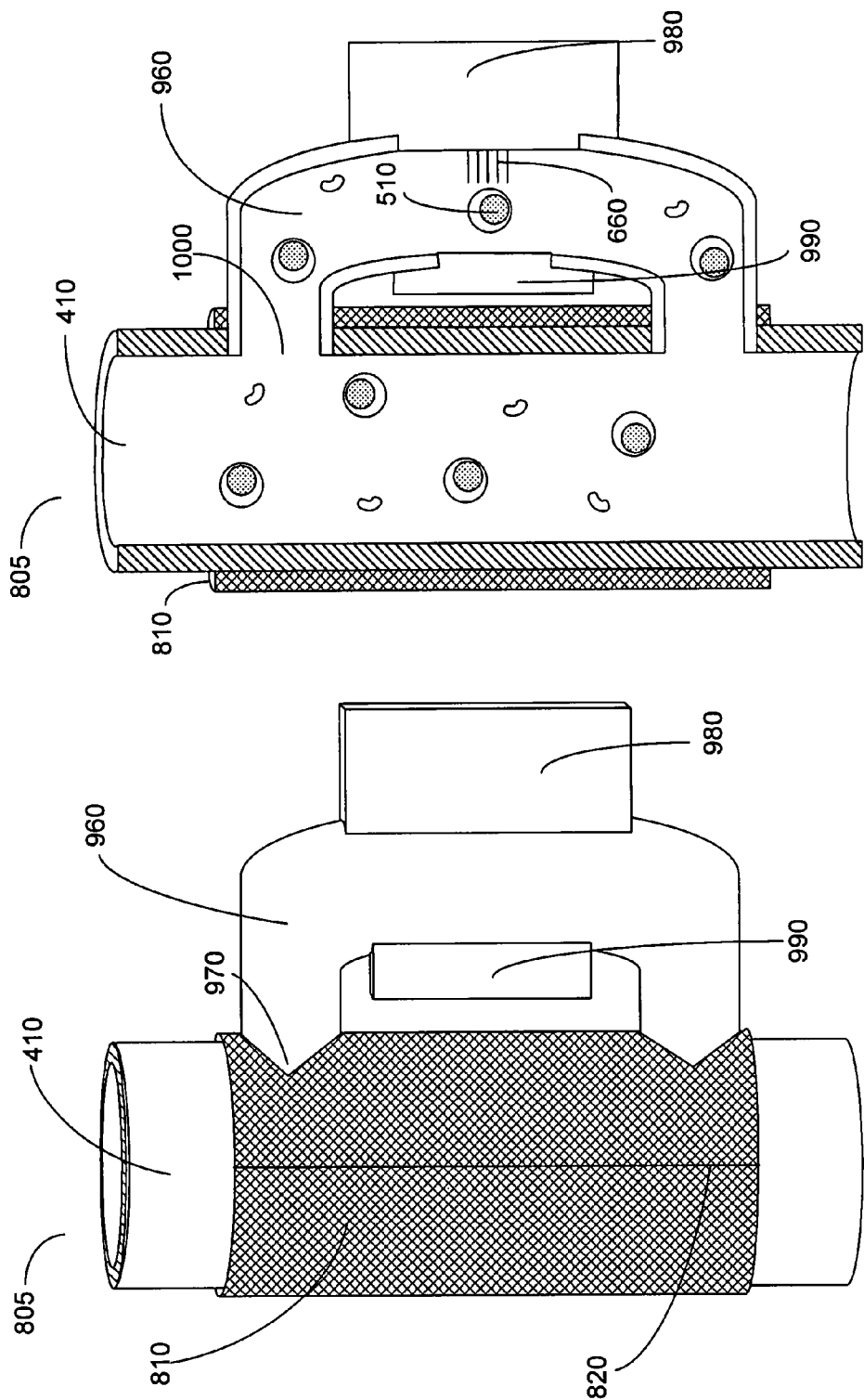

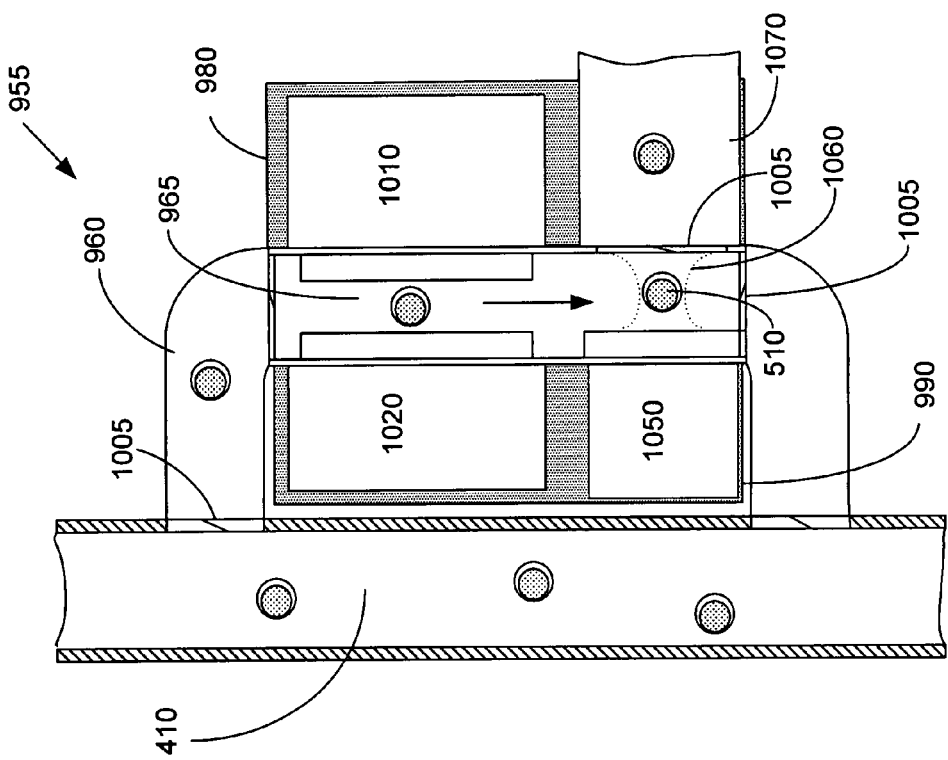
FIG. 22
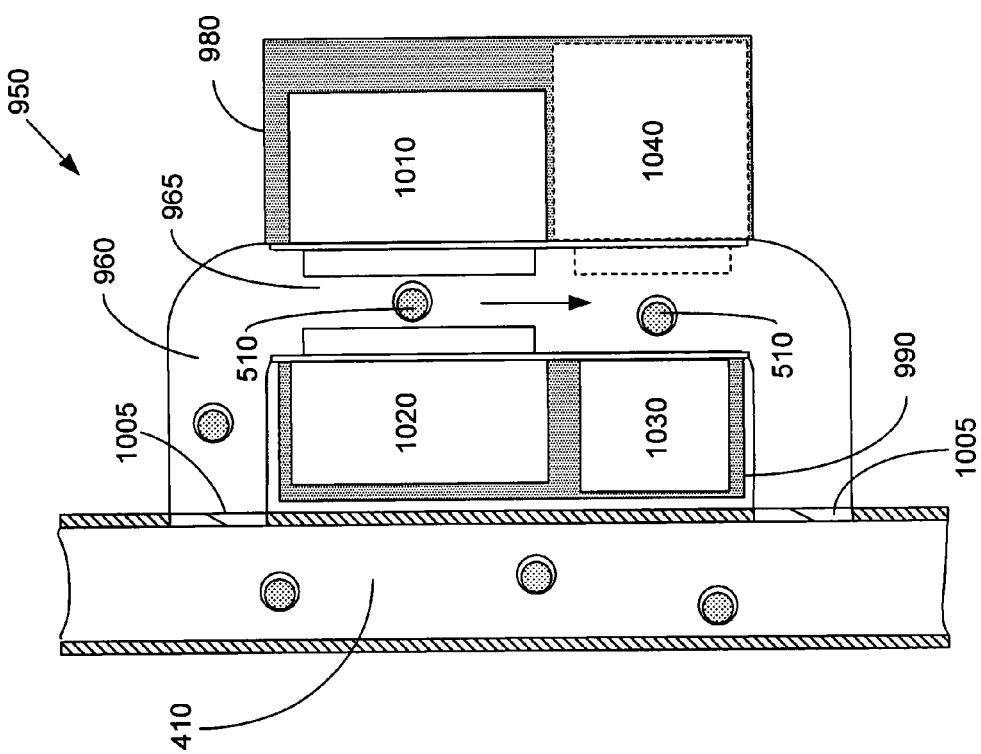

FIG. 23
FIG. 23A
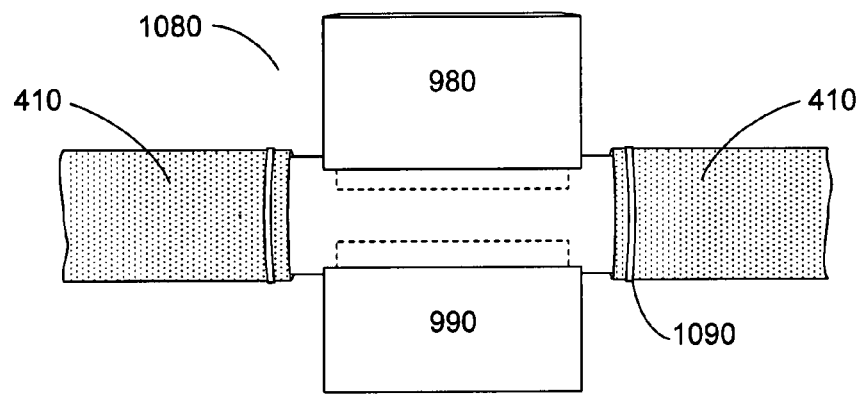
FIG. 23B
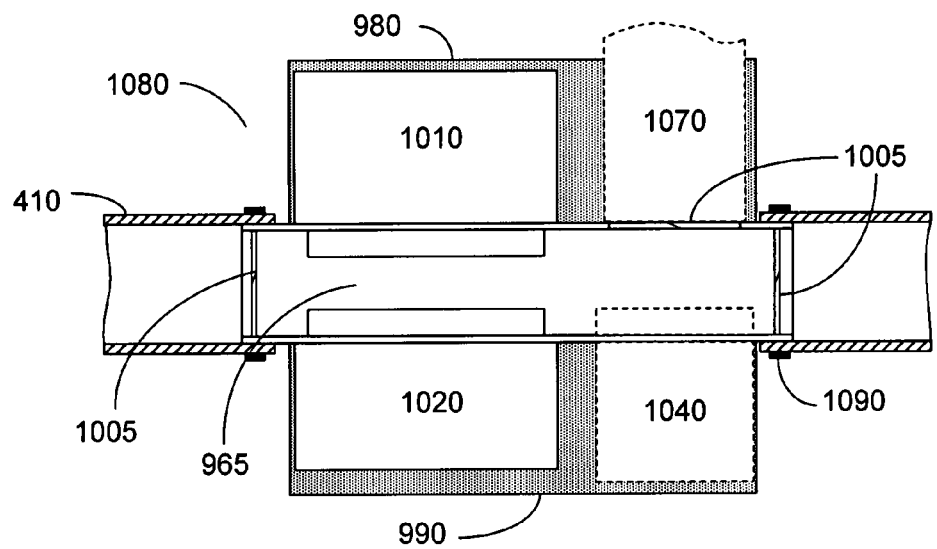

FIG. 24
FIG. 24A
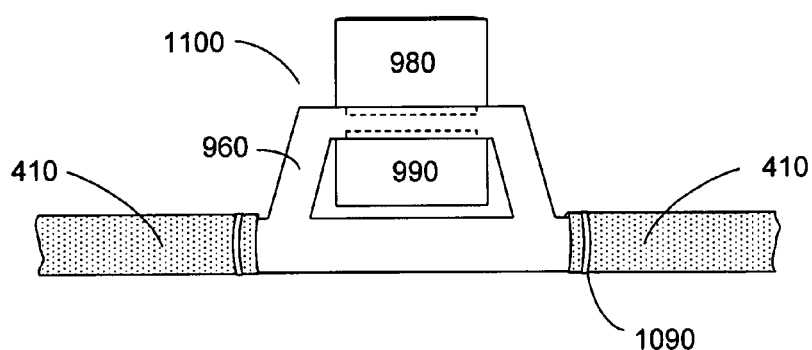
FIG. 24B
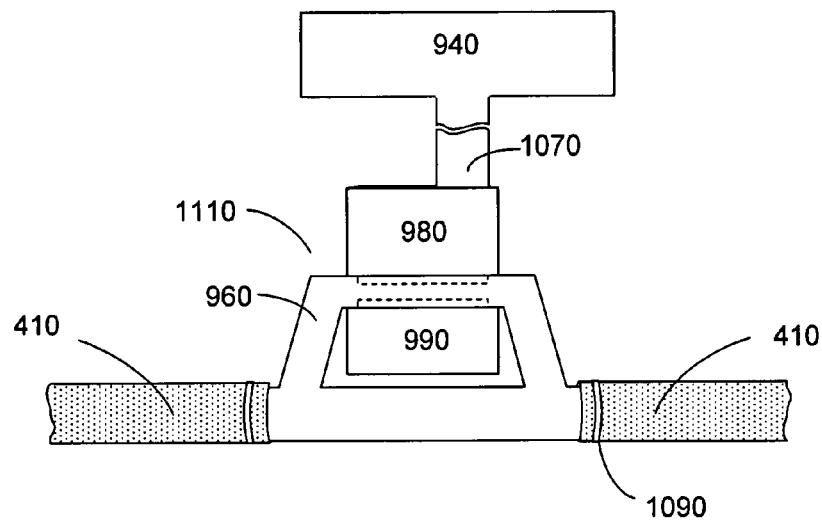

US 8,285,367 B2

VASCULATURE AND LYMPHATIC SYSTEM IMAGING AND ABLATION ASSOCIATED WITH A RESERVOIR

CROSS-REFERENCE TO RELATED APPLICATIONS

The present application is related to U.S. patent application Ser. No. 11/973,010, entitled VASCULATURE AND LYMPHATIC SYSTEM IMAGING AND ABLATION, naming Roderick A. Hyde, Edward K. Y. Jung, Nathan P. Myhrvold, Clarence T. Tegreene, Willard H. Wattenburg, Lowell L. Wood, Jr. and Richard N. Zare as inventors, filed 3, Oct., 2007.

The present application is related to U.S. patent application Ser. No. 11/973,357, entitled VASCULATURE AND LYMPHATIC SYSTEM IMAGING AND ABLATION ASSOCIATED WITH A LOCAL BYPASS naming Roderick A. Hyde, Edward K. Y. Jung, Nathan P. Myhrvold, Clarence T. Tegreene, Willard H. Wattenburg, Lowell L. Wood, Jr. and Richard N. Zare as inventors, filed 4, October, 2007.

All subject matter of the Related Applications and of any and all parent, grandparent, great-grandparent, etc. applications of the Related Applications is incorporated herein by reference to the extent such subject matter is not inconsistent herewith.

SUMMARY

The present application relates, in general, to devices and methods for imaging and ablation of medical targets. Such devices and methods are useful for ablating target cells and/or tissues as well as treatment, prevention, and/or diagnosis of a variety of diseases and disorders. Devices are configured to be used internally and untethered. Various methods include using one or more of the devices for ablating target cells within the vascular or lymphatic systems. Illustrative examples include using one or more of the devices or methods to treat and/or ablate blood-borne pathogens and/or neoplasms.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 12, FIG. 13, FIG. 14, FIG. 15, FIG. 16 and FIG. 17 show schematics of illustrative embodiments of systems including devices configured to function in a vessel lumen.

FIG. 18, FIG. 19, and FIG. 20 show schematics of illustrative embodiments of systems including devices configured to function proximal to a vessel lumen optionally including a reservoir.

FIG. 21, FIG. 22, FIG. 23, and FIG. 24 show schematics of illustrative embodiments of systems including devices including a local bypass and optionally including a reservoir.

DETAILED DESCRIPTION

Figure 1:
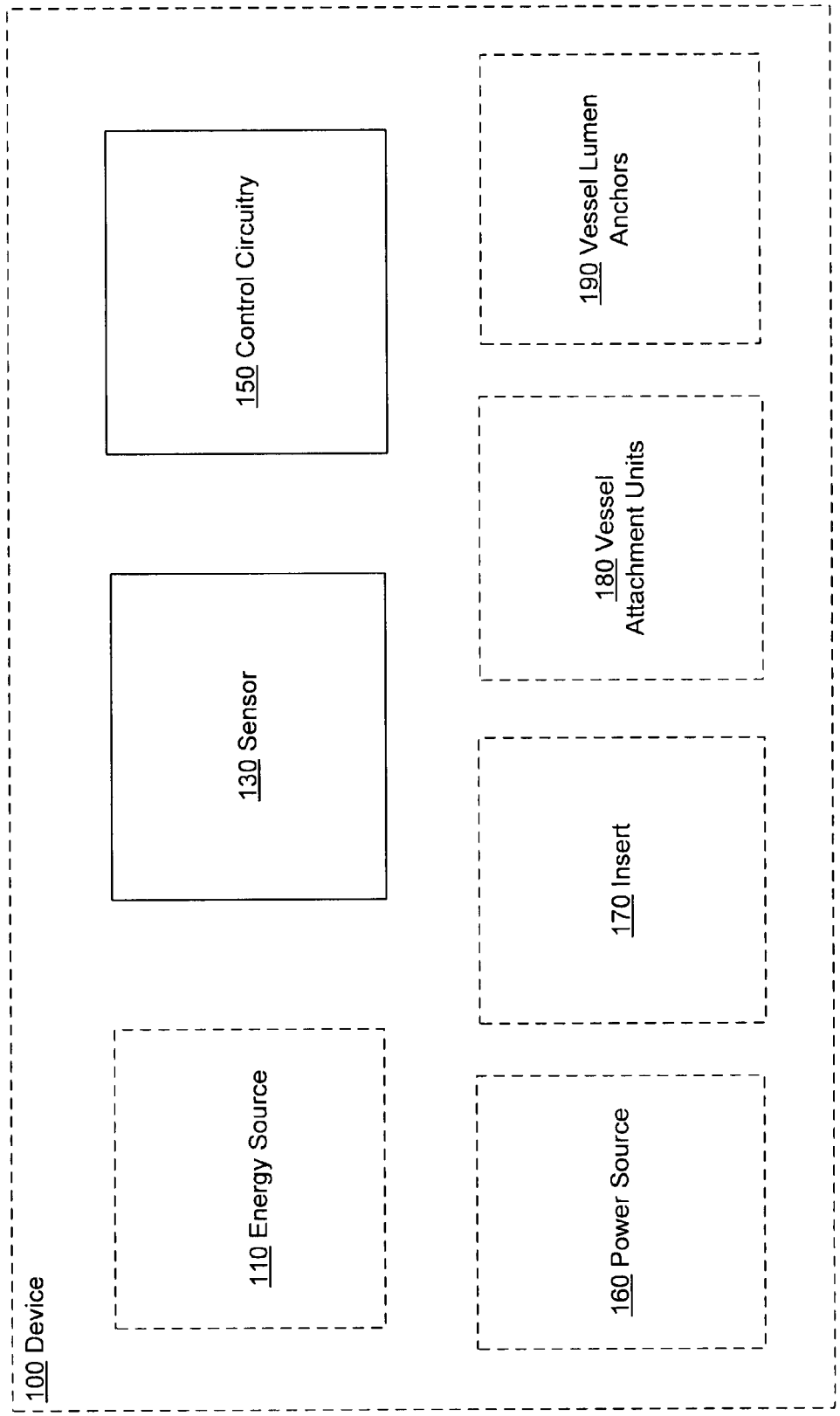
FIG. 1 shows a schematic of an illustrative device in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application relates, in general, to systems, devices, and methods for imaging and optionally ablating medical targets in the vasculature and lymphatic systems for treatment, prevention and/or diagnosis. Those having skill in the art will appreciate that the specific devices and methods described herein are intended as merely illustrative of their more general counterparts.

In one aspect, FIG. 1 through FIG. 10 depict one or more embodiments of one or more device 100, 200, and/or 300, configured to image and optionally to ablate one or more targets or target areas. Although one or more embodiments of one or more devices may be presented separately herein, it is intended and envisioned that one or more devices and/or embodiments of one or more devices, in whole or in part, may be combined and/or substituted among the devices to encompass a full disclosure of the one or more devices. As disclosed below, one or more devices may be used in one or more methods of treatment, prevention, and/or diagnosis as well as methods for imaging and/or impairing targets as described herein.

FIG. 1, FIG. 2, FIG. 3, FIG. 4, FIG. 5, and FIG. 6 depict illustrative embodiments of one or more device 100 having one or more sensors 130 configured to function in, or proximal to, one or more blood vessel or lymph vessel and to capture one or more image responses; and control circuitry 150 coupled to the one or more sensors 130 and responsive to at least partially identify one or more targets in real time at least partially based on the one or more captured image responses. The one or more device 100 optionally includes one or more of one or more energy source 110, one or more power source 160, one or more insert 170, one or more vessel attachment units 180, and/or one or more vessel lumen anchors 190.

Figure 7:
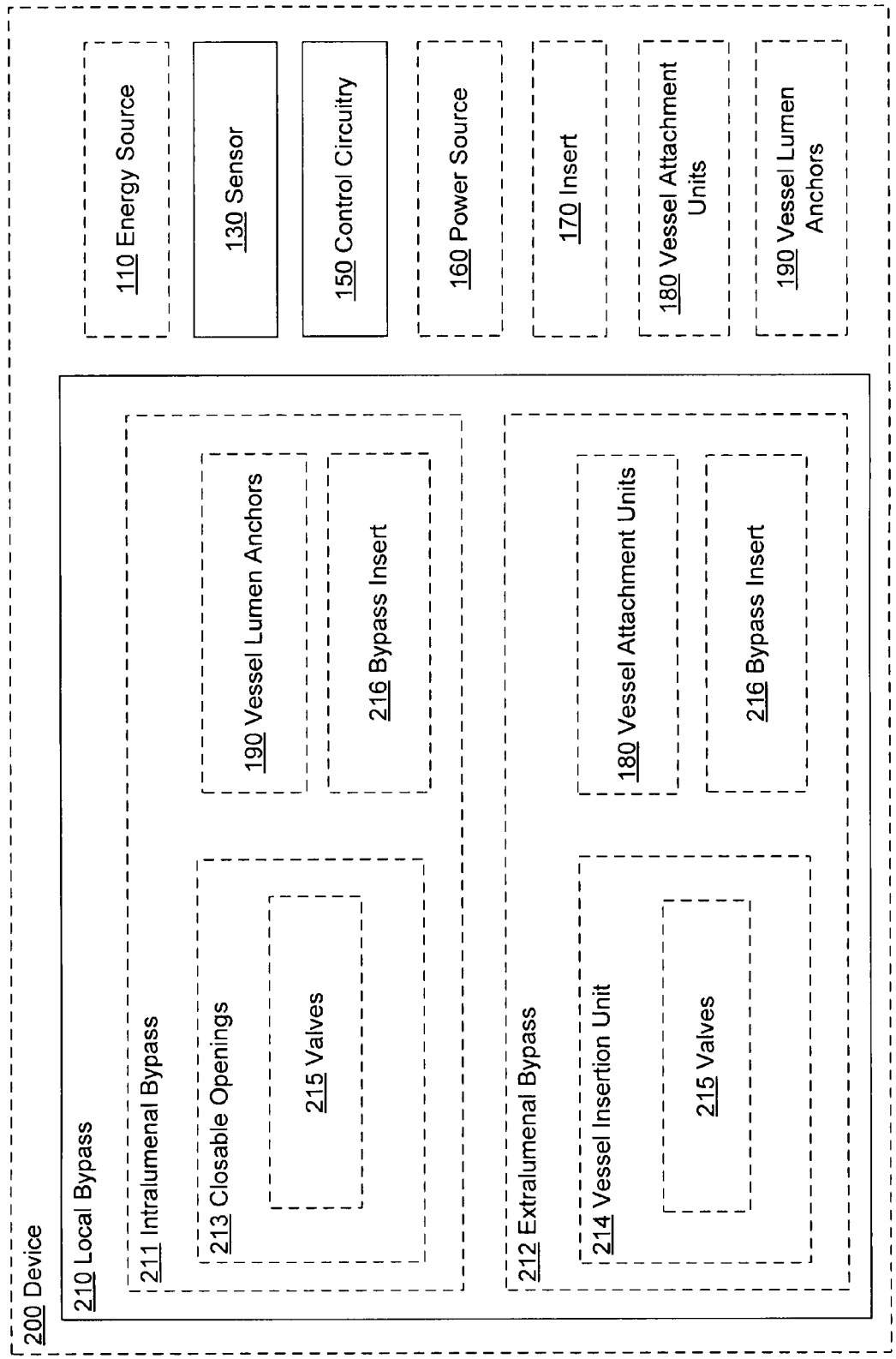
FIG. 7 and FIG. 8 show schematics of an illustrative device including a local bypass in which embodiments may be implemented.
Figure 8:
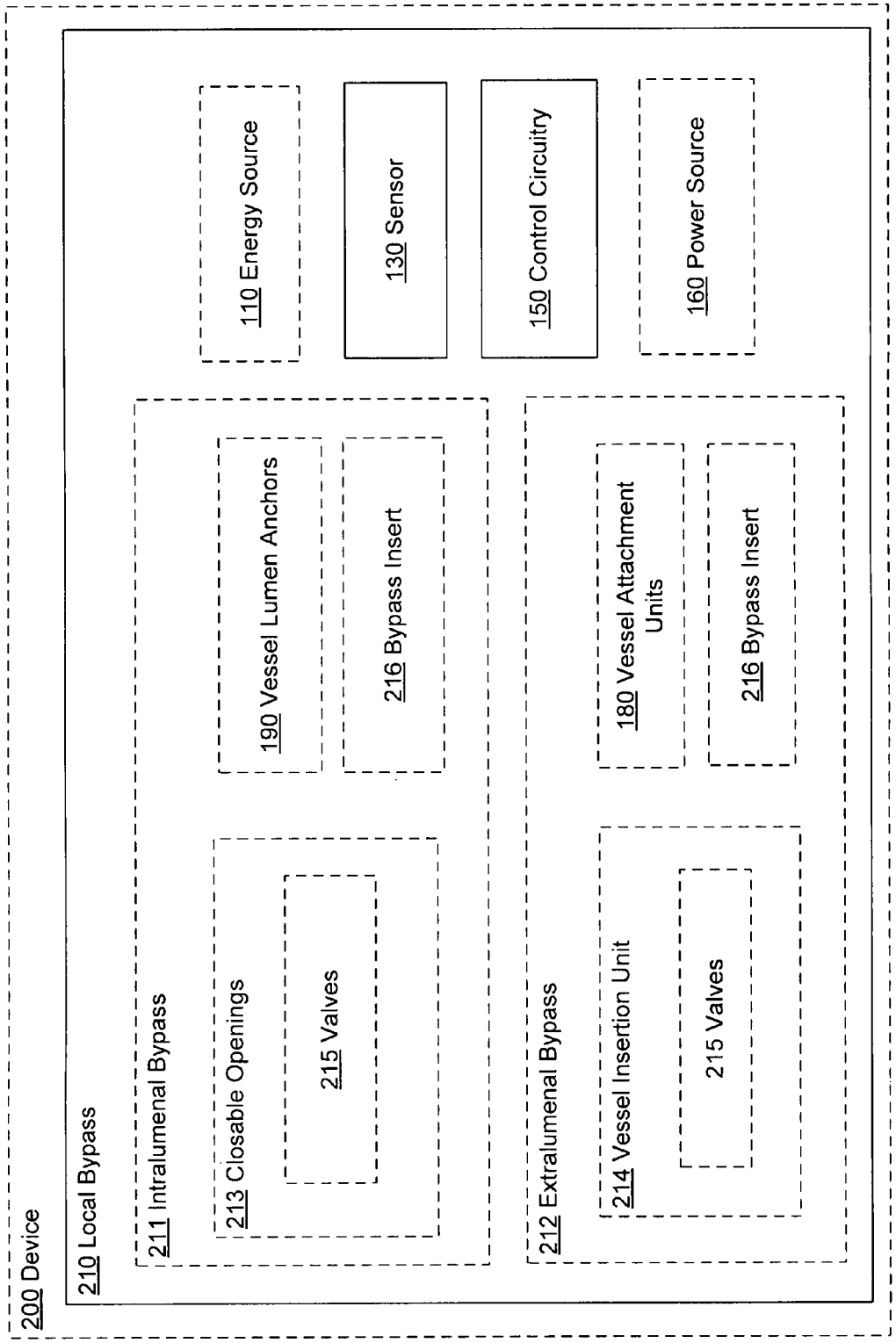

FIG. 7 and FIG. 8 depict illustrative embodiments of one or more device 200 having a local bypass 210 configured to function in, or proximal to, one or more blood vessel or lymph vessel; one or more sensors 130 configured to function in, or proximal to, the local bypass and to capture one or more image responses; and control circuitry 150 coupled to the one or more sensors 130 and responsive to at least partially identify one or more targets in real time at least partially based on the one or more captured image responses. The one or more device 200 optionally includes one or more of one or more energy source 110, one or more power source 160, one or more insert 170, one or more vessel attachment units 180, and/or one or more vessel lumen anchors 190.

Figure 9:
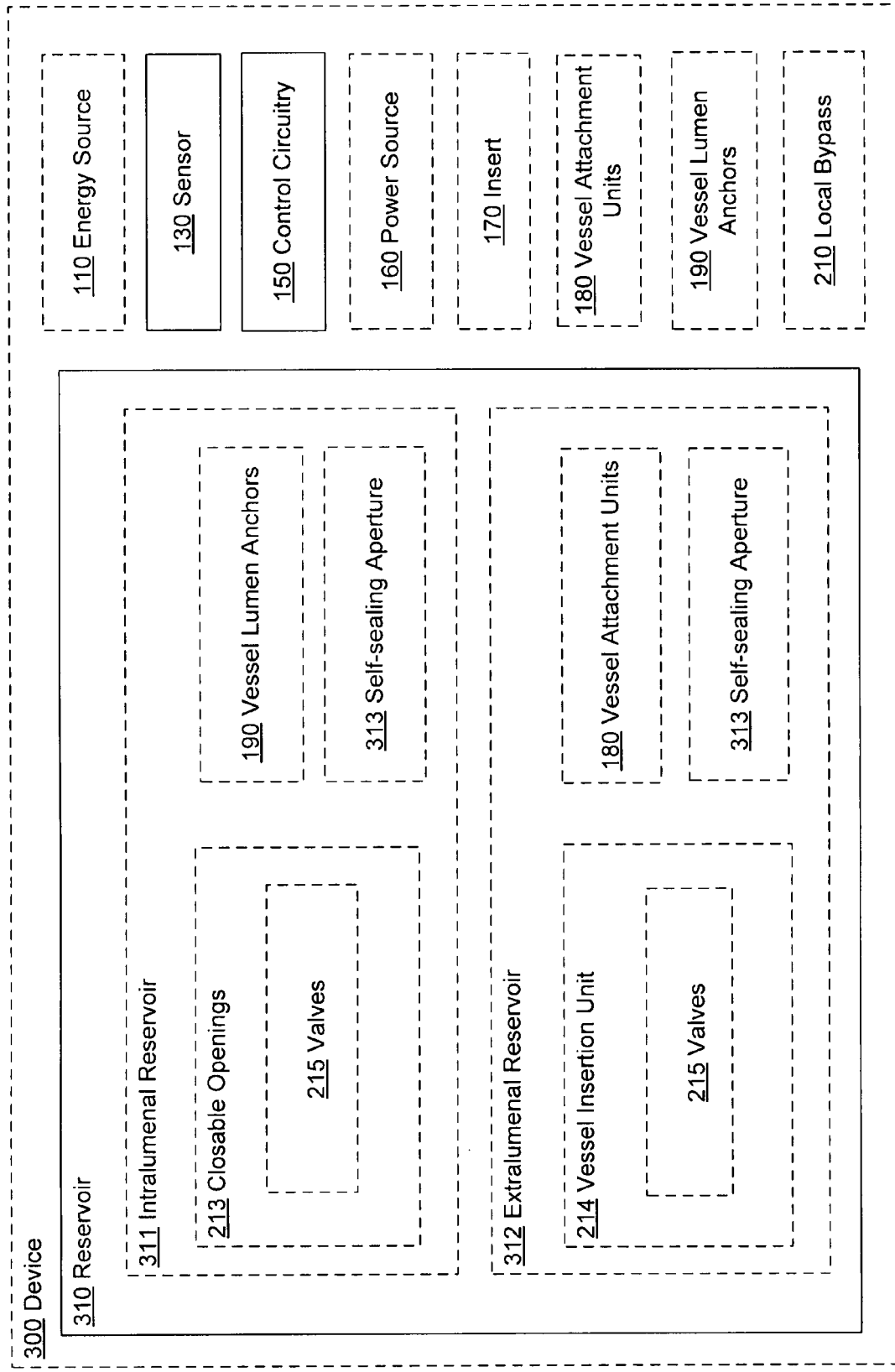
FIG. 9 and FIG. 10 show schematics of an illustrative device including a reservoir in which embodiments may be implemented.
Figure 10:
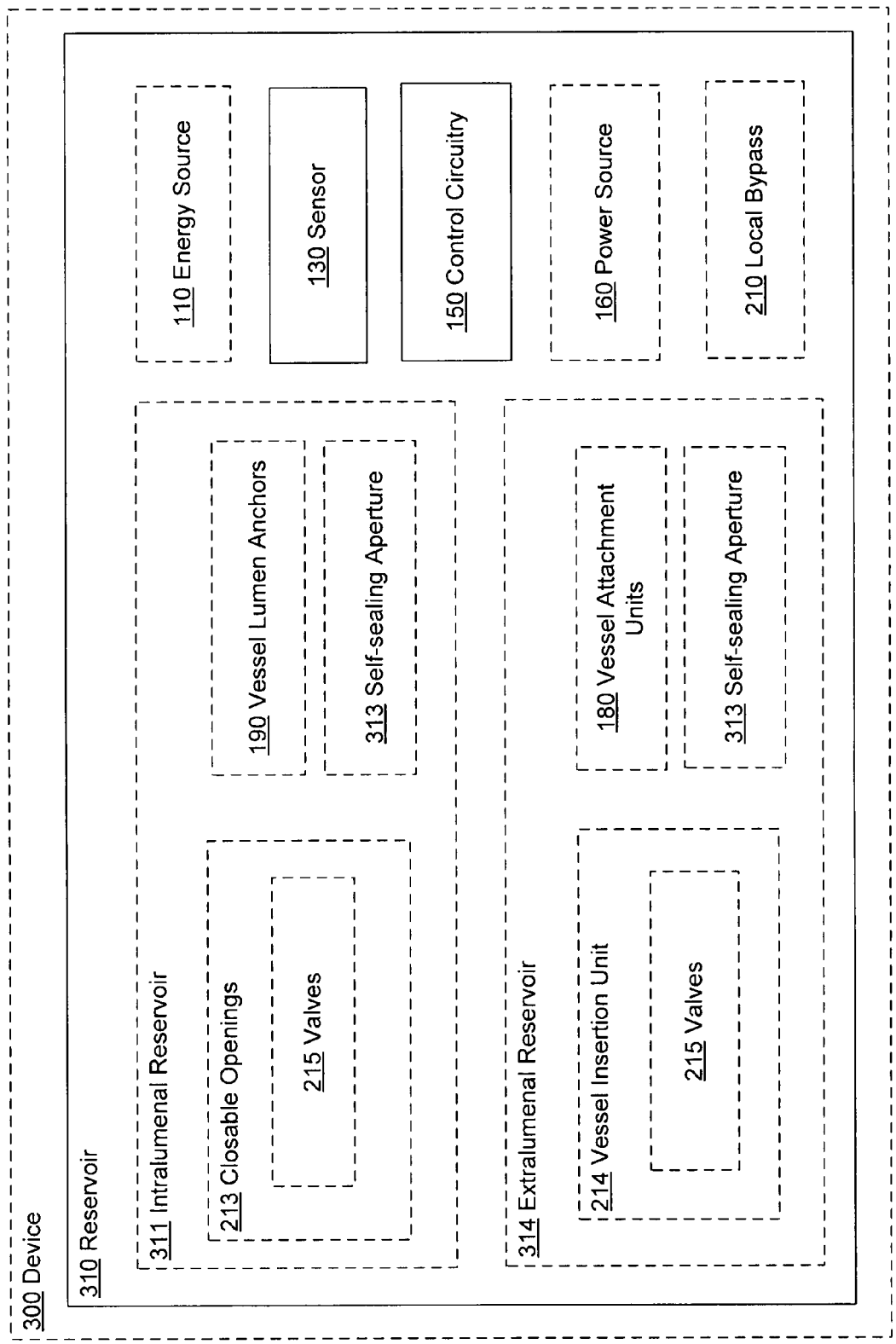

FIG. 9 and FIG. 10 depict illustrative embodiments of one or more device 300 having one or more reservoirs 310 responsive to control circuitry 150, and configured to receive one or more targets and to function in, or proximal to, one or more blood vessel or lymph vessel; one or more sensors 130 configured to function in, or proximal to, the one or more reservoirs and to capture one or more image responses; and control circuitry 150 coupled to the one or more sensors 130 and responsive to at least partially identify one or more targets in real time at least partially based on the one or more captured image responses. The one or more device 300 optionally includes one or more of one or more energy source 110, one or more power source 160, one or more insert 170, one or more vessel attachment units 180, and/or one or more vessel lumen anchors 190.

The one or more devices 100, 200, and/or 300 in whole, or in part, are configured for use in, or proximal to, one or more blood vessels and/or lymph vessels of an organism. In illustrative embodiments, the one or more device 100, 200, and/or 300, in part or in whole, is an intra-lumenally sized device (e.g. small enough to be placed in a blood vessel and/or lymph vessel while not necessarily obstructing the flow). In illustrative embodiments, the one or more device 100, 200, and/or 300, in part or in whole, is configured for use proximal to a blood vessel or lymph vessel.

As used herein, the term "lumen" may include, but is not limited to, part or all of the open interior of a blood vessel (including e.g., arteries, veins, and capillaries), or of a lymph vessel. As used herein, the term "proximal to" may include, but is not limited to, a space and/or area near to a blood or lymph vessel and/or vessel lumen. Locations that are proximal to a vessel may include, for example, locations external to the vessel wall optionally where there is space for implanting one or more devices in whole or in part, and optionally to facilitate external access to the devices in whole or in part. In some embodiments, "proximal to" may include distances such as, but not limited to, approximately 0.1, 1.0, 10, and/or 100 µms and/or 0.1, 1.0, 10, and/or 100 mms, and may optionally include larger and/or smaller distances depending on, for example, the availability of space, the size of the device and/or the vessel, and the characteristics of the energy (e.g. electromagnetic energy, particle beam, two-photon, pulsed, etc.) and/or the sensors (e.g. sensitivity of detection). Those of skill in the art would know (and/or are able to calculate) the applicable distance for each form of energy.

The one or more devices 100, 200, and/or 300 are, in whole or in part, untethered. As used herein, the term "untethered" includes not required to be physically linked to one or more external components and/or not physically linked to one or more external components. In some embodiments, untethered may include autonomous functioning, such that there is, for example, no required external control circuitry link as well.

Embodiments of one or more device 100, 200, and/or 300 may be configured as a self-contained unit that includes all functionalities necessary for operation of the device, or configured as one or more subparts in one or more locations separate from one another (and optionally external to the subject), wherein one or more of the subparts includes one or more essential and/or non-essential functionalities. In illustrative examples, one subpart may be placed within a lumen of, for example, a blood vessel, and another subpart placed, for example, proximal to the blood vessel optionally in a location more accessible from the exterior of the subject, or where there is additional space. In illustrative embodiments, a remote portion may provide for monitoring of the lumen-based device, data collection, or data analysis, and/or remote-control of one or more other functions such as image capture, and energy use. The remote portion may be at a separate location within the body of the subject, or outside the body of the subject. Data and/or power signals may be transmitted between the one or more subparts using electromagnetic signals, for example, or electrical or optical links. Methods of distributing functionalities of a system between hardware, firmware, and software at located at two or more sites are well known to those of skill in the art.

Embodiments of one or more device 100, 200, and/or 300 may be described as having one or more subparts including, but not limited to, one or more energy sources 110, one or more sensors 130, one or more control circuitry 150, one or more power sources 160, one or more insert 170, one or more vessel attachment units 180, and/or one or more vessel lumen anchors 190. In some embodiments, one or more subpart may be a physically distinct unit. In some embodiments, one or more subpart is combined with one or more other subpart to form a single unit optionally with no physically discernible separation. Some embodiments include a first, second, third, fourth, fifth, etc. energy source 110, sensor 130, control circuitry 150, power sources 160, insert 170, vessel attachment units 180, and/or vessel lumen anchors 190, for example. One or more of the one, two three, four, five, etc. components may be part of the same component and/or physical entity, or one or more components may be a separate physical entity. For example, there may be two lasers in a device, or there may be one laser able to provide both excitation and ablation energy. For example, there may be two sensors in a device, or there may be one sensor able to detect a variety of energy wavelengths.

As used herein, the term "internal location" may include locations within the body of a subject appropriate for the placement of one or more device and/or part of one or more device. In illustrative embodiments, one or more internal locations may be proximal to one or more blood vessel and/or lymph vessel. Such internal locations are known to those with skill in the art and/or described herein. Methods for placing one or more devices in internal locations are known to those in the medical profession, for example. As used herein, the term "medical professional" may include, but is not limited to, physicians, nurses, mid-wives, and/or nurse practitioners, dental professionals, such as but not limited to, dentists, orthodontists, dental hygienists, and veterinary professionals, including but not limited to, veterinarians during treatment optionally including surgery.

As used herein, the term "subject" may include, but is not limited to, one or more living entities including, but not limited to, animals, mammals, humans, reptiles, birds, amphibians, and/or fish. The animals may include, but are not limited to, domesticated, wild, research, zoo, sports, pet, primate, marine, and/or farm animals. Animals include, but are not limited to, bovine, porcine, swine, ovine, murine, canine, avian, feline, equine, and/or rodent animals. Domesticated and/or farm animals include, but are not limited to, chickens, horses, cattle, pigs, sheep, donkeys, mules, rabbits, goats, ducks, geese, chickens, and/or turkeys. Wild animals include, but are not limited to, non-human primates, bear, deer, elk, raccoons, squirrels, wolves, coyotes, opossums, foxes, skunks, and/or cougars. Research animals include, but are not limited to, rats, mice, hamsters, guinea pigs, rabbits, pigs, dogs, cats and/or non-human primates. Pets include, but are not limited to, dogs, cats, gerbils, hamsters, guinea pigs and/or rabbits. Reptiles include, but are not limited to, snakes, lizards, alligators, crocodiles, iguanas, and/or turtles. Avian animals include, but are not limited to, chickens, ducks, geese, owls, sea gulls, eagles, hawks, and/or falcons. Fish include, but are not limited to, farm-raised, wild, pelagic, coastal, sport, commercial, fresh water, salt water, and/or tropical. Marine animals include, but are not limited to, whales, sharks, seals, sea lions, walruses, penguins, dolphins, and/or fish.

The dimensions and mechanical properties (e.g., rigidity) of the one or more devices 100, 200, and/or 300, in part or in whole, and particularly of the structural elements of the one or more device (e.g. one or more inserts 170, one or more vessel attachment units 180, one or more vessel lumen anchors 190, one or more local bypass 210, one or more closable openings 213, one or more vessel insertion unit 214, one or more bypass insert 216, one or more intralumenal reservoir 311, and/or one or more self-sealing aperture 313, among others), may be selected for compatibility with the location of use in order to provide for reliable positioning and/or to provide for movement of the device while preventing damage to the vessel, the vessel lumen, and/or internal location and its surrounding structure. In illustrative embodiments, part or all of a device is configured for use within a blood vessel or lymph vessel lumen. In illustrative embodiments, part or all of a device is configured for use proximal to (i.e. at least partially external to) a blood vessel or lymph vessel. In illustrative embodiments, at least part of an untethered device is internal to a subject. In illustrative embodiments, part of an untethered device is external to a subject. In illustrative embodiments, part or all of a device is immobile.

The choice of structural element size and configuration appropriate for a particular blood or lymph vessel location may be selected by a person of skill in the art, optionally a medical professional. Structural elements may be constructed using a variety of manufacturing methods, from a variety of materials. Appropriate materials may include metals, ceramics, polymers, and composite materials having suitable biocompatibility, sterilizability, mechanical, and physical properties, as will be known to those of skill in the art. Examples of materials and selection criteria are described, for example, in *The Biomedical Engineering Handbook* (Second Edition, Volume I, J. D. Bronzino, Ed., Copyright 2000, CRC Press LLC, pp. IV-1-43-22). Manufacturing techniques may include injection molding, extrusion, die-cutting, rapid-prototyping, etc., and will depend on the choice of material and device size and configuration. Sensing and energy-emitting portions of the devices as well as associated control circuitry may be fabricated on the structural elements using various microfabrication and/or MEMS techniques (see, e.g., U.S. Patent Applications 2005/0221529, 2005/0121411, 2005/0126916, and Nyitrai, et al. "Preparing Stents with Masking & Etching Technology" (2003) 26$^{th}$ International Spring Seminar on Electronics Technology pp. 321-324, IEEE), or may be constructed separately and subsequently assembled to the structural elements, as one or more distinct components. See also, U.S. Patent Applications 2007/0066939 and 2007/0225633.

The choice of structural element size and configuration appropriate for a device may be selected by a person of skill in the art. Configurations for structural elements include, but are not limited to, a substantially tubular structure, one or more lumens in fluid communication with the body lumen, and/or an adjustable diameter (see, e.g., U.S. patent application Ser. Nos. 11/403,230 and 11/645,357). Structural elements may have the form, for example, of a short cylinder, an annulus, a cylinder, and/or a spiral. A spiral structure is disclosed, for example, in Bezrouk et al, ("Temperature Characteristics of Nitinol Spiral Stents" (2005) Scripta Medica (BRNO) 78(4):219-226.

In illustrative embodiments, one or more structural elements of one or more devices may be substantially cylindrical, and hollow and tubular in configuration, with a single central opening, optionally allowing the exterior of the cylindrical structural element to contact and engage the wall of a vessel lumen, and the interior of the structural element (within the single central opening) to optionally form a fluid-contacting portion of the structural element. Optionally, one or more structural elements of one or more devices may be approximately hemi-spherical or hemi-ellipsoid, optionally allowing a portion of its cross-section to contact and/or engage the wall of a lumen without significantly and/or substantially obstructing the movement of fluid within the body lumen. Optionally, one or more structural elements of one or more devices may be pill- or capsule-shaped, and adapted to move through a central portion of a body lumen. Lumen wall engaging portions may include, but are not limited to, rotating wheels, projections (e.g. arms), springs, hooks (e.g. claws), suction cups, and/or tissue adhesives that are configured to engage wall portions and optionally to provide mobility to one or more devices.

In additional to materials disclosed above, flexible material having adjustable diameter, taper, and length properties may be used as part of the structural material. For example, some materials may change from a longer, narrower configuration, to a shorter, wider configuration, or may taper over their length. Structural elements that may exhibit this type of expansion/contraction property may include mesh structures formed of various metals or plastics, and some polymeric materials, for example (see, e.g., "Agile new plastics change shape with heat" MIT News Office (Nov. 20, 2006) pp. 1-4; MIT Tech Talk (Nov. 22, 2006) p. 5; http://web.mit.edu/newsoffice/2006/triple-shape.html; and Shanpoor et al., Smart Materials and Structures (2005) 14:197-214, Institute of Physics Publishing).

In some embodiments, the structural element may include a self-expanding material, a resilient material, or a mesh-like material. Flexibility may also be conferred by configuration as well as material; the structural element may include a slotted structure and/or mesh-like material, for example. Structural elements may be formed from various materials, including metals, polymers, fabrics, and various composite materials, including ones of either inorganic or organic character, the latter including materials of both biologic and abiologic origin, selected to provide suitable biocompatibility and mechanical properties. The structural element may include a biocompatible material, and may include a bioactive component (such as a drug releasing coating or bioactive material attached to or incorporated into the structural element).

Embodiments of one or more devices 100, 200, and/or 300 optionally include one or more insert 170 responsive to control circuitry 150 and configured to modulate at least part of a vessel lumen, optionally at least part of the circumference of the lumen. In some embodiments, one or more insert 170 is configured to controllably, reversibly, and/or programmably modulate at least part of the circumference of the vessel lumen. In illustrative embodiments, one or more insert 170 is configured to reduce the diameter of at lest part of a vessel lumen responsive to a signal from control circuitry 150 optionally once every 24 hours, or once a week, or once a month, or once a year, for example. In illustrative embodiments, one or more insert 170 is configured to modulate at least part of the diameter of a vessel lumen responsive to a signal from control circuitry 150 at a remote (e.g. external) location, optionally in response to a medical professional for screening and/or diagnosis.

In some embodiments, one or more insert 170 is configured to modulate (optionally narrow, constrict, compress, and/or occlude, or expand and/or enlarge) at least part of the inner (e.g. interior) circumference of the vessel lumen. In some embodiments, one or more insert 170 is configured to modulate (e.g. optionally constrict and/or compress, or expand and/or enlarge) at least part of the outer (e.g. exterior) circumference of the vessel lumen.

In some embodiments, one or more insert 170 is configured to narrow (e.g. compress and/or occlude) at least part of the lumen (e.g. the inner circumference and/or diameter) such that one or more cells traverse the constriction in approximately single file and/or such that one or more cells traverse a localized region. In some embodiments, one or more insert 170 is configured to constrict (e.g. compress and/or occlude) at least part of the lumen (e.g. inner circumference and/or diameter) such that fluid flow is modified and/or the movement of one or more cells (e.g. one or more possible targets and/or one or more targets) is decreased.

In illustrative embodiments, one or more insert 170 is configured to modify a vessel lumen such that one or more cells traverse a localized region, such that the cells pass through an imaging system. An imaging system may include one or more sensors 130, one or more energy sources 110 and/or control circuitry 150 optionally in association with the one or more insert 170. In illustrative embodiments, one or more insert 170 is configured to modify a vessel lumen such that one or more cells traverse a localized region responsive to control circuitry 150, optionally responsive to analysis of one or more image responses (e.g. optionally identifying one or more possible targets and/or one or more targets) from one or more sensors 130 upflow from the insert 170.

In some embodiments, one or more insert 170 is configured to function proximal to the vessel lumen. In some embodiments, one or more insert 170 is configured as a closable sleeve. In illustrative embodiments, one or more insert 170 at least partial surrounds the vessel wall, and optionally occludes fluid flow, by tightening around the vessel wall, optionally in discrete locations.

In some embodiments, one or more insert 170 is configured to function within the vessel lumen. In some embodiments, one or more insert 170 is configured as an expandable tube. In some embodiments, one or more insert 170 includes a movable valve. In illustrative embodiments, one or more insert 170 includes a valve that is open (e.g. not occluding fluid flow) until signaled by control circuitry 150 to partially or completely stop fluid flow. In illustrative embodiments, one or more insert includes an expandable tube, that when expanded optionally enlarges the outer circumference of the vessel wall and/or expands or narrows the inner circumference of the vessel wall.

In some embodiments, one or more insert 170 is placed upflow from at least one of the one or more sensors 130. In some embodiments, one or more insert 170 is placed downflow from at least one of the one or more sensors 130. In some embodiments, one or more insert includes at least one of the one or more sensors 130. In some embodiments, one or more sensors 130 are configured to capture one or more image responses within, downflow, and/or upflow of the insert modulated part of the vessel lumen. In illustrative embodiments, one or more insert 170 and one or more sensors 130 (and optionally one or more energy sources 110) are part of an imaging (and/or sensing) system. For example, an insert 170 may have one or more sensor 130 (and/or energy source 110) associated upflow, optionally to screen for potential targets, one or more sensor 130 (and/or energy source 110) positioned to detect images within the insert 130, and/or one or more sensors (and/or energy source 110) positioned to detect images downflow from the insert. The one or more energy sources 110 are also optionally configured to provide ablation energy to one or more targets.

In some embodiments, one or more insert 170 is placed upflow from at least one of the one or more energy sources 110. In some embodiments, one or more insert 170 is placed downflow from at least one of the one or more energy sources 110. In some embodiments, one or more insert includes at least one of the one or more energy sources 110. In some embodiments, one or more energy sources 110 are configured to function (optionally elicit one or more image responses and/or provide ablation energy) within, downflow, and/or upflow of the insert modulated part of the vessel lumen. In some embodiments, one or more energy sources 110 are placed upflow and/or downflow of the one or more insert.

As used herein, the term "fluid" may refer to liquids, gases, and other compositions, mixtures, or materials exhibiting fluid behavior. The fluid within the body lumen may include a liquid, or a gas or gaseous mixtures. As used herein, the term fluid may encompass liquids, gases, or mixtures thereof that also include solid particles in a fluid carrier. Liquids may include mixtures of two or more different liquids, solutions, slurries, or suspensions. As used herein, lumen-related fluid refers to, blood and/or lymph. Liquids present within vessel lumens may include synthetic or introduced liquids, such as blood substitutes, or drug, nutrient, fluorescent marker, or buffered saline solutions. Fluids may include liquids containing dissolved gases or gas bubbles, or gases containing fine liquid droplets or solid particles.

As used herein, the term "downflow" includes relative locations that are in the expected subsequent path of the fluid flow (e.g. the direction fluid is flowing towards). As used herein, the term "upflow" includes relative locations that are in the expected previous path of fluid flow (e.g. the direction fluid is flowing from).

Embodiments of one or more devices 100, 200, and/or 300 optionally include one or more vessel attachment units 180. Embodiments of one or more vessel attachment units 180 are discussed herein optionally in relation to the local bypass 210 and reservoirs 310 among others. In some embodiments, one or more vessel attachment units 180 may also be used for attaching systems and subparts of one or more devices 100, 200, and/or 300, optionally including energy sources 110, sensors 130, control circuitry 150, power sources 160, inserts 170, etc. proximal to a vessel wall. In illustrative embodiments, one or more vessel attachment unit 180 is configured to attach one or more insert 170 proximal to one or more vessel wall.

In illustrative embodiments, one or more vessel attachment units 180 include mechanisms configured to allow affixation to a vessel wall, either permanent or temporary. In illustrative embodiments, configurations for affixing may include, but are not limited to, one or more anchors configured to attach at least temporarily to a vessel wall, one or more hooks and/or claws, one or more adhesive materials and/or glues, one or more contracting elements, and/or one or more suction-generating elements. In illustrative embodiments, one or more vessel attachment units 180 include, but are not limited to, one or more of sleeves, straps, clamps, Velcro (e.g. geckel), snaps, links, sutures, pins, staples, and other appropriate medical closure devices.

Embodiments of one or more devices 100, 200, and/or 300 optionally include one or more vessel lumen anchors 190. Embodiments of one or more vessel lumen anchors 190 are discussed herein optionally in relation to the local bypass 210 and reservoirs 310 among others. In some embodiments, one or more vessel lumen anchors 190 may also be used for attaching systems and subparts of one or more devices 100, 200, and/or 300, optionally including energy sources 110, sensors 130, control circuitry 150, power sources 160, inserts 170, etc. within a vessel lumen. In illustrative embodiments, one or more vessel lumen anchors 190 are configured to attach one or more insert 170 within one or more vessel wall.

In illustrative embodiments, one or more vessel lumen anchors include mechanisms configured to allow affixation to a lumen wall, either permanent or temporary. In illustrative embodiments, configurations for affixing may include, but are not limited to, one or more anchors configured to attach at least temporarily to a wall of the lumen, one or more hooks and/or claws, one or more adhesive materials and/or glues, one or more expanding elements, and/or one or more suction-generating elements.

In some embodiments, one or more configurations for affixing one or more devices, in whole or in part, may be activated responsive to control circuitry 150. In some embodiments, one or more configurations for affixing one or more devices may be fixed or movable. Movable structures may include, but are not limited to, mechanical elements and/or materials that change shape or rigidity in response to temperature, electric field, magnetic field, or various other control signals. Affixation may be permanent, for extended periods, and/or temporary. As used herein, the term "extended periods" may include weeks to months to years and subsets thereof. As used herein, the term "temporary" may include seconds, to minutes, to hours, to days and subsets thereof.

Embodiments of one or more devices 200 include a local bypass 210 (see, e.g., FIG. 7 and FIG. 8) configured to function in, or proximal to, one or more blood vessel or lymph vessel. In some embodiments, at least one location in the local bypass lumen has a circumference and/or diameter such that one or more cells traverse the location in single file and/or traverse a localized region, optionally to facilitate sensing and/or ablation of one or more possible targets and/or one or more targets. In illustrative embodiments, the constriction in the bypass lumen is such that cells larger than a certain size cannot pass (e.g. cells larger than normal lymph cells and/or cells larger than normal constituents of the blood). In illustrative embodiments, the constriction in the bypass lumen is such that all cells can pass, but at a restricted velocity depending on size (e.g. cell deformation is required to allow passage of larger cells).

In illustrative embodiments, one or more local bypass 210 is configured to receive fluid flow (and/or cellular flow) from a vessel. The local bypass 210 is optionally configured for enhanced imaging and/or sensing of one or more targets (e.g. funneling cells through cooperative imaging and analysis units, optionally sequential imaging and/or sensing units), facilitating treatment, prevention, and/or diagnosis of one or more diseases and/or disorders. The local bypass 210 is optionally configured for enhanced ablation abilities, for example such that ablation energy is provided within a confined area surrounded by bypass lumen walls through which the energy does not penetrate (or does not penetrate to collaterally damage the subject).

The local bypass is optionally configured as a system optionally including, but not limited to, imaging and/or sensing systems (e.g. one or more energy source 110, one or more control circuitry 150, and/or one or more sensor 130), ablation systems (e.g. one or more energy source 110, one or more control circuitry 150, and/or one or more sensor 130), and/or attachment/insertion systems (e.g. one or more inserts 170, one or more bypass inserts 216, one or more vessel insertion units 214, one or more vessel lumen anchors 190, one or more vessel attachment units 180, etc.). In some embodiments, one or more of the systems are located within the local bypass 210. In some embodiments, one or more systems are configured to function upflow and or downflow of the local bypass 210, optionally in a cooperative manner with one or more systems within the local bypass 210. In some embodiments, the local bypass 210 is configured to function cooperatively with one or more device 100 and/or one or more device 300, and/or parts thereof.

In some embodiments, the local bypass 210 is configured to function in a vessel lumen (e.g. an intralumenal bypass 211), and is optionally configured with one or more vessel lumen anchors 190, one or more bypass inserts 216, and/or one or more closable openings 213 (e.g. one or more valves 215). In some embodiments, the local bypass 210 is configured to function proximal to a vessel lumen (e.g. an extralumenal bypass 212), and is optionally configured with at least one vessel attachment unit 180 at each end of the local bypass, one or more bypass insert 216, and/or one or more vessel insertion unit 214 optionally including one or more valves 215.

In some embodiments, one or more sensor 130 and/or one or more control circuitry 150 (and optionally components such as but not limited to one or more energy source 110, one or more power source 160) are separate from or external to the local bypass. In some embodiments, one or more sensor 130 and/or one or more control circuitry 150 (and optionally components such as but not limited to one or more energy source 110, one or more power source 160) are part of or internal to the local bypass. In some embodiments, there are one or more sensor 130 and/or one or more control circuitry 150 (and optionally components such as but not limited to one or more energy source 110, one or more power source 160) external to the local bypass as well as internal to the local bypass. Embodiments in which one or more parts of the device 200 are not attached to the local bypass 210, may also include one or more one or more insert 170, and/or one or more vessel attachment units 180, and/or one or more vessel lumen anchors 190.

Embodiments of the local bypass 210 are optionally configured with one or more bypass insert 216 responsive to control circuitry 150, and configured to modulate at least part of a local bypass lumen, optionally at least part of the inner (e.g. interior) and/or outer (e.g. exterior) circumference and/or diameter of the lumen. Embodiments discussed in relation to the insert 170 herein, are also applicable to the bypass insert 216 unless context dictates otherwise.

In illustrative embodiments, the one or more bypass insert 216 is an integral part of the local bypass 210, optionally an integral part of the intralumenal bypass 211 and/or the extralumenal bypass 212. In illustrative embodiments, the one or more bypass insert 216 is an attachable, insertable, and/or additional part associated with the local bypass 210. In some embodiments, one or more bypass insert 216 is configured as part of the interior of (and/or to function within) the bypass lumen. In some embodiments, one or more bypass insert 216 is configured as part of the exterior of (and/or to function externally to) the bypass lumen. In illustrative embodiments, one or more bypass insert includes a valve, optionally responsive to control circuitry.

In some embodiments, the one or more bypass insert 216 is configured to modulate fluid and/or cellular flow, optionally such that movement and/or velocity of one or more possible targets and/or one or more targets is decreased, and/or optionally increased. In illustrative embodiments, one or more bypass insert 216 is configured as one or more valves 215 within the lumen of the local bypass 210. For example, the one or more valves are configured to open to allow the influx of one or more possible targets and/or one or more targets, and then to close trapping the one or more possible targets and/or one or more targets in a target area and/or a detection area for ablation and/or further imaging and/or sensing, as appropriate.

In some embodiments, one or more bypass insert 216 is configured to narrow, compress, constrict, and/or occlude at least part of the bypass lumen. In some embodiments, one or more bypass insert 216 is configured to expand and/or enlarge at least part of the bypass lumen. In illustrative embodiments, one or more bypass insert 216 is configured including an expandable material configured to modulate the width of the inner circumference and/or diameter of the bypass lumen, optionally decreasing the diameter and/or circumference as the material expands. In illustrative embodiments, one or more bypass insert 216 is configured as a compression band that modulates the width of the bypass lumen optionally from the exterior of the local bypass 210. For example, the compression band is optionally configured with clamps and/or ratchets designed to tighten (and/or to loosen) responsive to control circuitry.

In some embodiments, one or more bypass insert 216 is configured to modulate at least part of the local bypass 210 at least partially based on one or more images captured by one or more sensors 130. In illustrative embodiments, one or more bypass inserts 216 constricts the bypass lumen trapping one or more targets for ablation, and/or one or more possible targets from further sensing. In some embodiments one or more bypass insert is configured to remotely, wirelessly and/or programmably modulate at least part of the bypass lumen. In illustrative embodiments, one or more bypass inserts 216 occludes a portion of the bypass lumen based on remote instructions from one or more external sources. In illustrative embodiments, one or more bypass inserts 216 occludes a portion of the bypass lumen based on a programmable protocol for sensing and ablation at predetermined intervals.

Embodiments of the extralumenal bypass 212 are optionally configured to function proximal to a blood vessel or lymph vessel lumen. In illustrative embodiments, the extralumenal bypass 212 is configured as a tubular structure optionally running parallel to the vessel and optionally including porous material. In illustrative embodiments, the extralumenal bypass 212 is configured with an enlarged cavity optionally including one or more sensors 130, one or more energy sources 110, and/or one or more power sources 160.

In some embodiments, the extralumenal bypass 212 is configured with one or more vessel insertion units 214, optionally responsive to control circuitry 150. In illustrative embodiments, one or more vessel insertion units 214 are configured to pierce the vessel wall to form an opening, optionally closable, through which fluid and/or cells may enter the extralumenal bypass 212, optionally by way of one or more valves 215. In illustrative embodiments, fluid flow into the bypass lumen is a passive process (e.g. the insertion sites are continually open), and/or an active process (e.g. the insertion sites must be opened and/or closed by an active mechanism). In illustrative embodiments, fluid flow and/or cells are optionally sucked into the local bypass through the one or more insertion units, and/or forced into the local bypass 210 through the insertion units. Mechanisms for providing suction and/or force are know in the art and/or described herein.

In illustrative embodiments, there is at least one vessel insertion unit 214 on each end of the extralumenal bypass 212, optionally configured such that fluid flows in at one end and out at the other end. In illustrative embodiments, the one or more vessel insertion units are configured such that fluid and/or cells enter the extralumenal bypass 212 through the downflow (in reference to the fluid flow in the vessel lumen) insertion site and exit the extralumenal bypass 212 through an upflow insertion site. Vessel insertion units 214 and methods for implanting such devices are known to those of skill in the art and/or are described herein.

In illustrative embodiments, some configurations of the extralumenal bypass 212 reduce fluid flow velocity including, but not limited to, increased length compared to the distance between insertion locations, baffling of local bypass lumen, changes in direction of the local bypass lumen, enlargement of the local bypass lumen as compared with the vessel lumen, and/or a path that is partly or completely opposite to the vessel fluid flow and/or gravity (e.g. fluid entry from the downflow insertion site and return via the upflow insertion site).

In some embodiments, the one or more vessel insertion units 214 are configured to modulate fluid flow to, from, and/or within the local bypass lumen (e.g. optionally through one or more valves 215), optionally at least partially based on one or more image responses captured by the one or more sensors 130, and optionally responsive to control circuitry 150. In illustrative embodiments, one or more valves 215 in the one or more vessel insertion units 214 are configured to control fluid flow (and/or cellular flow) into the local bypass lumen. The one or more valves are optionally configured to open responsive to control circuitry 150 based at least partially on the analysis of one or more image responses from one or more sensors 130 at least partially identifying one or more possible targets and/or one or more targets.

In illustrative embodiments, one or more valves 215 in the one or more vessel insertion units 214 are configured to control fluid flow (and/or cellular flow) out the local bypass lumen. The one or more valves are optionally configured to open responsive to control circuitry 150 based at least partially on the analysis of one or more image responses from one or more sensors 130 (optionally internal to the local bypass lumen) at least partially identifying one or more possible targets as not being one or more targets. The one or more valves are optionally configured to open responsive to control circuitry 150 following ablation (optionally within the local bypass lumen) of the one or more possible targets and/or one or more targets.

In illustrative embodiments, one or more valves 215 in the one or more vessel insertion units 214 are configured to control fluid flow (and/or cellular flow) within the local bypass lumen. The one or more valves 215 are optionally configured to open and/or close responsive to control circuitry 150 based at least partially on an analysis of the velocity of movement of one or more possible targets and/or one or more targets as they traverse the local bypass lumen. In illustrative embodiments, the one or more valves 215 are optionally closed to reduce the velocity and optionally one or more valves are opened to increase the velocity. In illustrative embodiments, one or more valves 215 are located internal to the local bypass lumen and are optionally configured to selectively stop fluid and/or cellular flow in one or more parts of the local bypass lumen. Selective modulation of fluid flow may be useful for enhanced imaging, functioning of one or more physiological sensors 140, and/or for ablation, optionally targeted ablation, among other reasons.

In some embodiments, the one or more vessel insertion units 214 and/or the one or more valves 215 are remotely controlled, wirelessly controlled, and/or programmable. In illustrative embodiments, the one or more vessel insertion units 214 are configured for remote control, optionally by the subject, and/or a medical professional such that the extralumenal bypass 212 is connected to the vessel via the one or more vessel insertion units 214 optionally at an appropriate monitoring time by the subject, and/or in the presence of a medical profession, optionally during a routine exam for example. In illustrative embodiments, the one or more valves 215 are configured as part of the one or more insertion units and remotely controlled by one or more external source, optionally the subject and/or a medical professional.

In illustrative embodiments, the one or more vessel insertion units 214 and/or one or more valves 215 are optionally programmed to insert in to the vessel wall and/or the one or more valves 215 to open and/or close at pre-determined intervals. In illustrative embodiments, the one or more vessel insertion units 214 and/or one or more valves 215 are optionally programmed to insert in to the vessel wall and/or the one or more valves 215 to open and/or close based at least partially on the occurrence of some event, optionally a measurable event such as sensing of one or more possible targets by the one or more sensors 130 and/or one or more possible diseases and/or disorders optionally be one or more physiological sensors 140.

Embodiments of the extralumenal bypass 212 are optionally configured with one or more vessel attachment unit 180. In some embodiments, the one or more vessel attachment unit 180 is configured to attach to the external vessel wall. In some embodiments, the one or more vessel attachment unit 180 is configured to at least partially surround an external circumference of a vessel. In some embodiments, the one or more vessel attachment unit 180 is configured as a mesh sleeve.

In illustrative embodiments, one or more vessel attachment unit 180 is configured to extend lengthwise down the extralumenal bypass 212 and concurrently lengthwise down the exterior wall of the vessel. In some embodiments, the one or more vessel attachments unit 180 is configured to attach responsive to control circuitry 150. In illustrative embodiments, the one or more vessel attachment unit 180 is configured to tighten and/or loosen based on control circuitry 150, optionally remotely controlled and/or programmably controlled.

In illustrative embodiments, one or more vessel attachment unit 180 is configured as optionally a series of intermittent connections between the extralumenal bypass 212 and the vessel wall. In illustrative embodiments, one or more vessel attachment unit 180 is configured to attach each end of the extralumenal bypass 212 to the vessel wall. In illustrative embodiments, one or more vessel attachment unit 180 is configured as part of and/or including the one or more vessel insertion units 214. In illustrative embodiments, the one or more vessel attachment unit 180 is configured to wrap partially and/or completely around the external vessel wall. In illustrative embodiments, the one or more vessel insertion units 214 are optionally configured to concomitantly and/or automatically pierce the vessel wall (e.g. during affixation).

In some embodiments, the one or more vessel attachment unit 180 is configured to include one or more vessel anchors and/or vessel clamps. In illustrative embodiments, the one or more vessel anchors optionally include one or more hooks and/or barbs optionally configured to catch into the external wall of the lumen, optionally without piercing through to the lumen. In illustrative embodiments, one or more vessel clamps are configured to connect part, or the entirety, of the vessel attachment unit 180 around the vessel wall. In illustrative embodiments, the one or more clamps are configured for optional tightening and/or loosening (e.g. for constricting and/or compressing the vessel lumen as well as attachment), optionally responsive to control circuitry 150. In some embodiments, one or more vessel clamps include one or more adhesives, optionally including geckel. Other mechanisms and devices for affixation and/or closure are known in the art and/or described herein.

In some embodiments, one or more vessel attachment unit 180 is configured to include one or more sensors 130 and/or one or more energy sources 110, optionally configured to align cooperatively during affixation of the vessel attachment unit 180 to the vessel wall. In some embodiments, one or more vessel attachment unit 180 is configured to include one or more energy sources 110, optionally configured to align to a target area during affixation of the vessel attachment unit 180 to the vessel wall.

In some embodiments, the extralumenal bypass 212 is configured with one or more bypass insert 216 responsive to control circuitry and configured to modulate at least part of the bypass lumen as described herein; those embodiments are also encompassed for the bypass insert 216 associated with the intralumenal bypass 211 unless context dictates otherwise.

Embodiments of the intralumenal bypass 211 are optionally configured to function in a blood vessel or lymph vessel lumen. In illustrative embodiments, an intralumenal bypass 211 is a roughly tubular shape sized for use within a vessel lumen, and optionally including mesh to allow passage of fluid while retaining cells, etc. In illustrative embodiments, an intralumenal bypass 211 is a roughly oblong shape sized for use within a vessel lumen, configured such that the length dimension is parallel to the length dimension of the vessel lumen, and optionally open at both ends (e.g. upflow and downflow). In illustrative embodiments, the intralumenal bypass 211 is configured from optically pure material optionally designed to enhance imaging and/or sensing. In illustrative embodiments, one or more intralumenal bypass 211 is configured such that ablation energy does not significantly penetrate the lumen wall.

In some embodiments, the intralumenal bypass 211 is configured with one or more vessel lumen anchors 190. In illustrative embodiments, one or more vessel lumen anchors 190, optionally hooks, are configured to affix the intralumenal bypass 211 to the internal wall of the vessel lumen. In some embodiments one or more vessel lumen anchors 190 are expandable braces that contact the lumen walls in opposition. In some embodiments, a combination of anchors may be used, for example, braces at one or more opening of the intralumenal bypass 211, and hooks along the exterior bypass wall. In illustrative embodiments, the intralumenal bypass 211 is affixed using geckel.

In some embodiments, the one or more vessel lumen anchors 190 are configured to attach to the vessel lumen responsive to control circuitry 150. In illustrative embodiments, the intralumenal bypass 211 is optionally configured to be placed in a vessel lumen using some form of microsurgery, optionally an endoscopic approach, where the vessel lumen anchors 190 are triggered to attach to the lumen wall remotely, wirelessly, and/or programmably. In illustrative embodiments, the vessel lumen anchors 190 can by controllably released to facilitate removal and/or repositioning of the intralumenal bypass 211.

In some embodiments, the intralumenal bypass 211 is configured with at least one closable opening 213 on an upflow end and/or downflow end of the intralumenal bypass 211. In some embodiments, the one or more closable openings 213 (e.g. one or more valves 215) are responsive to control circuitry 150 and are configured to modulate fluid flow to and/or from the local bypass lumen. In illustrative embodiments, the intralumenal bypass 211 is configured with closable openings 213 configured to allow fluid flow to enter one end, traverse the bypass lumen and exit another end. In illustrative embodiments, the closable openings 213 open and close based on a pre-programmed pattern, optionally to allow random sampling of cells in the fluid flow, and optionally the bypass lumen is configured to include one or more sensors 130 and/or energy sources 110.

In illustrative embodiments, the closable openings 213 open and close responsive to control circuitry 150 at least partially based on image responses captured by sensors 130 associated with one or more possible targets. For example, one or more sensors 130 and energy sources 110 are optionally cooperatively positioned upflow from the intralumenal bypass 211, and following analysis of one or more image responses by control circuitry 150 indicating the presence of one or more possible targets, one or more valves 215 in the upflow closable opening 213 open in response to the control circuitry 150 to allow entry of the one or more possible targets. One or more valves 215 in the downflow closable opening 213 optionally also sequentially close responsive to control circuitry 150 to temporarily trap the one or more possible targets in the bypass lumen. Optionally, additional image responses may be captured by the one or more sensors 130 (optionally different types or quality of sensors) and analyzed to determine whether the one or more possible targets are one or more targets. Optionally, ablation energy is provided to the bypass lumen to ablate the one or more possible targets and/or the one or more targets optionally in a target area.

In some embodiments, the extraluminal bypass 212 is configured with one or more bypass insert 216 responsive to control circuitry and configured to modulate at least part of the bypass lumen as described herein; those embodiments are also encompassed for the bypass insert 216 associated with the intralumenal bypass 211 unless context dictates otherwise.

Embodiments of one or more devices 300 include one or more reservoirs 310 (see e.g., FIG. 9 and FIG. 10) configured to receive one or more targets from, and to function in, or proximal to, one or more blood vessel or lymph vessel. In some embodiments, at least one location in the reservoir lumen has a circumference and/or diameter such that one or more cells traverse the location in single file and/or traverse a localized region, optionally to facilitate sensing and/or ablation of one or more possible targets and/or one or more targets. In illustrative embodiments, the constriction in the reservoir lumen is such that cells larger than a certain size cannot pass (e.g. cells larger than normal lymph cells and/or cells larger than normal constituents of the blood). In illustrative embodiments, the constriction in the reservoir lumen is such that all cells can pass, but optionally at a restricted velocity depending on size (e.g. cell deformation is required to allow passage of larger cells).

In some embodiments, one or more reservoirs 310 are configured to function in a vessel lumen (e.g. intralumenal reservoir 311), and optionally configured with one or more vessel lumen anchors 190, one or more self-sealing apertures 313, and/or one or more closable openings 213 optionally including one or more valves 215. In some embodiments, one or more reservoirs 310 are configured to function proximal to a vessel (e.g. extralumenal reservoir 312), and optionally configured with one or more vessel insertion units 214 (optionally including one or more valves 215), one or more vessel attachment units 180, and/or one or more self-sealing apertures 313.

In some embodiments, one or more sensor 130 and/or one or more control circuitry 150 (and optionally components such as, but not limited to, one or more energy source 110, one or more power source 160, and/or one or more local bypass 210) are separate from and/or external to the one or more reservoirs 310. In some embodiments, one or more sensor 130 and/or one or more control circuitry 150 (and optionally components such as but not limited to one or more energy source 110, one or more power source 160, and/or one or more local bypass 210) are part of, or internal to, the one or more reservoirs 310. In some embodiments, there are one or more sensors 130 and/or one or more control circuitry 150 (and optionally components such as but not limited to one or more energy source 110, one or more power source 160, and/or one or more local bypass 210) external to the one or more reservoirs 310 as well as internal to the one or more reservoirs 310. Embodiments in which one or more parts of the device 300 are not attached and/or internal to the one or more reservoirs 310, may also include one or more of one or more insert 170, one or more vessel attachment units 180, and/or one or more vessel lumen anchors 190.

Embodiments of the one or more reservoirs 310 are optionally configured with one or more reservoir inserts responsive to control circuitry 150, and configured to modulate at least part of a reservoir lumen, optionally at least part of the inner (e.g. interior) and/or outer (e.g. exterior) circumference and/or diameter of the lumen. Embodiments discussed in relation to the insert 170 and/or bypass insert 216 herein, are also applicable to the reservoir insert, unless context dictates otherwise.

Embodiments of the one or more reservoirs 310 are optionally configured with one or more closable openings 213 configured such that one or more of the one or more closable openings are externally accessible following implantation in the subject. In illustrative embodiments, the one or more reservoirs 310 are configured to be accessed externally, optionally by the subject and/or by a medical professional. In illustrative embodiments, the one or more reservoir 310 is accessible via a large bore needle and/or via a portal configured for placement such that access is close to the skin surface and/or the portal is able to be palpated to determine the entry point. In illustrative embodiments, the location of the access portal may be identified through X-ray technology, MRI, imaging, or other methods known in the art. In illustrative embodiments, the one or more reservoir 310 is accessible via microsurgery, optionally through endoscopy or other appropriate medical procedure. Methods of access are known to those of skill in the art.

In some embodiments, one or more of the one or more closable openings 213 and/or valves 215 are self-sealing (e.g. self-sealing aperture 313). In illustrative embodiments, one or more reservoir 310 is configured with a self-sealing aperture 313 optionally positioned to be accessible externally following placement in a subject. Self-sealing apertures 313 are known in the art, for example as used as part of the multiple use seal for dispensing fluid pharmaceuticals from a vial. Self-sealing apertures 313 are optionally configured to allow penetration of a needle (e.g. a syringe needle and/or biopsy needle), withdrawal of part or all of the contents of the reservoir 310 and/or one or more compartments of the reservoir, and then to reseal (e.g. such that cells and/or fluid cannot escape) following withdrawal of the needle from the aperture.

Embodiments of one or more device 300 my optionally include one or more local bypass 210. For example, although embodiments of the one or more device 300 are described as they relate to one or more blood vessel and/or lymph vessel, these embodiments are also applicable to the one or more device 300 in association with the local bypass 210, unless context dictates otherwise. In some embodiments, the one or more reservoir 310 is configured as an integral part of one or more local bypass 210, optionally intralumenal or extralumenal. In some embodiments, the one or more reservoir 310 is configured as an additional part of the local bypass 210, optionally attachable externally and/or internally. In some embodiments, the one or more reservoir 310 is configured as part of a system including the one or more local bypass 210.

In illustrative embodiments, the local bypass 210 is configured to receive fluid flow from a vessel lumen, which fluid passes through a sensing system (optionally including one or more energy source 110, one or more sensors 130, one or more control circuitry 150, and/or one or more bypass insert 216) configured to identify one or more targets and/or possible targets, and then to one or more reservoirs or reservoir compartments optionally through one or more closable openings 213 and/or valves 215.

Embodiments of the one or more reservoirs 310 are optionally configured with one or more compartments within the one or more reservoirs 310. In some embodiments, one or more reservoir inserts optionally including one or more valves 215 direct fluid and/or cellular flow to one or more of the compartments optionally based on control circuitry 150. In illustrative embodiments, one or more targets and/or one or more possible targets are directed to different compartment at least partially based on space availability and/or at least partially based on the time of collection, for example. In some embodiments, one or more reservoir inserts, optionally including one or more valves 215, direct fluid and/or cellular flow to one or more of the compartments optionally at least partially based on analysis by control circuitry 150 of one or more image responses captured by one or more sensors 130.

In illustrative embodiments, one or more possible targets and/or one or more targets are segregated into one or more different compartments depending on one or more criteria, optionally disease and/or disorder associated criteria. For example, putatively cancerous cells may be directed to one compartment and putatively infectious agents may be directed to another compartment. The one or more compartments may be configured for additional analysis of the one or more putative targets by one or more sensing systems (optionally including one or more energy sources 110, one or more sensors 130 and one or more control circuitry 150).

Embodiments of the extralumenal reservoir 312 are optionally configured to function proximal to a blood vessel and/or lymph vessel lumen. In illustrative embodiments, the extralumenal reservoir 312 is configured as a roughly bag-like structure, optionally including porous and/or mesh-like material. In illustrative embodiments, the extralumenal reservoir 312 is configured as an expandable structure, optionally including a reservoir relief valve (e.g. purge valve) optionally configured for releasing excess pressure, and/or fluid (optionally cellular) flow, optionally following at least partial ablation and/or modification of one or more targets and/or possible targets. In illustrative embodiments, at least part of the reservoir is configured for enhanced imaging and/or sensing. In illustrative embodiments, at least part of the reservoir is configured for ablation, optionally with limited collateral damage to surrounding subject tissues. In illustrative embodiments, the extralumenal reservoir 312 is configured with one or more cavity optionally including one or more sensors 130, one or more energy sources 110, one or more reservoir inserts, and/or one or more power sources 160.

In some embodiments, the extralumenal reservoir 312 is configured with one or more vessel insertion units 214, optionally responsive to control circuitry 150. Embodiments of the one or more vessel insertion units 214 discussed in relation to the extralumenal bypass 212 herein, are also applicable to the extralumenal reservoir 312, unless context dictates otherwise.

In illustrative embodiments, one or more extralumenal reservoirs 312 are configured with one vessel insertion unit 214 configured such that fluid (and/or cells) from a vessel lumen flow in to the one or more extralumenal reservoirs 312. In some embodiments, the one or more vessel insertion units 214 are configured to modulate fluid flow to, from, and/or within the reservoir lumen (e.g. optionally through one or more valves 215), optionally at least partially based on one or more image responses captured by the one or more sensors 130, and optionally responsive to control circuitry 150.

In illustrative embodiments, one or more valves 215 in the one or more vessel insertion units 214 are configured to control fluid flow (and/or cellular flow) into the reservoir lumen. The one or more valves are optionally configured to open responsive to control circuitry 150 based at least partially on the analysis of one or more image responses from sensing systems (optionally including one or more sensors 130, one or more coordinating energy sources 110, and one or more control circuitry 150), and optionally external to the extralumenal reservoir 312 and/or configured to image the vessel lumen) at least partially identifying one or more possible targets and/or one or more targets.

In illustrative embodiments, the one or more vessel insertion units 214 and/or valves 215 are configured to be programmable, optionally remotely and/or wirelessly, optionally to screen for the presence and/or absence of one or more targets, and/or to count numbers of one or more targets. In illustrative embodiments, the one or more sensing systems are configured remotely (by the subject and/or a medical professional) to detect image responses associated with one or more diseases or disorders for which the subject is considered at risk (e.g. due to genetics, health care, lifestyle, and/or symptoms) and to trigger the one or more valves 215 to open in the presence of one or more possible targets, and/or to open at designated sensing times (e.g. hourly, 2× per day, 4× per day, daily, weekly, monthly, etc.).

Embodiments of the extralumenal reservoir 312 are optionally configured with one or more vessel attachment unit 180. Embodiments of the one or more vessel attachment units 180 discussed herein, optionally in relation to the extralumenal bypass 212, are also applicable to the extralumenal reservoir 312, unless context dictates otherwise.

Embodiments of the extralumenal reservoir 312 are optionally configured with one or more reservoir insert responsive to control circuitry and configured to modulate at least part of the reservoir lumen. Embodiments of the one or more inserts 170 and/or one or more bypass inserts 216 discussed herein, are also applicable to one or more reservoir inserts in the extralumenal reservoir 312, unless context dictates otherwise.

Embodiments of the intralumenal reservoir 311 are optionally configured to function in a blood vessel or lymph vessel lumen. In illustrative embodiments, an intralumenal reservoir 311 is a roughly tubular shape sized for use within a vessel lumen, and optionally including mesh to allow passage of fluid while retaining cells, etc. In illustrative embodiments, an intralumenal reservoir 311 is a roughly oblong shape sized for use within a vessel lumen, configured such that the length dimension is parallel to the length dimension of the vessel lumen, and optionally includes one or more relief valve (e.g. pressure relief valve and/or fluid (cellular) flow release valve, optionally following ablation). In illustrative embodiments, the intralumenal reservoir is configured for enhanced sensing and/or imaging, and is designed to quantify numbers of targets, and/or percentages of targets based on control circuitry.

In some embodiments, the intralumenal reservoir 311 is configured with one or more vessel lumen anchors 190 optionally associated with one or more vessel insertion units 214 and/or one or more sensing systems. Embodiments of the one or more vessel lumen anchors 190 discussed herein are also applicable to one or more intralumenal reservoirs 311, unless context dictates otherwise.

Embodiments of the intralumenal reservoir 311 are configured with at least one closable opening 213 and/or one or more valves 215 providing a conduit from the vessel lumen to the reservoir lumen. In some embodiments, one or more closable opening is configured to be located on an upflow part of the reservoir 310. In some embodiments, one or more closable opening is configured to be located on a downflow part of the reservoir 310. Embodiments of the one or more closable opening 213 and/or one or more valves 215 discussed herein are also applicable to one or more intralumenal reservoirs 311, unless context dictates otherwise.

In illustrative embodiments, the intralumenal reservoir 311 is configured with closable openings 213 configured to allow fluid flow or optionally cellular flow to enter, optionally flow pass one or more sensing systems, and then enter one or more reservoir compartments optionally for storage, be ablated, and/or pass through another closable opening back into the subject. In illustrative embodiments, the closable openings 213 open and close to selectively receive and/or contain one or more identified targets.

In some embodiments, the intralumenal reservoir 311 is configured with one or more reservoir insert responsive to control circuitry and configured to modulate at least part of the reservoir lumen. Embodiments described for one or more insert 170 and/or one or more bypass insert 216 also encompassed for the reservoir insert associated with the intralumenal reservoir 311, unless context dictates otherwise.

It is contemplated that components, such as energy sources 110, sensors 130, control circuitry 150, and/or power sources 160, for example, will optionally be attached, connected to, place within, manufactured on or in, and/or formed integrally with one or more structural element. Methods for manufacture and/or assembly are known in the art and/or described herein.

Figure 2:
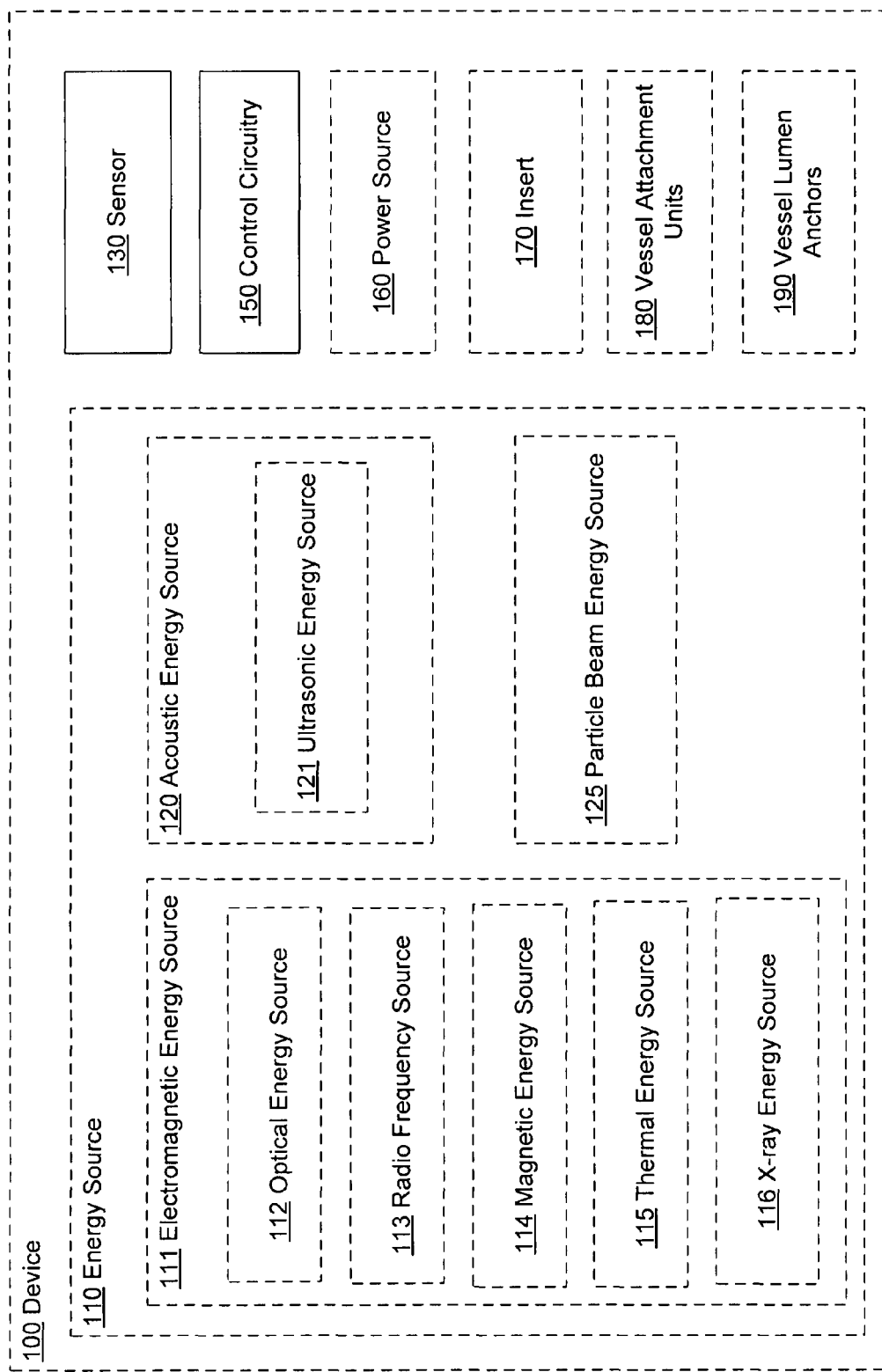
FIG. 2 shows a schematic of illustrative embodiments of the device of FIG. 1, with illustrative examples of an energy source.
Figure 3:
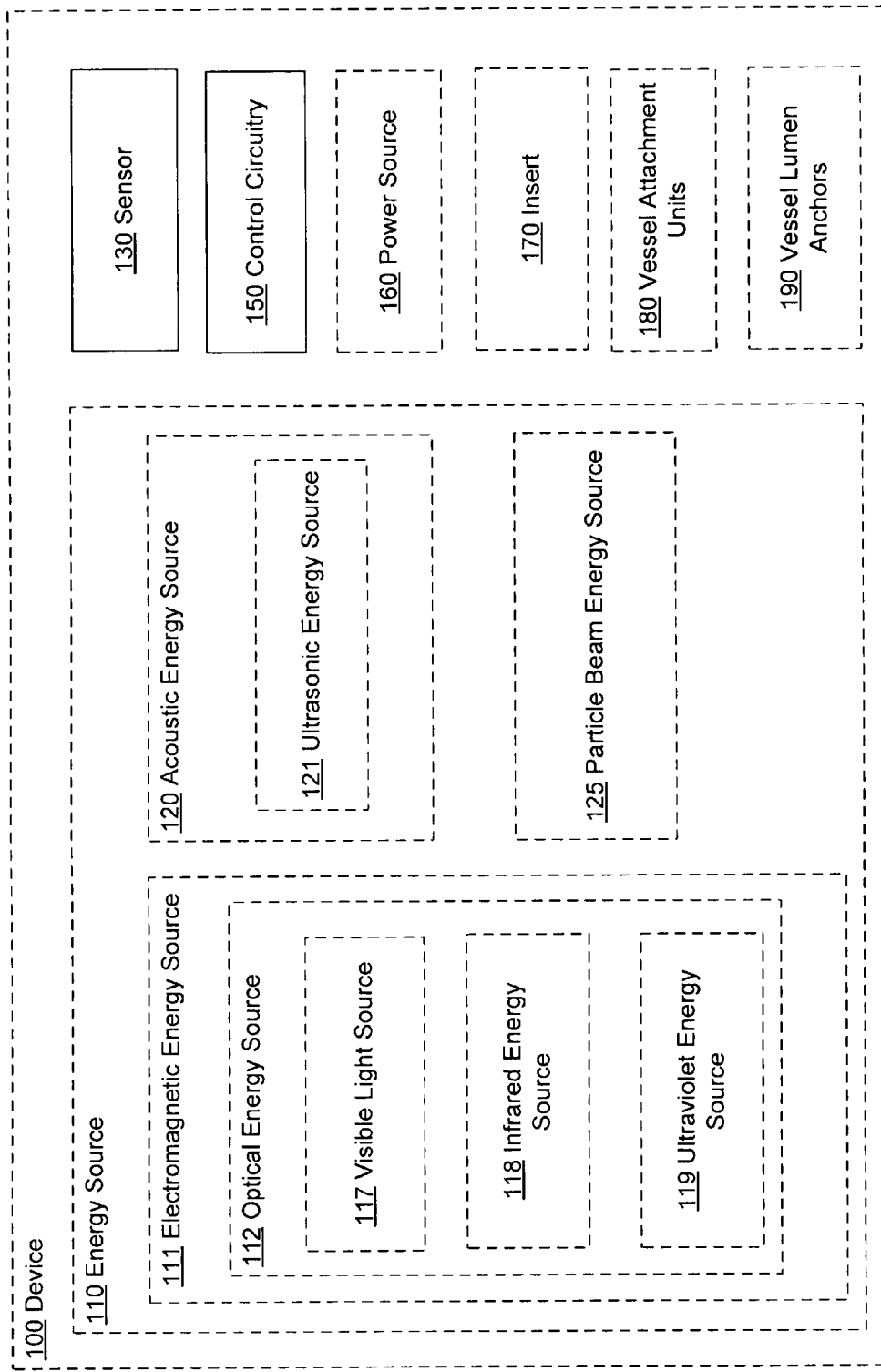
FIG. 3 shows a schematic of illustrative embodiments of the device of FIG. 1, with illustrative examples of an optical energy source.

Embodiments of one or more device 100, 200, and/or 300 may include one or more energy sources 110 (see e.g. FIG. 2 and FIG. 3). In some embodiments, one or more device 100 may include a first energy source configured to function in, or proximal to, one or more blood vessel or lymph vessel, and to provide energy configured to elicit one or more image responses associated with one or more blood vessel or lymph vessel; and one or more second energy source responsive to control circuitry and configured to provide ablation energy to a target area during the expected transit time of one or more targets through the target area.

In some embodiments, one or more device 200 may optionally include a first energy source configured to function in, or proximal to, a local bypass lumen, and to provide energy configured to elicit one or more image responses associated with a local bypass lumen; and optionally one or more second energy source responsive to control circuitry and configured to provide ablation energy to a target area during the expected transit time of one or more targets through the target area. In some embodiments, the first energy source 110 is configured to provide energy to elicit one or more image responses associated with fluid (and/or cellular) flow in, or proximal to (optionally upflow and/or downflow), the local bypass 210. In some embodiments, the first energy source 110 is configured to provide energy to elicit one or more image responses associated with fluid flow in the local bypass lumen. In some embodiments, the second energy source 110 is configured to emit ablation energy within, or proximal to, the local bypass 210, optionally with the local bypass lumen.

In some embodiments, one or more device 300 may include a first energy source configured to function in, or proximal to, one or more reservoirs, and to provide energy configured to elicit one or more image responses associated with the one or more reservoirs; and optionally one or more second energy source responsive to control circuitry and configured to provide ablation energy to a target area during the expected transit time of one or more targets through the target area. In some embodiments, the first energy source 110 is configured to provide energy to elicit one or more image responses associated with fluid (and/or cellular) flow in, or proximal to (optionally upflow and/or downflow), the one or more reservoirs 310. In some embodiments, the first energy source 110 is configured to provide energy to elicit one or more image responses associated with fluid flow in the lumen of the one or more reservoirs 310. In some embodiments, the second energy source 110 is configured to emit ablation energy within, or proximal to, the one or more reservoirs 310, optionally within the lumen of the one or more reservoirs. In some embodiments, the target area is in the lumen of a blood and/or lymph vessel, upflow and/or downflow of one or more reservoirs, and/or in the reservoir lumen.

One or more energy sources 110 may include, but are not limited to, one or more electromagnetic energy sources 111, one or more acoustic energy sources 120 (e.g. one or more ultrasonic energy sources 121), and/or one or more charged particle energy sources 125. One or more electromagnetic energy sources 111 may include, but are not limited to, one or more optical energy sources 112, one or more radio frequency sources 113, one or more magnetic energy sources 114, one or more thermal energy sources 115, and/or one or more X-ray energy sources 116. One or more optical energy sources 112 may include, but are not limited to, one or more visual energy sources 117, infrared energy sources 118, and/or one or more ultraviolet energy sources 119. In some embodiments, one or more energy sources described herein and/or known in the art may be specifically excluded, e.g. one or more electromagnetic energy source not including one or more X-ray energy source. In some embodiments one or more electromagnetic energy source 111 is one or more laser. In some embodiments, the optical energy is provided through fiber optic lines and/or a web of fiber optic lines. In some embodiments, one or more energy sources 110 are programmable, remote-controlled, wirelessly controlled, and or feedback-controlled.

One or more energy sources 110 (e.g. electromagnetic 111 and/or acoustic 120) are configured to elicit one or more image responses such as, but not limited to, electromagnetic image responses including, but not limited to, optical image responses (e.g. visible light image responses, infrared image responses, ultraviolet image responses, and/or fluorescent image responses, among others), radiofrequency image responses, and/or magnetic image responses. One or more energy sources 110 are configured to elicit one or more image responses including a scattering response and/or an absorptive response from the one or more targets. One or more image responses may include, but are not limited to, acoustic image responses, such as, but not limited to, ultrasonic image responses. One or more image responses may include, but are not limited to, thermal image responses, and/or color image responses. One or more image responses may include, but are not limited to, light scatter and/or light absorption. Characteristics of the energy appropriate for generating one or more image responses are known in the art and/or described herein.

One or more energy sources 110 (e.g. electromagnetic 111, acoustic 120 and/or particle beam 125) are configured to provide ablation energy to one or more targets or to a target area. In some embodiments, the electromagnetic energy source is an optical energy source and/or an X-ray energy source. In some embodiments, the electromagnetic energy is provided by one or more lasers. In some embodiments, one or more energy source 110 is configured to function within the one or more blood vessel and/or lymph vessel. In some embodiments, one or more energy source 110 is configured to function proximal to the one or more blood vessel and/or lymph vessel.

In some embodiments, different energy sources 110 provide energy to elicit an image response and to ablate one or more targets. In some embodiments, one energy source 110 provides energy to elicit an image response and to ablate one or more targets. In some embodiments, more than one energy source 110 provides energy to elicit an image response. In some embodiments, more than one energy source provides energy to ablate one or more targets. In some embodiments, a first energy source and a second energy source are the same energy source. In some embodiments, one or more of the one or more second energy source is separate from the one or more first energy source and/or the one or more sensors.

As used herein, the term "electromagnetic energy" may include, but is not limited to, radio waves, microwaves, terahertz radiation, infrared radiation, visible light, X-rays, and gamma rays. In some embodiments, one or more of these frequencies may be explicitly excluded from the general category of electromagnetic energy (e.g. electromagnetic energy sources, but not including X-ray energy sources). Electromagnetic energy (or radiation) with a wavelength between approximately 400 nm and 700 nm is detected by the human eye and perceived as visible light. Optical light may also include near infrared (longer than 700 nm) and ultraviolet (shorter than 400 nm).

As used herein, the term "charged particle" may include particles generated using one or more particle beams. A particle beam is optionally an accelerated stream of charged particles or atoms that may be directed by magnets and focused by electrostatic lenses, although they may also be self-focusing. Particle beams may be high energy beams (e.g. created in particle accelerators), medium and/or low energy beams.

Electromagnetic or optical energy is made up of photons. Electromagnetic energy includes, but is not limited to, single photon electromagnetic energy, two photon electromagnetic energy, multiple wavelength electromagnetic energy, and extended-spectrum electromagnetic energy. Electromagnetic energy may be used for eliciting image responses and/or for ablation of one or more targets.

As used herein, the term "fluorescence" may include the production of light (emission) following excitation by electromagnetic energy. Fluorescence may result from an inherent response of one or more targets to excitation with electromagnetic energy. As used herein, the term "autofluorescence" may include an inherent fluorescent response from one or more targets.

Electromagnetic energy sources 111 may be configured to emit energy as a continuous beam or as a train of short pulses. In the continuous wave mode of operation, the output is relatively consistent with respect to time. In the pulsed mode of operation, the output varies with respect to time, optionally having alternating 'on' and 'off' periods. In illustrative examples, one or more energy sources are configured to emit pulsed energy to specifically ablate a limited area and/or a limited number of target cells. In illustrative examples, one or more energy sources are configured to emit continuous energy to excite endogenous fluorophores to emit fluorescence.

One or more electromagnetic energy sources 111 may include one or more lasers having one or more of a continuous or pulsed mode of action. One or more pulsed lasers may include, but are not limited to, Q-switched lasers, mode locking lasers, and pulsed-pumping lasers. Mode locked lasers emit extremely short pulses on the order of tens of picoseconds down to less than 10 femtoseconds, the pulses optionally separated by the time that a pulse takes to complete one round trip in the resonator cavity. Due to the Fourier limit, a pulse of such short temporal length may have a spectrum which contains a wide range of wavelengths.

In some embodiments, the energy (optionally electromagnetic) is focused at a depth of approximately 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm within a vessel lumen, a bypass lumen, and/or a reservoir. In some embodiments, the electromagnetic energy is focused at a depth of approximately 0.1 to 3 mm, 0.1 to 2.5 mm, 0.1 to 2.0 mm, 0.1 to 1.5 mm, 0.1 to 1.0 mm, 0.1 to 0.5 mm, 0.5 to 3.0 mm, 0.5 to 2.5 mm, 0.5 to 2.0 mm, 0.5 to 1.5 mm, 0.5 to 1.0 mm, 1.0 to 3.0 mm, 1.0 to 2.5 mm, 1.0 to 2.0 mm, 1.0 to 1.5 mm, 1.5 to 3.0 mm, 1.5 to 2.5 mm, 1.5 to 2.0 mm, 2.0 to 3.0 mm, 2.0 to 2.5 mm, or 2.5 to 3.0 mm within a vessel lumen, a bypass lumen, and/or a reservoir.

In some embodiments, the electromagnetic energy is generated by two photons having the same wavelength. In some embodiments, the electromagnetic energy is generated by two photons having a different wavelength. Electromagnetic energy generated by two photons is optionally focused at a depth within a vessel lumen, a bypass lumen, and/or a reservoir, optionally at one or more depths as described above and/or herein.

As used herein, the term "two-photon" may include excitation of a fluorophore by two photons in a quantum event, resulting in the emission of a fluorescence photon, optionally at a higher energy than either of the two excitatory photons, optionally using a femtosecond laser. In some embodiments, two photon electromagnetic energy is coupled through a virtual energy level and/or coupled through an intermediate energy level.

As used herein, the term "extended-spectrum" may include a range of possible electromagnetic radiation wavelengths within the full spectrum of possible wavelengths, optionally from extremely long to extremely short. One of skill in the art is able to select appropriate ranges for the devices and methods disclosed herein based on information publicly available and/or disclosed herein.

In some embodiments, the energy (optionally electromagnetic) may be defined spatially and/or directionally. In some embodiments, the electromagnetic energy may be spatially limited, optionally spatially focused and/or spatially collimated. In illustrative embodiments, the electromagnetic energy optionally contacts less than less than an entire possible area, or an entire possible target, and/or is limited to a certain depth within a vessel lumen, a bypass lumen, and/or a reservoir.

In some embodiments, the energy (optionally electromagnetic) may be directionally limited, directionally varied, and/or directionally variable. In illustrative embodiments, the energy may be provided only in a single direction, for example 90 degrees from the horizontal axis of a device, or toward a lumen wall, a bypass wall, and/or a reservoir wall. In illustrative embodiments, the energy may be provided over a range of directions for example, through movement of the energy source 110, through movement of the entire device, and/or through illumination from a variety of energy sources 110 in the device.

Electromagnetic energy and/or acoustic energy configured to induce an image response in a target may be selected, optionally manually, remotely, programmably, wirelessly, and/or using feedback information. Frequencies that induce an image response in one or more targets are known in the art and/or discussed herein. In some embodiments, selection of excitation energy may be performed in advance, or as a result of information received, optionally including feedback information, optionally from one or more sensors 130 or provided by one or more external sources.

Electromagnetic energy, acoustic energy, and/or particle beam energy configured to ablate one or more targets may be selected, optionally manually, remotely, programmably, wirelessly, and/or using feedback information. Frequencies useful to at least partially ablate one or more targets are known in the art and/or discussed herein. In some embodiments, selection of ablation energy may be performed in advance, or as a result of information received, optionally including feedback information, optionally from one or more sensors 130 or provided by one or more external sources.

In addition to electromagnetic energy described herein, the ablation energy may be supplied by energetic charged particles, such as electrons, protons, or other ions. In one embodiment, the charged particles are directed towards the one or more targets and/or target area in the form of particle beams. In another embodiment, the charged particles are emitted over relatively wide solid-angles, and address the designated autofluorescent target by virtue of spatial proximity.

In one embodiment, particle beams are generated outside the body by beam generators such as particle accelerators, cathode ray tubes, electrostatic accelerators, voltage-multiplier accelerators, Cockcroft-Walton accelerators, Van de Graaff accelerators, Alvarez accelerators, linear accelerators, circular accelerators, wakefield accelerators, collimated radioactive emitters, etc. The beams from these sources can be directed towards the one or more targets and/or target area by mechanical, electrical, or magnetic methods. In some embodiments, the particle beams may be generated and directed from locations separate from the energy source 110 used to induce the image response. In other embodiments, the particle beam may be generated in proximity to the energy source for eliciting the image response, by using compact particle sources such as electrostatic accelerators, Alvarez accelerators, linear accelerators, voltage-multiplier accelerators, Cockcroft-Walton accelerators, wakefield accelerators, collimated radioactive emitters, etc.

In some embodiments, particle beams are generated and delivered from inside the body. Compact particle beam generators such as electrostatic accelerators, Alvarez accelerators, linear accelerators, voltage-multiplier accelerators, Cockcroft-Walton accelerators, or wakefield accelerators can be used. In one embodiment of a voltage-multiplier accelerator, the staged voltage elements can use high-field-strength capacitors. In another embodiment, the staged voltages can be generated in an array of photocells by photogeneration using on-board or off-board light sources. In another embodiment of an in-vivo particle source, a radioactive emitter can be used to provide a charged particle source. One example of such a source is the Beta-Cath™ System, developed by Novoste Corp.

In one embodiment, in-vivo radioactive sources can be encapsulated within shielding which can be used to control charged particle exposure to nearby tissue. The shielding can have one or more portals, allowing for collimated emission. The shielding can be movable, either across all or part of its extent, or across one or more portal openings, in order to provide switchable particle sources. Shielding can be controllably moved by mechanical techniques such as valves, shutters, or similar devices, can utilize movable liquids, such as Hg, or utilize other methods. The particles from these in-vivo sources can be directed towards the one or more targets and/or target area by mechanical, electrical, or magnetic methods, or may rely upon proximity.

Figure 4:
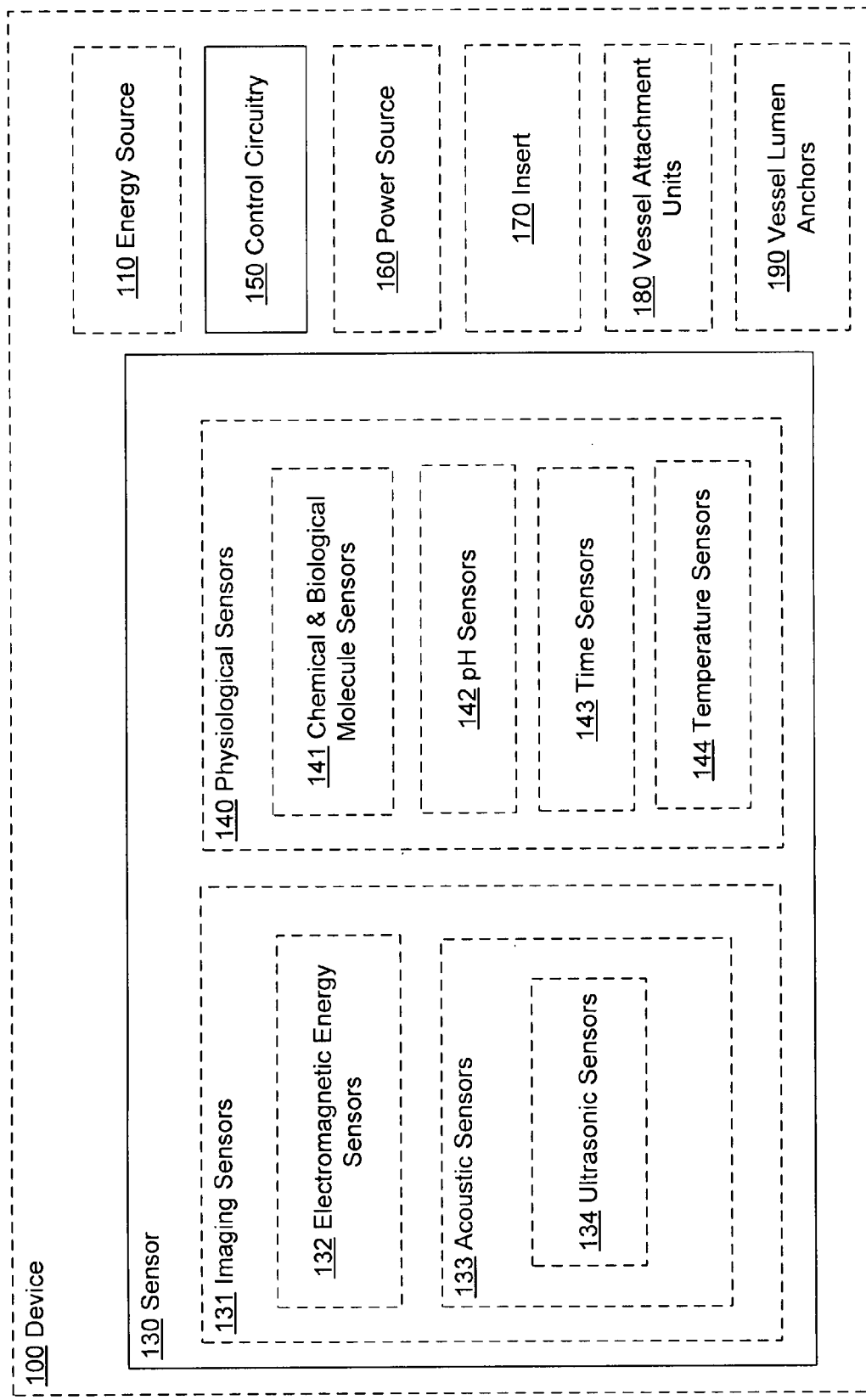
FIG. 4 shows a schematic of illustrative embodiments of the device of FIG. 1, with illustrative examples of a sensor.
Figure 5:
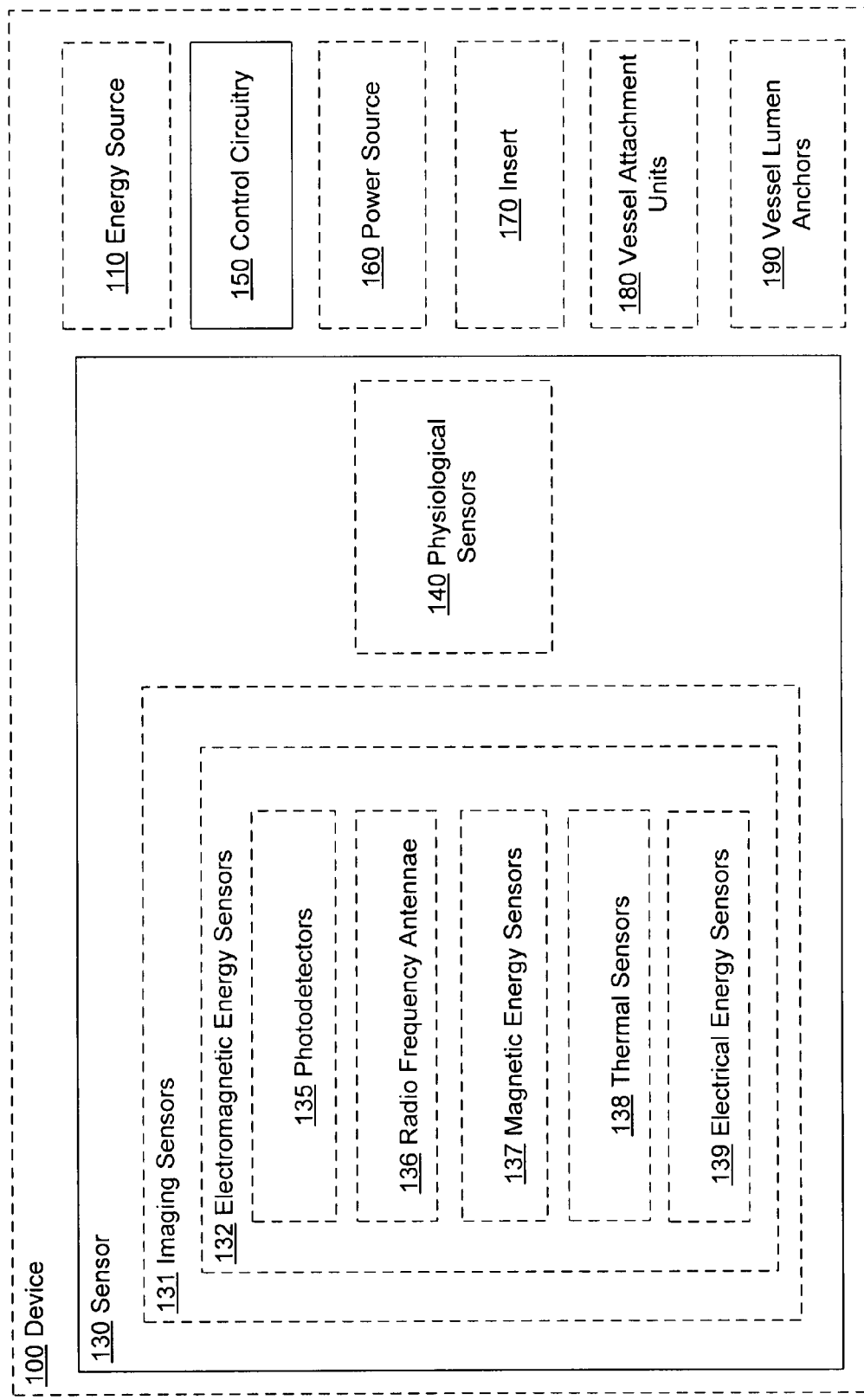
FIG. 5 shows a schematic of illustrative embodiments of the device of FIG. 1, with illustrative examples of an electromagnetic energy sensor.

Embodiments of one or more devices 100, 200, and/or 300 include one or more sensors 130 (see, e.g., FIG. 4 and FIG. 5). In some embodiments, one or more sensors 130 are the same sensor. In some embodiments, one or more sensors 130 are different sensors. In some embodiments, one or more sensors are in the same unit and/or are physically connected. In some embodiments, one or more sensors 130 are in separate units and/or not physically connected. In some embodiments, one or more sensors 130 are in the same and/or different units than one or more energy sources 110. In some embodiments, the one or more sensors 130 are configured to align with the one or more energy sources 110 and cooperatively elicit and capture image responses. In some embodiments, the one or more sensors 130 are configured to orient to the one or more energy sources 110 to cooperatively elicit and capture image responses. One or more sensors 130 may include, but are not limited to, one or more imaging sensors 131 and/or one or more physiological sensors 140.

Embodiments of one or more device 200 include one or more sensors 130 configured to function in, or proximal to, a local bypass 210, optionally the local bypass lumen. In some embodiments, the one or more sensors 130 are configured to capture one or more image responses associated with fluid (and/or cellular) flow in, or proximal to (optionally upflow and/or downflow), the local bypass 210. In some embodiments, the one or more sensors 130 are configured to capture one or more image responses associated with fluid (and/or cellular) flow in the local bypass lumen.

Embodiments of one or more devices 100, 200, and/or 300 include more then one sensor 130, optionally several sensors of the same or different types, optionally configured to function independently and/or in sequentially. In illustrative examples, one or more device 200 includes one or more sensors 130 upflow (e.g. in the vessel lumen) from the local bypass 210 (optionally configured to identify one or more possible targets for entry into the local bypass 210), one or more sensors within the local bypass lumen optionally configured to further image the one or more possible targets, one or more sensors 130 configured to capture images associated with ablation energy and modification of the one or more possible targets and/or one or more targets, and/or one or more sensors 130 downflow (e.g. configured to image the fluid flow re-entering the vessel lumen) from the local bypass 210.

In illustrative examples, one or more device 300 includes one or more sensors 130 upflow (e.g. in the vessel lumen)

from the reservoir 310 (optionally configured to identify one or more possible targets for entry into the reservoir 310), one or more sensors within the reservoir lumen optionally configured to further image the one or more possible targets, one or more sensors 130 configured to capture images associated with ablation energy and modification of the one or more possible targets and/or one or more targets, and/or one or more sensors 130 downflow (e.g. configured to image the fluid flow re-entering the vessel lumen) from the reservoir 310. In some embodiments, the detection area is in the one or more reservoirs 310, upflow and/or downflow from the one or more reservoirs 310, proximal to the one or more reservoirs 310, proximal to the one or more blood and/or lymph vessels, and/or in a vessel lumen.

One or more imaging sensors 131 may include, but are not limited to, one or more electromagnetic energy sensors 132 and/or one or more acoustic sensors 133 (e.g. ultrasonic sensors 134). One or more electromagnetic energy sensors 132 may include, but are not limited to, one or more photodetectors 135, one or more radiofrequency antennae 136, one or more magnetic energy sensors 137, one or more thermal sensors 138, and/or one or more electrical energy sensors 139. One or more electromagnetic energy sensors 132 may include one or more optical sensors such as, but not limited to, sensors configured to detect near IR, UV, fluorescence, and/or visual light.

One or more imaging sensors may include, but are not limited to, charge-coupled device cameras and/or complementary metal oxide semiconductor (CMOS) cameras. One or more imaging sensors may include, but are not limited to, one or more piezo transducers, one or more MEMS devices, one or more cavity resonators, one or more magneto resistive sensors, one or more magnetic field sensors, and/or one or more thermal sensors.

One or more physiological sensors 140 may include, but are not limited to, one or more chemical and/or biological molecule sensors 141 (e.g. blood chemistry, chemical concentration, biosensors), one or more pH sensors 142, one or more time sensors 143 (e.g. timers, clocks), and/or one or more temperature sensors 144. One or more physiological detectors 140 may include, but are not limited to blood pressure detectors, pulse detectors, peristaltic action sensors, pressure sensors, flow sensors, viscosity sensors, and/or shear sensors.

One or more sensors may be configured to measure various parameters, including, but not limited to, the electrical resistivity of the fluid, the density or sound speed of the fluid, the pH, the osmolality, or the index of refraction of the fluid at least one wavelength. The selection of a suitable sensor for a particular application or use site is considered to be within the capability of a person having skill in the art. One or more of these and/or other sensing capabilities may be present in a single sensor or an array of sensors; sensing capabilities are not limited to a particular number or type of sensors.

One or more biosensors may detect materials including, but not limited to, a biological marker, an antibody, an antigen, a peptide, a polypeptide, a protein, a complex, a nucleic acid, a cell (and, in some cases, a cell of a particular type, e.g. by methods used in flow cytometry), a cellular component, an organelle, a gamete, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, or a tag. A biosensor may include an antibody or other binding molecule such as a receptor or ligand.

One or more sensors optionally include, in part or whole, a gas sensor such as an acoustic wave, chemiresistant, or piezoelectric sensors, or an electronic nose. One or more sensors are optionally small in size, for example a sensor or array that is a chemical sensor (Snow (2005) Science 307:1942-1945), a gas sensor (Hagleitner, et al. (2001) Nature 414:293-296), an electronic nose, and/or a nuclear magnetic resonance imager (Yusa (2005), Nature 434:1001-1005). Further examples of sensors are provided in The Biomedical Engineering Handbook, Second Edition, Volume I, J. D. Bronzino, Ed., Copyright 2000, CRC Press LLC, pp. V-1-51-9, and U.S. Pat. No. 6,802,811) and/or known in the art.

In some embodiments, one or more sensors 130 are configured to capture one or more image responses including, but not limited to, electromagnetic image responses including, but not limited to, optical image responses (e.g. visible light image responses, infrared image responses, ultraviolet image responses, and/or fluorescent image responses, among others), radiofrequency image responses, and/or magnetic image responses. One or more image responses may include, but are not limited to, acoustic image responses, such as, but not limited to, ultrasonic image responses. One or more image responses may include, but are not limited to, thermal image responses, and/or color image responses. In some embodiments, one or more sensors 130 are configured to capture one or more image responses at one or more wavelengths. In some embodiments, one or more image responses described herein and/or known in the art may be specifically excluded from an embodiment, e.g. image responses not including fluorescent image responses.

In some embodiments, one or more image responses include, but are not limited to, actual images of, for example, cells within the vessel lumen. In some embodiments, one or more image responses include image information such as cell shape, cell outline, and/or cell periphery, among others. In some embodiments, one or more image responses include image information such as intracellular shapes, intracellular outlines, and/or intracellular peripheries, among others. In some embodiments, one or more sensors 130 are configured to capture light scattering. In some embodiments, one or more sensors 130 are configured to capture fluid and/or cell velocity.

One or more electromagnetic energy sensors 132 may be configured to measure the absorption, emission, fluorescence, or phosphorescence of one or more targets. Such electromagnetic properties may be inherent properties of all or a portion of one or more targets (e.g. auto-fluorescence), or may be associated with materials added or introduced to the body, surface, lumen, interior, and/or fluid, such as tags or markers for one or more targets. One or more targets may include, but are not limited to, one or more cells.

In some embodiments, one or more sensors 130 are configured to detect a fluorescent response at a single wavelength of electromagnetic energy, at two wavelengths of electromagnetic energy, at multiple wavelengths of electromagnetic energy, or over extended-spectrum electromagnetic energy. In some embodiments, one or more sensors 130 are configured to detect excitation energy and/or ablation energy.

In some embodiments, one or more sensors 130 are configured to detect a cumulative (optionally fluorescent) response over a time interval. In some embodiments, one or more sensors 130 are configured to detect a (optionally fluorescent) response at a specific time interval and/or at a specific time. In some embodiments, one or more sensors 130 are configured to detect a time-dependent (optionally fluorescent) response. In illustrative embodiments, the cumulative response is determined over milliseconds, seconds, and/or minutes following excitation. In some embodiments, the response is detected over millisecond, second, and/or minute time intervals following excitation. In some embodiments, the response is detected approximately femtoseconds, picoseconds, nanoseconds, milliseconds, seconds, and/or minutes after excitation.

In some embodiments, one or more sensors 130 are configured to be calibrated optionally at least partially based an expected baseline image response (e.g. normal image response) for the fluid, tissue, cells, and/or lumen. As used herein, the term "normal image response" may include the detected intrinsic image response of one or more fluid, tissue, cells, and/or lumen as determined by researchers and/or medical or veterinary professionals for subjects of a certain age, ethnicity, etc. who do not have pathological conditions (e.g. control subjects). "Normal image response" may include the intrinsic detected image response of fluid, tissue, cells, and/or lumen of a subject prior to a pathological condition and/or of a comparable location not affected by the pathological condition.

In some embodiments, one or more sensors 130 may be configured to detect a condition of interest including, but not limited to, a temperature, a pressure, a fluid flow, an optical absorption, optical emission, fluorescence, or phosphorescence, an index of refraction at least one wavelength, an electrical resistivity, a density or sound speed, a pH, an osmolality, the presence of an embolism, the presence (or absence) of an object (such as a blood clot, a thrombus, an embolus, a plaque, a lipid, a gas bubble, an aggregate, a cell, a specific type of cell, a cellular component or fragment, a collection of cell, a gamete, a pathogen, or a parasite), and/or the presence (or absence) of a substance such as a biological marker, an antibody, an antigen, a peptide, a polypeptide, a protein, a complex, a nucleic acid, a cell and/or a cell of a particular type, a cellular component, an organelle, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, and/or a pollutant, for example.

As used herein, the term "target" may include a material of interest, optionally cells of interest such as, but not limited to blood cells and/or lymph cells. As used herein the term "possible and/or potential targets" includes entities having characteristics suggestive of targets, but not yet confirmed as targets. Materials of interest may include, but are not limited to, materials identifiable by one or more captured image responses (individually or as an aggregate signal). Such materials may include, but are not limited to, a blood clot, a thrombus, an embolus, an aggregate, a cell, a specific type of cell, a cellular component, an organelle, a collection or aggregation of cells or components thereof, a pathogen, an infected cell (e.g. virally-infected and/or parasite-infected), or a parasite.

One or more targets may include, but are not limited to, cancer cells, microbial cells, and/or infected cells. One or more cancer cells may include, but are not limited to, neoplastic cells, metastatic cancer cells, precancerous cells, adenomas, and/or cancer stem cells. Cancer types may include, but are not limited to, bladder cancer, breast cancer, colon cancer, rectal cancer, endometrial cancer, kidney (renal) cancer, lung cancer, leukemia, melanoma, non-Hodgkin's Lymphoma, pancreatic cancer, prostate cancer, skin (non-melanoma) cancer, and thyroid cancer. Cancers may include, but are not limited to, bone, brain, breast, digestive, gastrointestinal, endocrine, eye, genitourinary, germ line, gynecological, head and neck, hematologic/blood, leukemia, lymphoma, lung, musculoskeletal, neurologic, respiratory/thoracic, skin, and pregnancy-related.

Microbial cells (microorganisms) may include, but are not limited to, bacteria, protists, protozoa, fungi, and/or amoeba. Pathogens may include, but are not limited to, bacteria, viruses, parasites, protozoa, fungi, and/or proteins. Bacteria may include, but are not limited to, *Escherichia coli, Salmonella, Mycobacterium* spp., *Bacillus anthracis, Streptococcus* spp., *Staphylococcus* spp., *Francisella tularensis*, and/or *Helicobacter pylori*. Viruses may include, but are not limited to, Hepatitis A, B, C, D, and/or E, Influenza virus, Herpes simplex virus, *Molluscum contagiosum*, and/or Human Immunodeficiency virus. Protozoa may include, but are not limited to, *Cryptosporidium, Toxoplasma* spp., *Giardia lamblia, Trypanosoma* spp., *Plasmodia* spp. and/or *Leishmania* spp. Fungi may include, but are not limited to, *Pneumocystis* spp., *Tinea, Candida* spp., *Histoplasma* spp., and/or *Cryptococcus* spp. Parasites may include, but are not limited to tapeworms, helminthes, and/or roundworms. Proteins may include, but are not limited to, prions.

Embodiments of one or more device 100, 200, and/or 300 may include control circuitry 150 coupled to one or more sensors, and responsive to at least partially identify one or more targets during an expected transit time (optionally residence time) of the one or more targets through a detection area in one or more blood vessel or lymph vessel at least partially based on one or more captured image response. In some embodiments, the control circuitry 150 is responsive to identify one or more predicted future locations of the one or more targets at least partially based on the one or more image responses. In some embodiments, the control circuitry 150 is responsive to identify the effect of the ablation energy on the one or more targets at least partially based on the one or more image responses.

Embodiments of one or more device 200, include control circuitry 150 coupled to the one or more sensors 130, and responsive to at least partially identify one or more targets during an expected transit time (optionally residence time) of the one or more targets through a detection area in, or proximal to, the local bypass 210. Embodiments of one or more device 300, include control circuitry 150 coupled to the one or more sensors 130, and responsive to at least partially identify one or more targets during an expected transit time (optionally residence time) of the one or more targets through a detection area in, or proximal to, one or more reservoirs 310.

As used herein the term "expected transit time" includes, but is not limited to, the amount of time calculated and/or predicted to elapse while one or more possible targets are within the approximate boundaries of the detection area. Methods and calculations for predicting this time are described herein and/or known in the art. As used herein, the term "detection area" includes, but is not limited to, an area from which one or more sensors receive image responses and/or image information.

In some embodiments, the control circuitry 150 is configured to control one or more of one or more energy sources 110, one or more sensors 130, and/or one or more power sources 160. In some embodiments, the control circuitry is configured to control one or more of one or more insert 170, one or more vessel attachment units 180, and/or one or more vessel lumen anchors 190. In some embodiments, the control circuitry 150 may be directly coupled, indirectly coupled, and/or wirelessly coupled to one or more energy sources 110, one or more sensors 130, and/or one or more power sources 160. In some embodiments, the control circuitry 150 may be directly coupled, indirectly coupled, and/or wirelessly coupled to one or more of one or more insert 170, one or more vessel attachment units 180, and/or one or more vessel lumen anchors 190.

Control circuitry 150 may be electrical circuitry and/or other types of logic/circuitry including, for example, fluid circuitry, chemo-mechanical circuitry, and other types of logic/circuitry that provide equivalent functionality. The control circuitry 150 may include at least one of hardware, software, and firmware; in some embodiments the control circuitry may include a microprocessor. The control circuitry 150 may be located in or on the structural element of a device and/or at a location separate from the structural element. Control circuitry may be internal and/or external to the subject.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

In some embodiments, the control circuitry 150 is responsive to at least partially and/or completely identify one or more targets at least partially based on one or more of pattern recognition and/or shape recognition. In illustrative embodiments, amoeba, fungi, and/or protists may be identified through pattern and/or shape recognition. In some embodiments, the control circuitry 150 is responsive to at least partially and/or completely identify one or more targets at least partially based on an actual image optionally of one or more possible targets, optionally one or more cells. In illustrative embodiments, one or more amoeba and/or malaria-infected red blood cells may be identified by actual image. In some embodiments, the control circuitry 150 is responsive to at least partially and/or completely identify one or more targets at least partially based on relative and/or absolute size, optionally of one or more possible targets, optionally of one or more cells. In illustrative embodiments, one or more cancer cells may be identified at least partially based on size, either absolute, or compared with other cells. In some embodiments, the control circuitry 150 is responsive to at least partially and/or completely identify one or more targets at least partially based on surface features. In illustrative embodiments, one or more virally-infected cells and/or pathogen-infected cells may be identified based on changes in membrane morphology and shape, including for example blebs and knobs.

In some embodiments, the control circuitry 150 is responsive to identify select one or more characteristics of energy for eliciting an image response (e.g. excitation energy). In some embodiments, the control circuitry 150 selects one or more characteristics of energy for eliciting an image response responsive to one or more characteristics of a prior the image response and/or the energy selected to elicit the prior image response. In some embodiments, the control circuitry 150 selects one or more characteristics of energy for eliciting an image response responsive to input from external control circuitry. In some embodiments, the control circuitry 150 selects one or more characteristics of energy for eliciting an image response responsive to one or more characteristics of a known target, for example characteristics designed specifically identify the presence or absence of a particular cell and/or pathogen. In some embodiments, the control circuitry 150 selects one or more characteristics of energy for eliciting an image response in a pre-programmed manner.

In some embodiments, the control circuitry 150 is responsive to at least partially and/or completely identify one or more targets and/or target area at least partially based on one or more of one or more temporal locations, one or more spatial locations, and/or one or more temporal-spatial locations of the one or more identified targets. In some embodiments, the control circuitry 150 is responsive to at least partially and/or completely identify one or more targets and/or target area at least partially based on one or more of the velocity, the vibratory dynamic response, the angular response, and/or the inertial response of the one or more targets. In some embodiments, the control circuitry 150 is responsive to at least partially and/or completely identify one or more targets and/or target area at least partially based on predicting one or more future locations of the one or more targets.

In some embodiments, the control circuitry 150 identifies a target, target area, and/or target cells by determining one or more of the direction, the distance, the lumen depth, the time, and/or the coordinates from which an image response originated, optionally in relation to the energy used to elicit the one or more image response. In some embodiments, the control circuitry 150 identifies a target, target area, and/or target cells by analysis of one or more characteristics of an image response (e.g. presence and/or absence of an image response and/or density of a image response—grouping of cells that if non-grouped would not be considered a target), optionally including but not limited to, the electromagnetic spectrum, or parts thereof. In some embodiments, the control circuitry 150 identifies a target, target area, and/or target cells in real time.

As used herein, the term "target area" includes, but is not limited to, an area identified, determined, and/or predicted for at least partially ablating (optionally damaging, destroying, making non-viable, among others) one or more targets. In some embodiments, a target area is an approximately fixed location through which one or more targets are predicted to pass and/or actively moved toward (e.g. funneled, passed through a narrowing insert, passed through a valve, etc.). In some embodiments, a target area is determined by the presence (or predicted presence) of one or more targets.

In some embodiments, the control circuitry 150 is responsive to select one or more characteristics of ablation energy for at least partially ablating a target, target area, and/or target cells. In some embodiments, the control circuitry 150 selects one or more characteristics of ablation energy for at least partially ablating a target, target area, and/or target cells responsive to one or more characteristics of the image response and/or the energy selected to elicit the image response. In some embodiments, the control circuitry 150 increases the ablation energy responsive to an increase in the image response, and/or decreases the ablation energy responsive to a decrease in the image response. In some embodiments, the control circuitry 150 selects one or more characteristics of the ablation energy at least partially responsive to detection of one or more wavelengths of the image response.

In some embodiments, the control circuitry 150 is responsive to update targeting information on the basis of movement of part or all of a device 100, 200, and/or 300 and/or a target and/or target area. In illustrative embodiments, such target updating may be useful when the ablating energy may be delivered at a time (optionally substantially) later than the time at which an image response is detected, or when the target is moving in relation to the ablation energy source. In this case, the detected location may be updated to take into account possible motion of the target area and/or the device.

Motion of the image response location can be updated by registering the detected image response location relative to other, updatable, location information. In one example, the detected image response location is registered relative to fiducials within the individual. Then, the location of the fiducials is updated, and the site of the image response location at such time can be predicted based upon its known registration relative to the fiducial locations. In another example, the detected image response location is registered relative to features within an image of a related portion of the individual. Then, the image is updated and the location of the image response location at such time can be predicted based upon its known registration relative to the image features.

Motion, which may include location and/or orientation, of the device can be updated by a variety of methods, including inertial navigation, measurements based on beacons or fiducials, measurements based on orientation sensors, or combinations of such techniques. Inertial navigation can be performed with the support of accelerometers on the device, and may also incorporate use of gyroscopic sensors on the device. Beacons and/or fiducials can be used to measure the device's motion; the beacons or fiducials may be on the device and their location or direction measured by remote sensors. Alternatively, measurements of remote beacons or fiducials may be made by sensors on the device. Combined systems may be used, with mixtures of remote and on-board sensors, measuring the location or direction of remote or on-board beacons or fiducials. Orientation sensors, such as tilt sensors may be used to provide information of one or more aspects of the device's orientation. Motion information obtained from different sources or methods can be combined together to give improved motion estimates, using techniques such as nonlinear filtering, least-squares filtering, Kalman filtering, etc.

The updated image response location may then be combined, via a coordinate translation and rotation, with the updated position and location of the device. This results in updated coordinates or directions of the image response location with respect to the device, and can be used to direct the delivery of ablation energy.

In some embodiments, control circuitry 150 receives information from one or more sensors 130 and/or one or more external sources. Information may include, but is not limited to, a location of an untethered device, allowable dose limits (e.g. of energy for excitation and/or ablation), release authority (e.g. for release of energy for excitation, ablation, and/or release from an affixed and/or stationary location), control parameters (e.g. for energy release, for motion, for power, for sensors, etc.), operating instructions, and/or status queries.

In some embodiments, control circuitry 150 is feedback controlled, optionally from information from one or more sensors 130, and/or one or more external sources. In some embodiments, control circuitry 150 is monitored by one or more external sources, provides outputs to one or more sources, and/or sends outputs to one or more sources. In some embodiments control circuitry is remote-controlled, wirelessly controlled, programmed, and/or automatic. Equipment, methods, and software associated with control circuitry are described herein and/or known in the art (see e.g., U.S. Patent Applications 2007/0066939, 2007/0225633, Ser. No. 11/414,164 and Ser. No. 11/414,149).

Figure 6:
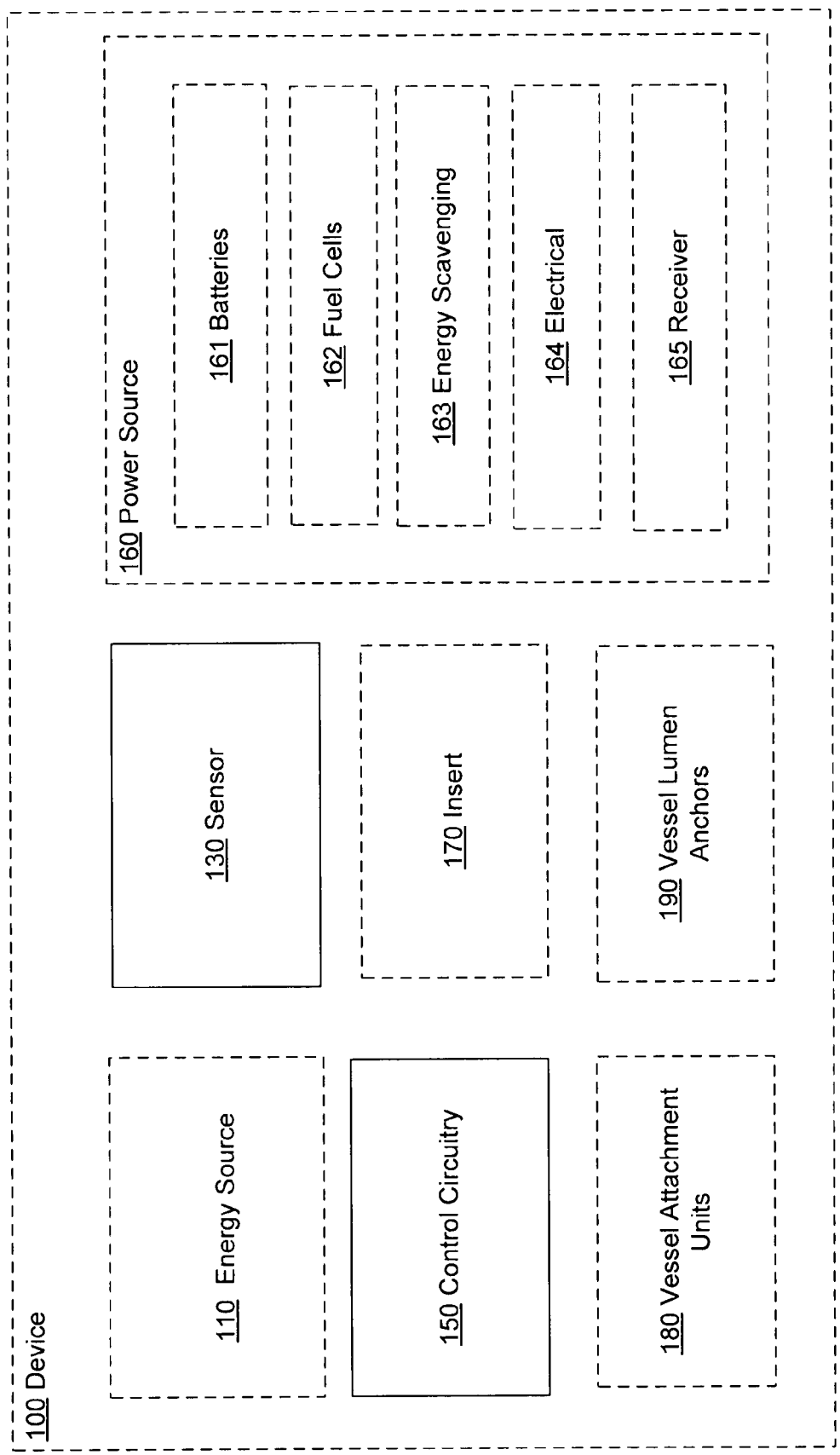
FIG. 6 shows a schematic of illustrative embodiments of the device of FIG. 1, with illustrative examples of a power source.

Embodiments of one or more device 100, 200, and/or 300 optionally include a power source 160 (see e.g., FIG. 6). One or more power sources 160 may be configured to provide power to one or more of one or more control circuitry 150, one or more sensor 130, and/or one or more energy source 110. One or more power sources 160 may be configured to provide power to one or more of one or more inserts 170, one or more vessel attachment units 180, and/or one or more vessel lumen anchors 190. One or more power sources 160 may be configured to provide power to one or more of one or more local bypass 210 and/or one or more reservoirs 310.

Power sources 160 may include, but are not limited to, one or more batteries 161, fuel cells 162, energy scavenging 163, electrical 164, and/or receivers 165 located on and/or in one or more parts of the one or more devices or separately from the one or more devices. The one or more batteries may include a microbattery such as those available from Quallion LLC (http://www.quallion.com), may be designed as a film (U.S. Pat. Nos. 5,338,625 and 5,705,293), or may be a nuclear battery. The one or more fuel cells may be enzymatic, microbial, or photosynthetic fuel cells or other biofuel cells (US2003/0152823A1; WO03106966A2 Miniature Biofuel cell; Chen T et al. J. Am. Chem. Soc. 2001, 123, 8630-8631, A Miniature Biofuel Cell), and may be of any size, including the micro- or nano-scale.

The one or more energy-scavenging devices may include a pressure-rectifying mechanism that utilizes pulsatile changes in blood pressure, for example, or an acceleration-rectifying mechanism as used in self-winding watches, or other types of flow rectifying mechanisms capable of deriving energy from other flow parameters. The one or more electrical power sources may be located separately from the structural element of the device and connected to the structural element by a wire, or an optical power source located separately from the structural element and connected to the structural element by a fiber-optic line or cable. The one or more power receivers may be capable of receiving power from an external source, acoustic energy from an external source, and/or a power receiver capable of receiving electromagnetic energy (e.g., infrared energy) from an external source.

In illustrative embodiments, one or more power sources 160 are optionally part of and/or are configured to open and/or close one or more valves, to attach or detach one or more anchors, to insert or remove one or more local bypass couplings, or to change conformations of one or more inserts. One or more of the mechanisms may include mechanical or micromechanical structures driven by at least one motor, micromotor, or molecular motor, or by expansion or change in configuration of a shape change polymer or metal. A molecular motor may be a biomolecular motor that runs on a biological chemical such as ATP, kinesin, RNA polymerase, myosin dynein, adenosinetriphosphate synthetase, rotaxanes, or a viral protein.

In some embodiments, the power source 160 optionally includes a power transmitter capable of transmitting power from one or more device to a secondary location or vice versa. The power transmitter may be capable of transmitting at least one of acoustic power, electrical power, or optical power, among others. The secondary location may be, for example, another device within the body, either in a body lumen or elsewhere that includes a power receiver and structures for using, storing and/or re-transmitting the received power.

In some embodiments, the power source 160 optionally includes a power receiver optionally configured to receive power from one or more external sources. Power may be received wirelessly or through a wired connection, for example. Power may be received from a battery pack or other power source (optionally continually renewable, such as motion re-charged) that can be worn or attached to a subject, and/or received from chargers present in buildings, homes, and/or care-giving settings (e.g. clinic and/or hospital).

In one aspect, the disclosure is drawn to one or more methods for imaging and optionally ablating one or more targets, optionally using one or more device 100, 200, and/or 300 described herein. Although one or more methods may be presented separately herein, it is intended and envisioned that one or more methods and/or embodiments of one or more methods may be combined and/or substituted to encompass the full disclosure. In some embodiments, one or more methods may include one or more operations, and be implemented using one or more computing devices and/or systems.

Embodiments of one or more methods for screening for, or against, one or more targets, optionally using a system including one or more device 100, 200, and/or 300, include locally capturing image information associated with one or more blood vessel or lymph vessel in a subject; analyzing the image information to at least partially identify one or more targets in real time; and optionally determining the absolute numbers and/or ratio (as compared to a control population of cells, for example) of one or more targets over a time interval.

Embodiments of one or more methods for imaging and optionally ablating one or more targets, optionally using a system including one or more device 100, 200, and/or 300, include locally capturing image information associated with one or more blood vessel or lymph vessel in a subject; analyzing the image information to at least partially identify one or more targets in real time (e.g. during residence time in the detection and/or destruction areas); selecting a target area at least partially based on the one or more identified targets; and locally providing energy to the target area in real time (e.g. during residence time in the detection and/or destruction areas), the energy having a magnitude selected to at least partially ablate the one or more targets.

Embodiments of one or more methods for modulating the biological activity of one or more targets in a subject, optionally using a system including one or more device 100, 200, and/or 300, include locally capturing image information associated with one or more blood vessel or lymph vessel in the subject; analyzing the image information to at least partially identify one or more targets; and locally providing energy in an amount sufficient to at least partially impair the biological activity (e.g. at least partially inactivate) of the one or more identified targets.

Embodiments of one or more methods of treating, ameliorating, and/or preventing a disease or disorder in a subject in need of such treatment, optionally using a system including one or more device 100, 200, and/or 300, include locally capturing image information associated with one or more blood vessel or lymph vessel in a subject; analyzing the image information to at least partially identify one or more targets in real time (e.g. during residence time in the detection and/or destruction areas); selecting a target area at least partially based on the one or more identified targets; and locally providing energy to the target area in real time (e.g. during residence time in the detection and/or destruction areas), the ablation energy having characteristics appropriate to at least partially ablate the one or more identified targets, wherein the one or more identified targets are associated with the disease or disorder.

Embodiments of one or more methods include affixing one or more devices 100, 200, and/or 300 to a location in, or proximal to, a blood vessel or lymph vessel. As used herein, the term "affixing" may include, but is not limited to one or more processes by which the one or more devices may be held stationary in the lumen or internal location. The affixation may be temporary and/or permanent as described herein. Mechanisms by which one or more device may become affixed are known in the art and/or described herein.

Embodiments of one or more methods include locally and/or externally (e.g. external to the subject) providing energy, optionally electromagnetic energy and/or acoustic energy (e.g. ultrasonic energy) selected to induce an image response (e.g. elicit image information), to a target, target area, target cell, target tissue, internal location, and/or blood or lymph vessel, optionally the vessel lumen. Electromagnetic energy optionally includes, but is not limited to, optical energy (e.g. visible light), infrared energy, ultraviolet energy, and/or radiofrequency energy. Providing electromagnetic energy optionally includes using a laser or other device to provide optical energy to a target.

Parameters associated with the selection of energy to induce an image response (and/or elicit image information) include, but are not limited to, the target, the environment associated with the target, the characteristics of the energy source 110, optionally an electromagnetic energy source 111, and/or an acoustic energy source 120, and/or the characteristics of the one or more sensors 130.

The parameters associated with the target include, but are not limited to, the distance of the target from the energy source 110, the depth of the target beneath a surface (e.g. a lumen wall), the inherent characteristics of the target (e.g. fluorescence), the size of the target, and/or the movement of the target (e.g. stationary, steady movement, variable movement, predictable movement, etc.).

The parameters associated with the environment include, but are not limited to, location, milieu (e.g. many cells, few cells), movement (e.g. stationary, steady movement, intermittent movement, predictable movement, etc.), physiologic parameters (e.g. pH, temperature, etc.), and/or non-target image responses (e.g. background fluorescence, non-specific fluorescence, intrinsic non-target fluorescence, etc.).

The parameters associated with the characteristics of the electromagnetic energy source 111 include, but are not limited to, the wavelengths available for selection (e.g. single, two-photon, multiple, extended-spectrum, etc.), the strength of the emitted electromagnetic energy (e.g. limitations on distance and/or depth, etc.), the type of output (e.g. pulsed, two-photon, etc.), directionality (e.g. limited, variable, varied, etc.), and/or spatial parameters (e.g. limited, focused, collimated, etc.).

The parameters associated with the characteristics of the sensor 130 include, but are not limited to, the detection limits associated with wavelength (e.g. single, two-photon, multiple, extended-spectrum, etc.), signal strength (e.g. sensitivity of detection, level above background, etc.), and/or time (e.g. detects cumulative readings over time, detects readings at certain time intervals, or at a certain time post excitation, etc.). Parameters associated with the characteristics of the sensor 130 include, but are not limited to, the type of image response and/or image information captured by the sensor 130.

In some embodiments, image information includes, but is not limited to, one or more of acoustic image information (e.g. ultrasonic image information), thermal image information, and/or electromagnetic image information, optionally radiofrequency image information and/or optical image information (e.g. visible light image information, infrared image information, ultraviolet image information, and/or color image information). In some embodiments, image information includes scattering response information (e.g. light scatter, but optionally other energy scatter responses)

and/or absorptive response information (e.g. lack of back scatter from energy excitation). In some embodiments, image information includes, but is not limited to, one or more of spatial and/or temporal information, and/or velocity information relating to fluid and/or cellular flow (e.g. one or more possible targets in the lumen). Appropriate sensors 130 for capturing image information and their selection are known to one of skill in the art and/or described herein.

Embodiments of one or more methods include selecting the energy to induce the image response. Methods for selecting include, but are not limited, manually, remotely, automatically, programmably, wirelessly, and/or using control circuitry. Manually selecting includes, but is not limited to, manually operating one or mechanism (e.g. a switch, dial, button, setting, etc.) on one or more device 100, 200, and/or 300 that controls the characteristics of the energy emitted from one or more energy source 110. Remotely selecting includes, but is not limited to, optionally wirelessly interacting with circuitry on one or more device 100, 200, and/or 300 that controls the characteristics of the energy emitted from one or more energy source 110. Programmably selecting includes, but is not limited to, optionally using control circuitry 150, optionally part of one or more device 100, 200, and/or 300 (e.g. internal and/or external to the subject), programmed, optionally manually, remotely, and/or wirelessly, to select the characteristics of the energy emitted from one or more energy source 110. Methods for programming control circuitry and applicable control circuitry are well-known to one of skill in the art and/or described herein.

Embodiments of one or more methods include monitoring the energy selected to induce an image response and/or elicit image information, monitoring the energy selected to ablate the target, optionally electromagnetic energy, acoustic energy, and/or particle beam energy. Methods of monitoring electromagnetic energy, acoustic energy and/or particle beam energy are known in the art and/or described herein. Methods include, but are not limited to, using sensors able to detect one or more characteristics of the energy.

Embodiments of one or more methods include capturing, optionally locally (e.g. using one or more sensors 130), image information associated with one or more blood vessel and/or lymph vessel, optionally the vessel lumen. In some embodiments, image information is captured sequentially. In illustrative embodiments, image information is captured by a first sensing system (e.g. sensor 130, energy source 110, and/or control circuitry 150), of fluid and/or cellular flow in a blood or lymph vessel lumen. If analysis optionally by control circuitry 150 of the image information indicates the presence of one or more possible targets, then additionally image information is captured, optionally by a second sensing system (e.g. sensor 130, energy source 110, control circuitry 150 and/or insert 170) further downflow from the first sensing system. This second sensing system may optionally include an insert to direct the one or more possible targets to a detection area for sensing using one or more optionally different types of sensors 130.

Embodiments of one or more methods include detecting an image response. Methods of detecting an image response include, but are not limited to, detecting an image response using one or more sensors 130, detectors, and/or monitors. Sensors 130, detectors, and/or monitors appropriate for detection and/or monitoring of the image response are known in the art and/or described herein. As used herein, the term "detecting" may include any process by which one or more characteristics of an image response may be measured and/or quantified.

Embodiments of one or more methods include identifying a target for ablation (e.g. target area, target cells, and/or target tissues). As used herein, the term "identifying a target" may include, but is not limited to, processes including selecting a target and/or determining a target. One or more methods for identifying a target for ablation optionally include analyzing an image response, image information, and/or other information, optionally using control circuitry 150, optionally in real time.

Embodiments of one or more methods include analyzing image information, optionally using control circuitry 150. In some embodiments, analyzing the image information includes comparing the image information to one or more of reference image information and/or target image information (see e.g. U.S. Patent Applications 2007/0066939 and 2007/0225633). In some embodiments, this comparison includes comparing one or more of cell shape and/or cell outline information with reference and/or targets cell shapes and/or cell outline information. In some embodiments, this comparison includes comparing one or more of intracellular shape and/or intracellular outline information with reference and/or target intracellular shape and/or intracellular outline information. In some embodiments, analyzing the image information includes performing one or more of pattern recognition or shape recognition analysis. Software, systems, and/or firmware, for example, for performing these calculations and analyses is known in the art and/or described herein.

In some embodiments, analyzing the image information includes determining temporal and/or spatial information associated (and/or correlated) with the image information. In some embodiments, analyzing the image information includes determining velocity of the fluid and/or cellular flow (e.g. velocity of target movement) associated (and/or correlated) with the image information. In some embodiments, analyzing the image information includes predicting future spatial and/or temporal locations associated with the image information. Software, systems, and/or firmware, for example, for performing these calculations and analyses is known in the art and/or described herein.

In illustrative embodiments, image information is analyzed either by control circuitry in the subject and/or by control circuitry external to the subject, optionally transmitted wirelessly. The control circuitry analyzes the image information in real time and/or within the expected transit time through the detection area and/or to the destruction area (e.g. target area). If one or more targets is identified for ablation the target may be ablated in real time, and/or its arrival in a destruction area may be predicted using control circuitry. In this event, control circuitry optionally uses information relating to measurements of fluid and/or cellular for determined from the image information to predict the time for ablation and/or the location for ablation. Software, systems, and/or firmware, for example, for performing these calculations and analyses is known in the art and/or described herein Analyzing an image response to at least partially identify a target for ablation may include, but is not limited to, evaluating an image response at least partially in reference to baseline, background, and/or non-specific image responses, as well as expected, reference, and/or normal image responses (e.g. baseline fluorescence, background fluorescence, expected fluorescence, normal fluorescence, reference fluorescence, non-specific fluorescence, and/or intrinsic non-target fluorescence, etc.). Analyzing an image response may include, but is not limited to, subtractively determining an image response, optionally a target fluorescent response (e.g. subtracting the non-target fluorescence from the total fluorescence to determine the target fluorescence). Analyzing an image response may include, but is not limited to, evaluating an image response at least partially based on detection at one or more wavelengths (e.g. single, multiple, extended-spectrum, etc.), based on time (e.g. one or more times, time intervals, and/or over time, etc.), based on direction (e.g. of origination of the emission, etc.), based on strength, and/or based on distance (e.g. of origination of emission from a sensor). In illustrative embodiments, analyzing an image response may include, but is not limited to, identifying "clumps" and/or "groups" of cells that in another context might be considered "normal", but that are not normally grouped and so may be a target for ablation (see e.g. U.S. Patent Applications 2007/0066939 and 2007/0225633).

In illustrative embodiments, an analyzed target image response is used to determine the direction from which the response originated in order to provide ablation energy to the location and/or general area. In illustrative embodiments, an analyzed target image response is used to determine the coordinates from which the response originated in order to provide ablation energy to the location and/or general area.

As used herein, the term "location" may include, but is not limited to, one or more of a direction, an area, a depth, a site, or a size, etc. A location may be defined by spatial coordinates and/or temporal coordinates. A location may be defined as precisely as the cellular level, for example, or as broadly as a general area, or a general direction. Methods of determining a location based on the detection of a image response are known in the art and/or described herein. In illustrative embodiments, a target location may be the lumen of a blood vessel following detection of a target image response.

Analyzing other information to at least partially identify a target for ablation may include, but is not limited to, analyzing information optionally provided by one or more sensors 130 (e.g. intrinsic and/or extrinsic to one or more deviceloo, 200 and/or 300) and/or provided by one or more external sources (e.g. remotely and/or wirelessly, etc.). Analyzing information optionally provided by one or more sensors may include analyzing information including, but not limited to, environmental information such as, but not limited to, pH, temperature, pressure, chemistry, physiological measurements, dietary measurements, biological measurements, etc. In illustrative embodiments, identifying a target fluorescent response is a least partially based on identifying the pH of the environment, optionally detecting an acidic pH. Analyzing information optionally provided by one or more external sources may include analyzing information including, but not limited to, environmental information and/or medical and/or veterinary professional information.

Analyzing an image response to at least partially identify a target for ablation may include, but is not limited to, evaluating an image response in real time. As used herein, the term "in real time" may include, but is not limited to, immediate, rapid, not requiring operator intervention, automatic, and/or programmed. In real time may include, but is not limited to, measurements in femtoseconds, picoseconds, nanoseconds, milliseconds, as well as longer, and optionally shorter, time intervals. In illustrative embodiments, analysis in real time is sufficiently rapid such that the target and the device have not moved and/or changed positions/locations significantly with respect to each other such that ablation energy sent along the path of the initial excitation energy will cause damage to the one or more identified targets. In illustrative embodiments, an image response is detected and analyzed, and a target is identified without operator intervention and the target ablation information is provided to an energy source.

In some embodiments, in real time may include during a period of residence of the one or more targets in a detection area and/or an ablation area. One or more of the diction area and/or the ablation area may be in the local bypass 210 and/or in a reservoir 310. In some embodiments, on or more of analyzing image information and/or providing ablation energy may be performed during a period of residence of the one or more targets.

Embodiments of one or more methods include providing energy to at least partially ablate a target, optionally from one or more local energy sources 110 and/or from one or more external energy sources (e.g. external to the subject). One or more methods include providing energy to at least partially ablate a target in real time. As used herein the term "ablation or ablate" may include, but is not limited to, processes including destroying, modifying, removing, inactivating, and/or eliminating, in part or in whole, a target and/or a material of interest. As used herein, ablation may include the process of removing material and/or damaging and/or inactivating a biological entity by irradiating it, optionally with a laser beam, optionally with a pulsed laser, or a continuous wave laser. As used herein, the term "inactivating" includes but is not limited to, damage such that the biological entity is no longer viable, cannot reproduce, and/or is no longer infectious.

Energy for ablation may include, but is not limited to, electromagnetic energy, acoustic energy (e.g. ultrasonic energy), X-ray energy, and particle beam energy. Electromagnetic energy such as light may cause, for example, a photoreaction, molecular bond breakage, heating, or other appropriate effect. Electromagnetic energy sources 110 may include, but are not limited to, light sources such as light emitting diodes and laser diodes, or sources of other frequencies of electromagnetic energy, radio waves, microwaves, ultraviolet rays, infra-red rays, optical rays, thermal energy, terahertz beams, and the like.

As used herein, the term "at least partially ablate" may include partially and/or completely ablating a target. As used herein, the term "completely ablate" may include ablation of a target up to the applicable limits of detection (e.g. no longer detectable by the sensors used to detect the image response, no longer detectable over background, and/or no longer statistically significant). As used herein the term "partially ablate" may include ablation less than complete ablation, but where at least some detectable ablation occurs. At least some detection ablation includes, but is not limited to, ablation detectable by the sensors used to detect the image response, statistically significant ablation, detection by external sensors, and/or detection by inference from other measurements and/or sensor readouts.

Embodiments of one or more methods include locally inhibiting fluid and/or cellular flow associated with one or more blood vessel or lymph vessel, optionally associated with a vessel lumen. In some embodiments, locally inhibiting fluid flow includes locally restricting cellular flow in the lumen. In some embodiments, locally inhibiting fluid flow includes modifying cellular flow such that one or more cells traverse the lumen in single file and/or traverse a localized region of the lumen. In some embodiments, locally modifying fluid flow includes at least partially reducing and/or constricting an internal and/or external circumference of the vessel lumen. In some embodiments, locally modifying fluid flow includes locally compressing and/or at least partially occluding the lumen. In some embodiments, locally modifying fluid flow includes activating a local compression mechanism and/or local occlusion mechanism associated with the lumen.

As used herein the term "modifying" includes, but is not limited to, changes made to the referent which may be partial and/or complete. For example, modifying fluid flow may include increasing and/or decreasing fluid flow and/or inhibiting and/or enhancing fluid flow. Modifying fluid flow may refer to increasing and/or decreasing the speed of the fluid flow and/or the amount of the fluid flow. Modifying fluid flow may refer to changing the direction and/or path of the fluid flow. These changes may be partial (e.g. less than complete inhibition, but yet measurable) and/or complete (e.g. no detectable fluid flow can occur, and/or a non-significant amount of fluid flow occurs). Unless indicated otherwise, generally modification refers to partial, not complete modification (e.g. partial, not complete inhibition). Methods for detecting changes in fluid and cellular flow are known in the art and/or described herein. To be considered modified, changes are measurable, and optionally statistically significant differences as compared to the previous, calculated, and/or reference amounts of fluid flow.

In illustrative embodiments, locally modifying fluid and/or cellular flow may occur using one or more insert 170 and/or one or more valve. In illustrative embodiments, image information is optionally captured of the modified fluid flow, and optionally analyzed by control circuitry 150. In some embodiments, ablation and/or modification (inactivation energy) is provided to the modified fluid flow. For example, image information may be enhanced when captured from fluid and/or cells moving at a reduced speed, or reduction in speed may permit more time for analysis by control circuitry 150 of the image information, or permit additional or different types of sensors to capture image information. In illustrative embodiments, inhibition and/or reduction in speed of fluid flow (or capture of one or more targets) my facilitate ablation of one or more targets, either through prediction and/or calculation of a predicted future location or time of passage through a known location, or through directing the one or more targets to a destruction area.

Embodiments of one or more methods optionally include at least partially (optionally completely) diverting fluid flow from and at least partially returning fluid to a lumen of one or more blood vessel and/or lymph vessel, optionally through a local bypass. In some embodiments, this process of diversion and return of fluid flow is controllable and/or programmable. In illustrative embodiments, fluid is diverted from a vessel lumen optionally through a valve leading to a local bypass (e.g. an optionally optically pure channel) in which additional image information can be captured and optionally ablation can occur. The local bypass may be in line with the vessel lumen, internal to the vessel lumen, and or an off-branch from the vessel lumen. Illustrative examples are provided herein.

In some embodiments, the methods include controllably attaching the local bypass to the one or more vessel. In illustrative embodiments, the insert may be provided to (and removed from) the appropriate location via some form of microsurgery. The connections attaching the local bypass in local may optionally be remotely and/or wirelessly and/or programmably activated and de-activated to facilitate this process.

In some embodiments, image information is captured associated with the local bypass. In some embodiments, the image information is captured in the vessel lumen upflow and/or downflow of the local bypass, and/or in the local bypass lumen. In illustrative embodiments, image information is captured upflow of the local bypass, analyzed by control circuitry and then the valve leading to the local bypass is opened or closed depending, for example, on whether any possible targets are detected. Once in the local bypass, additional sensing may be performed (or this may be where all sensing takes place and the bypass opens and closes according to a program or parameters other than the presence or absence of possible targets in the vessel lumen). The local bypass is optionally designed for optical imaging such that better measurements are optionally available. More than one sensor system is optionally present in the local bypass, and more than one type of imaging may be done on all cells, done randomly on a subset of cells, and/or done sequentially on cells depending on earlier sensing results. In illustrative embodiments, image information is captured downflow of the local bypass (or downflow of the upflow bypass valve) in the vessel lumen, optionally to document cells that do not enter the bypass lumen, and/or to document cells exiting the bypass lumen.

In some embodiments, the target area is selected in the local bypass. In some embodiments, selection of the target area is based at least partially on a predicted future path of the one or more targets, and/or on a predicted time of arrival of the one or more identified targets at an identified location in the local bypass.

Some embodiments include locally modulating fluid flow in the local bypass (optionally using a bypass insert 216), optionally reducing fluid flow and/or increasing fluid flow in the local bypass. In some embodiments modulating fluid flow in the local bypass includes modulating the lumen of the local bypass. Methods relating to modulating fluid flow in a vessel are discussed herein, and are applicable to the local bypass unless context dictates otherwise.

Embodiments of one or more methods include locally collecting one or more identified targets in one or more reservoirs 310. In some embodiments, image information is captured from the lumen of the one or more reservoirs. In some embodiments, energy is provided to the lumen of the one or more reservoirs to elicit the image information and/or to ablate one or more targets. In illustrative embodiments, one or more reservoirs are configured to receive one or more targets (or possible targets) identified by one or more sensing systems upflow from the reservoir. Within the reservoir, the one or more targets (or possible targets) optionally undergo additional tests and analysis from one or more sensing systems optionally including counting the numbers of one or more targets optionally during a defined time period) and/or are simply collected for further analysis ex vivo. Information relating to the targets may be provided to one or more external control circuitry, and/or accessible to one or more external sources through wireless technology.

In some embodiments, the reservoir lumens are accessed from the exterior of the subject, optionally so that the one or more possible targets and/or one or more targets can undergo additional tests and analysis ex vivo. In illustrative embodiments, the reservoirs are placed to facilitate external access from the subject and/or medical professionals. Optionally a permanent or semi-permanent conduit may be in place to allow easy access. Optionally access is through a large bore needle (e.g. biopsy needle).

Embodiments of one or more methods may include combinations including one or more bypass, one or more insert, one or more reservoir, etc in a variety of combinations and configurations, as well as one or more sensors 130, energy sources 110, control circuitry 150, and power sources 160.

EXAMPLES

The following Examples are provided to illustrate, not to limit, aspects of the present invention. Materials and reagents described in the Examples are commercially available unless otherwise specified.

Example 1

Detection of Biological Targets in Vessels Using Light Scattering

An untethered device configured to function in or proximal to a blood vessel or a lymph vessel may be used to detect specific biological targets based on differential scattering of light. As such, a cell or cells in the vessel circulation may pass through an examination zone either incorporated within the device or in close proximity to the device. A cell or cells may be, for example, a bacterium, a protozoan, a platelet, a red blood cell, a lymphocyte, a monocyte, a neutrophil, an eosinophil, a circulating tumor cell or a combination thereof.

For imaging through use of differential scattering, the cell or cells are illuminated in an examination zone with a focused beam of energy. The beam may be a form of electromagnetic energy such as, for example, white light, laser light, X-rays, or infrared radiation. The device measures the optical interactions of the electromagnetic energy with the cell or cells, such as multiple wavelength absorption, scatter as a function of angle, or fluorescence as a function of either wavelength or polarization. The information regarding the optical interactions may be captured by a photosensor such as, for example, a CCD (charge coupled device) and/or a CMOS (complementary metal oxide semiconductor) sensor.

The captured information is processed internally by the device or sent wirelessly to an external processor. In real time, the captured information is compared with preset algorithms defining, for example, the light scattering properties of cells normally found in the circulation. For example, forward light scattering may provide a rough indication of cell size while side light scattering may provide a rough indication of cellular granularity, membrane complexity, and number of organelles. Alternatively (or additionally), the captured information is compared with preset algorithms defining, for example, the light scattering properties of abnormal blood cells or cells foreign to the circulation such as bacteria or circulating neoplastic cells, for example.

Upon identification of an abnormal cell or cells, the information may be provided to an external source through control circuitry, additional sensing parameters may be instigated, the cells may be provided to a reservoir for storage and optional retrieval, and/or the device may emit radiation sufficient to at least partially modify (or render non-viable or at least of reduced viability) the targeted cell. Alternatively, the device triggers emission of radiation from a second component of the device positioned downstream from the first detecting device.

Lymphocytes, monocytes, and granulocytes may be differentiated from one another under conditions of flow using, for example, a four-parameter light scattering technique used, for example, in flow cytometry (Terstappen et al. (1988) Cytometry 9:39-43). Electromagnetic energy emitted from a laser at wavelengths from 400 nm to 700 nm, for example, is differentially scattered by a cell or cells in the examination zone. The light scattering intensity may be simultaneously measured, for example at angles between 1.0 and 2.6 degrees and 3.0 and 11.0 degrees. Eosinophilic granulocytes may be differentiated from neutrophilic granulocytes by simultaneous measurement of the orthogonal and depolarized orthogonal light scattering. Platelets and red blood cells exhibit minimal light scattering at the angles described above and are consequently excluded from the analysis. Alternatively, red and white blood cells may be distinguished by simultaneously observing forward and orthogonal light scatter at a wavelength of 413.1 nm, for example (Ost et al. (1998) Cytometry 32:191-197). Alternatively, a diode laser emitting, for example, at either 670 nm or 780 nm may be used to distinguish lymphocytes, monocytes, neutrophils, and eosinophils using a combination of forward, orthogonal, and depolarized orthogonal scatter (Doombos et al. (1993) Cytometry 14:589-594).

Lymphocytes, granulocytes, and red blood cells may also be differentiated from one another based on forward and side light scattering under conditions of flow in an in vivo analysis, for example, of a surgically exposed mesentery artery (see, e.g., U.S. Pat. No. 7,264,794 B2).

An abnormal white blood cell associated with, for example, acute myeloblastic leukemia (AML), may be differentiated by light scatter. AML is characterized by uncontrolled proliferation of malignant myeloid progenitors in the bone marrow, at the expense of normal proliferation of white blood cells, red blood cells, and platelets. These immature white blood cells or blasts are arrested in their maturation process and can easily egress from the bone marrow into the circulation. Sarcomas found in various solid tissues may arise from metastasis of AML (Konoplev & Bueso-Ramos (2006) Ann. Diag. Path. 10:39-65).

AML blast cells may be differentiated from T-lymphocytes, for example, by measuring low angle forward light scatter and orthogonal light scatter (Vidriales et al. (1995) J. Clin. Pathol. 48:456-462). As such, the device may be used to induce and detect the patterns of forward and orthogonal light scatter of AML blast cells, for example, in the circulation. These patterns may be compared with those of normal white blood cells using preset algorithms.

Differential light scattering may also be used to detect circulating tumor cells derived from metastasis of solid tumors. In general, a circulating tumor cell is characterized by its large size, immature appearance, increased nuclear to cytoplasmic ratio, abnormally shaped nuclei, and disproportionately large nucleolus or multiple nucleoli (Moore et al. (1960) Cancer 13:111-117).

The size differential between a circulating tumor cell and components of the blood may be used to specifically detect the cancerous cells. For example, the average diameter of neutrophils, red bloods cells, and platelets is 10.5-12.5 microns, 7-8 microns, and 3 microns, respectively. In contrast, the average size of circulating tumor cells isolated from patients with breast, colon, stomach and lung cancers range from 18.3 to 20.6 microns in diameter (Moore et al. (1960) Cancer 13:111-117). Similarly, circulating neuroblastoma tumor cells are greater than 20 microns in diameter (Mohamed et al. (2004) IEEE Transactions on Nanobioscience, 3:251-256).

While neuroblastoma is a radiosensitive tumor, long-term control is difficult due to metastasis. Therefore, the ability to detect and ablate circulating tumor cells, such as neuroblastoma cells, may aide in the treatment of this cancer. As such, the size of a cell or cells passing through the examination zone is determined using forward light scattering. The size, as measured for example in diameter, is compared with known parameters regarding the size of normal blood components. Detection of an abnormally large cell may signal the presence of a circulating tumor cell and may trigger an ablation response.

An untethered device configured to function in or proximal to a blood vessel or lymph vessel may also be used to detect circulating bacteria relative to other cellular components of the circulation based on size analysis using light scattering. Bacteria are on average 0.2 to 1.0 microns in diameter as compared to 1.5 to 3.0 microns for platelets, for example. *Staphylococcus aureus* bacteria, for example, are perfectly round and approximately 1 micron in diameter. As such, a bacterium may be distinguished from platelets and other larger blood cell components based on size as described herein. The diameter as well as the length of the rod-shaped Escherichia coli bacteria, for example, may be determined using polarized light scattering, as described by Bronk et al. ((1995) Biophysical J. 69:1170-1177).

Other pathogens may be detected in the circulation based on size analysis and light scattering. For example *Trypanosoma brucei gambiense*, a blood borne protozoan associated with African sleeping sickness, has a unique elongated cellular shape relative to the predominantly spherical shape of normal cellular components of the blood. It is 25-40 microns in length, with a flagellum. As such, is anticipated that the light scattering properties of trypanosomes will be readily distinguished from those of normal components of the vasculature.

Blood cells infected with the parasite *Plasmodium falciparum* may be differentiated from other cells in the vasculature using differential light scatter at 10 degrees (complexity) and polarized light scatter at 90 degrees (lobularity) based on the pigmentation of the parasite (Mendelow et al. (1999) Br. J. Haematology 104:499-503).

Example 2

Detection of Biological Targets in Vessels Using Electrical Impedance and Dielectric Properties An untethered device configured to function in or proximal to a blood vessel or lymph vessel may be used to detect specific biological targets based on changes in electrical impedance relative to cell size. As such, a cell or cells in the vessel circulation may pass through an examination zone either incorporated within the device or in close proximity to the device.

The examination zone may contain two or more electrodes between which an electric current flows. As each cell passes through the electric current in the examination zone, it displaces its own volume of conducting fluid (i.e. plasma), momentarily increasing the impedance within the examination zone. This change in impedance produces a tiny but proportional current fluctuation that can be converted into a voltage pulse. The amplitude of this pulse is directly proportional to the volume of the cell that produced it. As such, the device may detect changes in electrical impedance and convert this information into volume information that may be compared with preset algorithms defining, for example, the volume of normal blood cells or cells foreign to the circulation such as bacteria or circulating neoplastic cells.

Cellular components of the blood may be differentiated based on volume using electrical impedance as described herein and/or commonly practiced using a Coulter counter. For example, platelets range in volume from 2 to 20 femtoliters (fL) whereas red blood cells range in volume from 70-90 fL (Hauser (2001) International Waldenstrom's Macroglobulinemia Foundation). Neutrophils and eosinophils range in volume from 160 to 450 fL while monocytes range in volume from 90 to 160 fL. By comparison, bacteria may be as small as 1 fL whereas a circulating tumor cell may be as large as 2000 fL. As such, changes in the electrical impedance in the examination zone may be used to differentiate between various components of the blood.

A MEMS resembling a miniaturized Coulter counter may be incorporated into the device described herein and may be constructed using thin platinum electrodes with a sensing zone of, for example, 20-100 microns (see, e.g., Zheng et al. (2006) Proceedings of 2006 International Conference on Microtechnologies in Medicine and Biology, IEEE, Okinawa, Japan, 9-12 May, 2006; Gao et al. (2003) Proceedings of the $25^{th}$ Annual International Conference of the IEEE EMBS, Cancun, Mexico, Sep. 17-21, 2003).

Alternatively, cellular components of the blood may be differentiated using electrical impedance spectroscopy. In this instance, the electrical impedance of a given cell is obtained by applying impulses over a range of frequencies from, for example, 10 Hz to 10 MHz and measuring the impulse response. The resulting spectrum is characteristic of a given cell type. For example, T lymphocytes exhibit resonance at 1.0 MHz, 2.9 MHz, 3.6 MHz, 4.5 MHz, 5.5 MHz, and 6.3 MHz while B lymphocytes exhibit resonance at 0.6 MHz, 1.7 MHz, 4.3 MHz, 5.0 MHz, 5.8 MHz, and 6.3 MHz (Liu et al. (1998) IEEE: Proceedings of the $20^{th}$ Annual International Conference of the IEEE Engineering in Medicine and Biology Society, Vol. 20, No. 4, 1881-1884).

A component capable of micro electrical impedance spectroscopy may be generated using MEMS and/or Lab-on-a-chip technology and incorporated into the untethered device described herein (see, e.g., Sun et al. (2007) Meas. Sci. Technol. 18:2859-2868; Mohanty et al., Microtechnologies in Medicine and Biology 485-488).

Normal and cancerous lymphocytes may be distinguished by differences in the relative capacitance and conductivity of their respective cell membranes using dielectric spectroscopy (Feldman et al. (2003) IEEE Transactions on Dielectrics and Electrical Insulation 10:728-753).

Example 3

Detection of Biological Targets in Vessels Using Infrared Spectroscopy

An untethered device configured to function in or proximal to a blood vessel or a lymph vessel may be used to detect specific biological targets based on infrared spectroscopy imaging. As such, a cell or cells in the vessel circulation may pass through an examination zone either incorporated within the device or in close proximity to the device. The cell or cells are illuminated in the examination zone by an electromagnetic energy source emitting radiation at infrared wavelengths. The device measures the optical interactions of the electromagnetic energy with the cell or cells, such as absorbance as a function of wavelength. The absorbance information is captured by the device and either processed internally or sent wirelessly to an external processor. In real time, the captured information is compared with preset algorithms defining, for example, the infrared absorbance properties of normal blood cells and circulating tumor cells.

Infrared spectroscopy is a nondestructive photonic technique that provides a rapid measure of sample chemistry. A tissue or cell contains various chemical components with characteristic infrared spectra, including proteins, nucleic acids, carbohydrates and lipids. These spectra are created when a molecule converts infrared radiation into molecular vibrations. These vibrational movements create bands in a spectrum that occur at specific wavelengths ($cm^{-1}$). Subtle differences in the chemical composition of a tissue or cell can be distinguished by subtle changes in the spectra. Chemical concentrations may be quantified by spectral absorbance properties at specific wavelengths, while subtle molecular structural changes may be indicated by spectral peak shifts, band shapes and relative intensity changes occurring across the spectrum.

Infrared covers the electromagnetic spectrum from wavelengths of 0.78 to 1000 μm. In the context of infrared spectroscopy, wavelength may be expressed as wavenumber with units of $cm^{-1}$, such that the wavenumber is equal to the reciprocal of the wavelength in centimeters. For analysis of tissue and cells, for example, spectral data may be taken at wavenumbers between 3500 and 1000 $cm^{-1}$, corresponding to wavelengths between 2.8 μm and 10 μm.

Infrared spectroscopy has been used, for example, to distinguish normal epithelial cells from cancerous epithelial cells in the prostate. Glandular epithelial cells in the prostate are the primary cell type involved in prostate adenocarcinoma and can be found in the circulation as a result of tumor metastasis. The infrared spectra of malignant prostate epithelial cells can be distinguished from normal epithelial cells at a variety of different wavenumbers or spectral biomarkers ranging from 966 to 3290 $cm^{-1}$ and can be further distinguished from, for example, lymphocytes (Fernandez et al. (2005) Nat. Biotech. 23:469-474). As such, the device may contain an electromagnetic energy source capable of emitting infrared radiation at wavelengths/wavenumbers in the range described above and may be a laser diode or diodes emitting at a specific wavelength or a type of tunable lead salt laser, for example.

Infrared spectroscopy may also be used to detect bacteria in the blood. For example, Fourier Transfer Infrared (FT-IR) Spectroscopy may be used to distinguish *Streptococcus pneumoniae, Haemophilus influenzae,* and *Morazella catarrhalis* bacteria in serum using a spectral range of wavenumbers from 4000 to 800 $cm^{-1}$ (U.S. Pat. No. 6,379,920 B1). *H. influenzae*, for example, exhibits increased absorbance at 1077 $cm^{-1}$ relative to serum alone or other bacteria tested. Alternatively, FT-IR data may be obtained at various frequency ranges, such as, for example, 3000-2800 $cm^{-1}$, 1800-1500 $cm^{-1}$, 1500-12000 $cm^{-1}$ 1200-900 $cm^{-1}$ and 900-700 $cm^{-1}$ and spectra obtained in these various ranges compared with known spectra of various bacteria (see, e.g., Oberreuter et al. (2002) Int. J. Syst. Evol. Microbiol. 52:91-100).

Example 4

Detection of Biological Targets in Vessels Using Acoustic Imaging

An untethered device configured to function in or proximal to a blood vessel or a lymph vessel may be used to detect specific biological targets based on ultrasound. As such, a cell or cells in the vessel circulation may pass through an examination zone either incorporated within the device or in close proximity to the device. The cell or cells in the examination zone are exposed to acoustic waves. The device measures the interactions of the acoustic waves with the cell or cells.

Acoustic imaging uses sound waves rather than light waves to generate an image. As such, a sound wave may be sent through a piece of quartz or glass coated with a thin layer of piezoelectric material that resonates at a specific frequency, for example, 1 GHz, and through a lens to scan a cell or cells (Ouellette (2004) The Industrial Physicist June/July: 14-17). The sound waves are reflected back up through the lens and piezoelectric material which serve as detector and amplifier. The reflected sound waves are recorded electronically and may be used directly to compare cellular profiles. Alternatively, the recorded sound waves may be converted into an image.

The resolution of acoustic imaging is dependent upon the frequency of sound used for imaging. As such, standard ultrasound imaging uses sound waves ranging in frequency from 3-10 MHz, but does not provide cellular detail. Higher frequency ultrasound in the range of 20-100 MHz may be used to detect changes in cellular structures in tissues and cells, although individual cells are still not easily resolved. For example, cells undergoing mitosis and cells undergoing apoptosis in response to a chemotherapeutic agent, for example, exhibit increased backscattered signal relative to normal cells (Baddour et al. (2002) Ultrasonics Symposium IEEE 2:1639-1644). Cellular resolution may be attained using sound waves ranging in frequency from 100 MHz to 2 GHz, comparable to the range used for acoustic microscopy, for example (Schenk et al. (1988) J. Histochem. Cytochem. 36:1341-1351). The latter corresponds to wavelengths of 15 to 0.75 microns in water, the medium through which ultrasound and acoustic imaging are done.

Photoacoustic imaging, in which ultrasound detection is combined with optical stimulation, may also be used to image objects (see, e.g. Wygant et al. (2005) IEEE Ultrasonics Symposium 1921-1924). In this process, the optical absorption properties of a material are imaged by detecting the ultrasound emitted when a cell is illuminated with a laser. The emitted ultrasound is due to the brief thermal expansions that occur when the laser energy is absorbed by the cell. Those regions that are more optically absorbent will generate a stronger acoustic signal. Laser pulse widths, for example, of 10 ns and wavelengths between 600 nm and 1000 nm may be used for photoacoustic imaging of cells. A single mechanically scanned piezoelectric transducer or a capacitive micromachined ultrasonic transducer array, for example, may be used to detect the laser generated ultrasound (see, e.g. Wygant et al. (2005) IEEE Ultrasonics Symposium 1921-1924).

Photoacoustic imaging may also be used to detect flowing cells in vivo (see, e.g. Zharov et al. (2006) SPIE Newsroom 10.1117/2.1200609.0391). As such, a cell or cells are irradiated with one or several focused laser beams operating at different wavelengths ranging, for example, from 415 to 2300 nm. An ultrasound transducer is used to record laser-induced acoustic waves.

Example 5

Detection of Biological Targets in Vessels Using Thermal Imaging

An untethered device configured to function in or proximal to a blood vessel or a lymph vessel may be used to detect specific biological targets based on thermal imaging. As such, a cell or cells in the circulation may pass through an examination zone either incorporated within the device or in close proximity to the device. Thermal energy or infrared radiation emitted from a cell or cells in the examination zone is detected by the device using infrared photosensors made of, for example, indium gallium arsenide or mercury cadmium telluride. The thermal information is captured by the device and either processed internally or sent wirelessly to an external processor. In real time, the captured information is compared with preset algorithms defining, for example, the thermal properties of normal blood cells and circulating tumor cells.

Infrared thermography may be used to characterize tissues and cells. For example, infrared thermography has been used to monitor mitochondrial heat production of human adipocytes and yeast in response to agents that either activate or inhibit cellular thermogenesis (see, e.g., U.S. Pat. No. 6,881,584). As such, infrared thermography may enable differentiation between normal and abnormal cells. For example, highly proliferative malignant tumor cells often have decreased mitochondria but higher metabolic activity due to compensatory increases in glycolytic ATP production in place of normal, more efficient oxidative phosphorylation (Gourley et al. (2005) Biomed. Microdevices 7:331-339). In contrast, benign or low grade malignant cells may have an increased number of mitochondria. Differences in mitochondrial number and function may be distinguishable using infrared thermography.

Example 6

Detection of Biological Targets in Vessels Using Photothermal Imaging

An untethered device configured to function in or proximal to a blood vessel or a lymph vessel may be used to detect specific biological targets based on photothermal imaging. As such, a cell or cells in the circulation may pass through an examination zone where they are illuminated by an electromagnetic energy source. The device measures the thermal response and related effects taking place directly in a cell or cells as a result of non-radiative relaxation of the absorbed electromagnetic energy in heat. The thermal information is captured by the device and either processed internally or sent wirelessly to an external processor. In real time, the captured information is compared with preset algorithms defining, for example, the photothermal properties of normal blood cells and circulating tumor cells.

Photothermal imaging may be used to distinguish between a white blood cell, a red blood cell, and a circulating tumor cell in vivo (see, e.g. Zharov et al. (2006) J. Cell. Biochem. 97:916-932). Basic informative parameters provided by photothermal spectroscopy include an absorption coefficient similar to those in conventional absorption spectroscopy, but several orders of magnitude more sensitive. Light absorbed into cells is measured directly through thermal phenomena.

A cell or cells may be irradiated, for example, with a short, focused pump laser pulse (415-2300 nm) leading to an increase in temperature of local cellular absorbing structures. The temperature distribution is transformed into a refraction distribution. Time-resolved monitoring of temperature-dependent variations in the cells refractive index is realized with thermolens or phase contrast imaging with a CCD camera and a second collinear laser pulse at 639 nm (Zharov et al. (2006) J. Cell. Biochem. 97:916-932).

As such, correlations between specific photothermal imaging parameters, such as cell shape, and photothermal response parameters, such as amplitude, shape and duration, and morphologic cell type may be used to differentiate between, for example, "rigid" red blood cells versus "flexible" red blood cells or circulating tumor cells versus normal white blood cells. As such, photothermal imaging may differentiate between flexible normal red blood cells and rigid *Plasmodium*-infected red blood cells. Red blood cells may be differentiated from white blood cells based on the amplitude of the integral photothermal responses, which are proportional to the cells' average absorption and differ ~30-40 fold for red blood cells and white blood cells (Zharov et al. (2006) J. Cell. Biochem. 97:916-932).

In addition, photothermal imaging is able to reveal the subcellular structures of a red blood cell versus a white blood cell based on specific distribution of chromophores (Galanzha et al. (2007) World J. Gastroenterol. 13:192-218). For example, hemoglobin associated with red blood cells has a smooth distribution whereas cytochromes or other absorbing biomolecules in white blood cells have a localized distribution.

Photothermal imaging associated with an untethered device may also be used to detect red blood cells that have been infected with the malaria parasite, *Plasmodium falciparum*. Red blood cells infected with *P. falciparum* accumulate light-absorbing hemozoin granules in the digestive vacuole of the parasite (Cowman et al. (1991) J. Cell. Biol. 113:1033-1042). Hemozoin is the chemically inert crystalline substance that is visible using standard light microscopy in stages that are actively degrading hemoglobin, such as trophozoites, schizonts and gametocytes. The monomeric, potentially toxic heme is released during proteolysis of red blood cell hemoglobin and, as the parasite is unable to cleave the porphyrin ring, it is 'detoxified' by conversion to the insoluble hemozoin polymer. As such, it is anticipated that the increased sensitivity of photothermal imaging over standard absorbance spectroscopy will enable differentiation of normal and malaria-infected red blood cells.

Example 7

Detection of Biological Targets Using Visible Light Absorption and Refraction

An untethered device configured to function in or proximal to a blood vessel or a lymph vessel may be used to detect specific biological targets based on visible light absorption. As such, a cell or cells in the circulation may pass through an examination zone where they are illuminated by visible light. The device captures the image of a cell or cells in the examination zone using a photosensor such as, for example, a CCD or CMOS camera. The image is captured by the device and either processed internally or sent wirelessly to an external processor. In real time, the captured information is compared with preset algorithms defining, for example, image and shape characteristics of normal circulating cells and abnormal or foreign cells.

Red blood cells infected with the malaria parasite may be detected using visible light and phase imaging (Cowman et al. (1991) J. Cell. Biol. 113:1033-1042). The parasite survives by digesting hemoglobin in the red blood cell and converts the toxic heme to hemozoin, the later of which forms brown crystalline structures that are readily detected by light microscopy. As such, a device emitting visible light may detect and distinguish infected red blood cells from normal red blood cells based on absorbance properties of the hemozoin. In addition, red blood cells in general may be detected based on light absorption and scattering using conventional bright field imaging under the conditions of flow using high speed data capture with a CCD or CMOS sensor (see, e.g., Zharov et al. (2006) J. Biomed. Opt. 11:054034-1-4; U.S. Pat. No. 5,934,278).

Trypanosomes may be distinguished from other components of the blood using visible light and phase imaging (Nolan et al. (1997) J. Biol. Chem. 272:29212-29221). The morphology of the protozoan is very distinct from that of normal blood cells. The protozoan is elongated, from 25 to 40 um in length with a flagellum while normal blood cells are predominantly spherical in shape. As such, the shape of a trypanosome as determined by visible light imaging can be readily distinguished from normal cells.

Similarly, cells may be imaged using quantitative phase contrast mapping which can reveal an objects surface with vertical resolution at the nanometer scale (Emery et al. (2007) J. Physics 61:1317-1321).

Cells may also be imaged using refractive index tomography (see, e.g. Choi et al. (2007) Nature Methods; advance online publication Aug. 12, 2007). In this instance, quantitative phase images from time-dependent interference patterns by the frequency shifting of a reference beam relative to the sample beam. A laser beam with a wavelength, for example, of 633 nm is divided into a sample and a reference path with a beamsplitter. A tilting mirror is used to vary the angle of illumination of the sample. The reference beam passes through a modulator shifting the frequency to a longer wavelength. When the reference beam and the sample beam are recombined, an interference pattern forms at the image plane. The interference pattern is captured with a CCD or CMOS sensor and the phase images are them calculated by applying phase-shifting interferometry.

Example 8

Detection of Biological Targets Using Autofluorescence

An untethered device configured to function in or proximal to a blood vessel or a lymph vessel may be used to detect specific biological targets based on autofluorescence. As such, a cell or cells in the vessel circulation may pass through an examination zone incorporated within part of the device or in close proximity to the device, such as the local bypass or reservoir described herein. The cell or cells are illuminated in the examination zone with a focused beam of light. The beam may be a form of electromagnetic energy such as, for example, white light, laser light, X-rays, or infrared radiation. The device detects cellular autofluorescence induced by the electromagnetic energy. The autofluorescence information may be captured by a photosensor such as, for example, a CCD (charge coupled device) and/or a CMOS (complementary metal oxide semiconductor) sensor. Disclosure of autofluorescence methods and related devices and systems is found in U.S. application Ser. Nos. 11/895,563, 11/895,564, 11/895,562, 11/895,565, 11/895,566, 11/895,567, 11/895,560, and 11/895,561.

A pathogen or pathogens may be detected in the vasculature via autofluorescence induced, for example, by electromagnetic energy. Naturally occurring autofluorescence in bacteria, for example, is derived from biomolecules containing fluorophores, such as porphyrins, amino acids tryptophan, tyrosine, and phenylalanine, and the coenzymes NADP, NADPH, and flavins (Koenig et al. (1994) J. Fluoresc. 4:17-40; Kim et al. (2004) IEEE/EMB Magazine January/February 122-129). The excitation maxima of these biomolecules lie in the range of 250-450 nm (spanning the ultraviolet/visible (UV/VIS) spectral range), whereas their emission maxima lie in the range of 280-540 (spanning the UV/VIS spectral range; Ammor (2007) J. Fluoresc. published on-line ahead of publication):

An untethered device may be used to detect pathogens associated with blood infections or septicemia, for example. Gram-negative enteric bacilli, *Staphylococcus aureus*, and *Streptococcus pneumoniae* are the most common pathogens in the United States associated with micronemia and sepsis. *Staphylococcus aureus* may be detected by autofluorescence using a device emitting electromagnetic energy at a wavelength, for example, of 488 nm (Hilton (1998) SPIE 3491:1174-1178). Optionally, *Staphylococcus aureus* may be distinguished from, for example, *Escherichia coli* and *Enterococcus faecalis* based on emission spectra induced by excitations at 410-430 nm (Giana et al. (2003) J. Fluoresc. 13:489-493; Ammor (2007) J. Fluoresc. published on-line ahead of publication). Similarly, *Streptococcus pneumoniae*, may be detected using fluorescence spectroscopy at excitation wavelengths of 250 and 550 nm and emission wavelengths of 265 and 700 nm (Ammor (2007) J. Fluoresc. published on-line ahead of publication).

A number of other bacteria may be identified based on autofluorescence. For example, bacteria associated with community acquired pneumonia, *Legionella anisa* and *Legionella dumoffli*, autofluoresce blue-white when exposed to longwave (365-nm) UV light (Thacker et al. (1990) J. Clin. Microbiol. 28:122-123). *Bacillus* spores will autofluoresce when excited by UV irradiation at a wavelength of 352 nm (Laflamme et al. (2006) J. Fluoresc. 16:733-737). *Clostridium sporogenes, Pseuodomonas aeruginose, Pseudomonas fluorescens, Kocuria rhizophila, Bacteroides vulgatis, Serratia marcescens*, and *Burkholderia cepacia* emit yellow-green fluorescent signal when illuminated with blue light (Sage et al. (2006) American Biotechnology Laboratory 24:20-23). *Enterococcus faecalis* and *Staphylococcus aureus* may be differentiated based on their respective autofluorescence in response to excitation spectra of 330-510 nm and emission spectra of 410-430 nm (Ammor (2007) J. Fluoresc. published on-line ahead of publication). *P. aeruginosa* may be detected by autofluorescence using a device emitting electromagnetic energy at a wavelength, for example, of 488 nm (Hilton (1998) SPIE 3491:1174-1178). *P. aeruginosa* contains a pigment called pyocyanin which appears blue in visible light and may also be used for detection.

Autofluorescence of endogenous porphyrins may also be used to detect bacteria. A number of bacteria produce protoporphyrins, including *Propinibacterium acnes, Bacillus thuringiensis, Staphylococcus aureus*, and some strains of *Clostridium, Bifidobacterium*, and *Actinomyces* (Koenig et al. (1994) J. Fluoresc. 4:17-40). Bacteria may also be detected using fluorescence lifetimes measured at 430, 487, and 514 nm after selective excitation at 340, 405, and 430 nm (Bouchard et al. (2006) J. Biomed. Opt. 11:014011, 1-7).

Autofluorescence may also be used to detect members of the fungi family. For example, *Candida albicans* irradiated with electromagnetic energy at wavelengths of 465-495 nm autofluoresces at an emission wavelength of 515-555 nm (Mateus et al. (2004) Antimicrob. Agents and Chemother. (2004) 48:3358-3336; Graham (1983) Am. J. Clin. Pathol. 79:231-234). Similarly, *Aspergillus niger* and *Aspergillus versicolor* may be detected using autofluorescence in response to excitation at 450-490 nm and emission at 560 nm (Sage et al. (2006) American Biotechnology Laboratory 24:20-23; Graham (1983) Am. J. Clin. Pathol. 79:231-234).

An untethered device may be used to detect and ablate parasites in the blood stream. For example, autofluorescence associated with the food vacuole of the malaria parasite *Plasmodium* spp. may be used to detect infected red blood cells with in the blood stream (Wissing et al. (2002) J. Biol. Chem. 277:37747-37755). As such, an untethered device may induce autofluorescence of parasites at a wavelength, for example, of 488 nm (Wissing et al. (2002) J. Biol. Chem. 277:37747-37755).

Example 9

Detection of Biological Targets Using Properties of Mitochondria

An untethered device configured to function in or proximal to a blood vessel or a lymph vessel may be used to detect specific biological targets based the properties of intracellular mitochondria.

A biocavity nanolaser may be used for optical phenotyping of human mitochondria (see, e.g. Gourley & Naviaux (2005) IEEE: J. Selected Topics in Quantum Electronics 11:818-

826). This method may be used to detect submicrometer particles by nanosqueezing light into photon modes imposed by the ultrasmall dimensions of the submicrometer laser cavity. As such, mitochondria from normal and abnormal cells may be differentiated.

For example, the mean diameter of a normal mitochondria ranges from 680 to 730 nm while diseased mitochondria from a cancer cell, for example, exhibit a larger mean diameter in the range of 750 to 830 nm. In addition, the mitochondria in the cancer cell have a very chaotic, unorganized and random distribution within the cytosol as compared with normal cells. As such, the lasing spectra of mitochondria may be used to differentiate between normal and abnormal cells flowing in the circulation (see, e.g. Gourley et al. (2005) Biomedical Microdevices 7:331-339).

Optionally, autofluorescence may be used to detect and image mitochondria (see, e.g., Sikder et al. (2005) Photochem. Photobiol. 81:1569-1571). Redox fluorometry may be used to measure the levels of pyridine nucleotides in the mitochondria, which may reflect differences in cellular metabolic state and activity. As such, autofluorescence associated with reduced pyridine nucleotides (nicotinamide adenine dinucleotide (NADH) and nicotinamide adenine dinucleotide phosphate (NADPH) may be measured in the region of 450 nm after excitation at 366 nm.

Example 10

Pattern and Cell Shape Recognition

The untethered device captures information regarding the properties of cells in a blood vessel or a lymph vessel. The information is either processed internally by the device or sent wirelessly to an external processor. The information processing results in identification of a cell as normal or abnormal, leading to a decision regarding the need for initiation of the ablation process.

Pattern recognition and cell shape algorithms may be used in the information processing. Various methods have been described for image and shape analysis of cells and subcellular components of cells (see, e.g., U.S. Pat. No. 5,107,422; U.S. Pat. No. 5,790,691; U.S. Pat. No. 6,956,961 B2; U.S. Pat. No. 7,151,847 B2; U.S. Patent Application 2005/0251347 A1; U.S. Patent Application 2006/0039593 A1; Fei-Fei et al. (2006) IEEE Transactions on Pattern analysis and Machine Intelligence 28:594-611; Martin et al. (2004) IEEE Transactions on Pattern analysis and Machine Intelligence 26:530-549; Olson et al. (1980) Proc. Natl. Acad. Sci. USA 77:1516-1520; Schneider, et al (1995) Biorheology 32:237-238).

Pattern recognition classifies patterns based on either prior knowledge or on statistical information extracted from the patterns. The patterns to be classified may be groups of measurements or observations, defining points in an appropriate multidimensional space. As such, a pattern recognition system may consist of a sensor that gathers information or observations to be classified or described; a feature extraction mechanism that computes numeric or symbolic information from the observations; and a classification or description scheme that does the actual work of classifying or describing the observations, based on extracted features. The classification or description scheme may be based on a set of patterns or a training set that have already been classified or described. The resulting learning strategy is characterized as supervised learning. Alternatively, the system may engage in unsupervised learning in that the system is not given prior labeling of patterns, but instead establishes the classes itself based on the statistical regularities of the patterns.

A Texture Analyzing System may be used to distinguish various cells in the vasculature based on the granularity of the cell or cells (Bins et al. (1981) Cytometry 1:321-324). As such, the imaged components of the cells are measured with a gray scale with 33 intervals ranging from black (level 0) to white (level 99) and a histogram is generated.

For example, mature WBC (neutrophils, eosinophils, basophils and lymphocytes) have a dense nuclear structure and therefore low counts. In contrast, monocytes have a looser, less dense nuclear structure and high counts. The cytoplasm of eosinophils and neutrophils is very granular and is reflected in the combination of high positive and low negative counts. Smaller values are seen in the cytoplasm of lymphocytes, monocytes and basophils. Similarly, granulometries may be used to identify red blood cells infected with the malarial parasite (Dempster & DiRuberto (2001) IEEE 5:V291-V294).

A neural network algorithm may be used to classify normal and abnormal components of the vasculature. For example, a neural network based fuzzy classifier may be used to automatically distinguish mature and immature white blood cells with a recognition rate of 90-92% (Uebele et al. (1995) IEEE Transactions on Systems, Man, and Cybernetics 25:353-361). In this instance, optically screened white blood cells may be classified into 12 categories of mature and immature white blood cells using features such as area and perimeter. A neural network based shape recognition algorithm using nuclear radius and curvature features may be also be used to automatically distinguish mature and immature white blood cells (He & Wilder (2002) IEEE: Proceedings of the Second Joint EMBS/BMES Conference, Houston, Tex., USA Oct. 23-26, 2002). Similar approaches may be used to classify and recognize lymphocytes, monocytes, neutrophils, eosinophils and basophils (see, e.g. Kovalev et al. (1996) IEEE: Proceedings of ICPR 1996 371-375). Alternatively, data regarding, for example, the infrared or light scattering properties of mature and immature cells may be the basis for the neural network based pattern recognition.

Subcellular phenotypes of a cell, for example, nuclei or mitochondria, may be automatically identified using different machine learning methods, including Support Vector Machines (SVMs), Artificial Neural Networks (ANN) or a combination of ANN and Bayesian learning (Conrad et al. (2004) Genome Res. 14:1130-1136). As such, image or spectral information regarding a subcellular component of a cell may be processed and used to distinguish various cell types.

Example 11

Methods for Capturing and Sequestering Biological Targets in Vessels

An untethered device configured to function in or proximal to a blood vessel or a lymph vessel may include the capacity to capture and sequester specific biological targets from the vasculature optionally into a reservoir (and/or local bypass) for future analysis. As such, the device may have the capacity to capture a biological target before analysis in the examination zone, at which point the biological target is identified as normal or abnormal and either released back into circulation or sequestered into a reservoir or holding chamber. Alternatively, the device may have the capacity to analyze the biological target as it passes through the examination zone, at which point the biological target is identified as normal or abnormal and either allowed to keeping moving or is captured and sequestered in a reservoir.

A specific cell or cells may be captured and moved into a reservoir (and/or local bypass) of the device using the natural fluid flow within the vessel. As such, the opening and closing of strategically placed valves within the device may be used to manipulate the flow of cells, allowing for selective sequestration of targeted cells into the reservoir.

Size exclusion may be used to detect and capture circulating tumor cells (see, e.g., Mohamed et al. (2004) IEEE Transactions on Nanobioscience, 3:251-256). As such, the device may have a fixed diameter or sieve, for example, through which normal blood components may pass but larger cells such as, for example, circulating tumor cells, are retained and either immediately ablated or shunted to a reservoir. Alternatively, the device may have a moveable aperture that allows for controlled changes in device diameter to capture and release or sequester a cell or cells as appropriate.

Alternatively, a cell or cells may be captured and sequestered based on intrinsic magnetic properties. For example, red blood cells infected with the malaria parasite *P. falciparum* may be captured based on the magnetic properties of the infected cells (Moore et al. (2006) FASEB J. 20:747-749). During development in the red blood cell, the malaria parasite digests hemoglobin leading to the accumulation of toxic heme. In the process of incorporating the heme into hemozoin crystals, the heme is converted to a high-spin ferriheme with increased magnetic properties. *P. falciparum* infected red blood cells may be enriched 40-fold relative to other blood components using a magnetic field intensity of 1.426 T (Zimmerman et al. (2006) Am. J. Trop. Med. Hyg. 74:568-572). As such, malaria-infected cells may be identified using the methods described here in and subsequently captured relative to other blood components, for example, using net volume magnetic susceptibility.

Optionally, a cell or cells may be captured and sequestered using suction. For example, cells along the surface of a lumen may be pulled away from the surface using a plunger system that sucks the cells into a suction chamber (see, e.g. U.S. Patent Application 2005/0272972 A1). As such, the device may include a plunger that when retracted causes a cell or cells to be sucked directly into a reservoir or into a tube (e.g. local bypass) that optionally leads to a reservoir.

Optionally, a form of optical trapping or optical tweezers may be used to move or sort a cell or cells into a reservoir. For example, red blood cells may be moved using a focused laser beam from, for example, a He—Ne laser (Grover et al. (2000) Optics Express 7:533-538). A focused laser exerts both a scattering force and a gradient force on a cell in its path and these forces can be manipulated to move an object. Optical tweezers may also be used to differentiate between normal and *Plasmodium*-infected red blood cells (Dharmadhikari et al. (2004) Optics Express 12:1179-1184).

Alternatively, dielectrophoresis may be used to move or sort a cell or cells in a microdevice (see, e.g. Chiou et al. (2005) Nature 436:370-372; Holmes & Morgan (2002) European Cells Materials 4:120-122). Dielectrophoresis (DEP) refers to the force on a cell in a non-uniform electrical field produced by an array of microelectrodes. Depending upon how negative and positive DEP forces are manipulated, a specific cell or cell type may be concentrated from a heterogeneous mix. Alternatively, different cell types may be sorted along the path of a device based on size and dielectric properties of the cellular membrane.

Example 12

Surveillance of Biological Targets in the Vasculature

An untethered device configured to function in or proximal to a blood vessel or a lymph vessel may be used over a period of time to monitor specific biological targets in the vasculature using the detection methods described herein. As such, a cell or cells in the vessel circulation may pass through an examination zone either incorporated within the device or in close proximity to the device. A cell or cells may be, for example, a bacterium, a platelet, a red blood cell, a white blood cell, a circulating tumor cell or a combination thereof. The cell or cells are analyzed in the examination zone using one or more of the methods described herein. The device captures information regarding the cell or cells and either processes the information internally or sends the information wirelessly to an external processor. The captured information is compared with preset algorithms defining, for example, the properties of a normal versus an abnormal or foreign cell. The device may keep track of or count the number of normal, abnormal and/or foreign cells, for example, over a period of time. Optionally, the device may monitor changes in cell morphology or chemistry over a period of time.

The untethered device may be used, for example, to monitor the relative numbers of normal biological components of blood or lymph vessels. Changes in the normal cell counts may be indicative of disease. For example, a normal white blood cell count ranges from 4,500 to 10,000 cells per microliter of blood. Leukopenia, a dangerously low white blood cell count below 2,500 cells per microliter, may be indicative of HIV or other viral infection, an autoimmune disorder such as lupus, or a bone marrow disease, such as leukemia or myelodysplastic syndromes (Mayo Clinic (2006) Low white blood cell count (leukopenia)).

As another example, the normal level of platelets in the blood ranges from 150,000 to 350,000 per microliter. As the platelet count decreases below a normal level, the ability of the body to prevent bleeding decreases. As such, tiny red dots may appear in the skin, bruising may occur more easily, the gums may bleed, and blood may appear in the stool or urine. When the platelet count falls to 10,000 to 5,000, life threatening bleeding in the digestive tract or brain may occur even when there is no injury (Merck Manual (1997) p. 755; Berkow et al, eds).

The surveillance information acquired by the untethered device may be used to monitor disease progression. For example, the device may be used in a patient or patients with cancer to monitor for the appearance of circulating tumor cells in the vasculature. Circulating tumor cells may be indicative of metastasis and may suggest a need for changes in the treatment regime. For example, the detection of circulating tumor cells in melanoma patients who are clinically "disease-free" indicates disease recurrence, tumor cell spreading, and a high potential for distant metastasis, and enables identification of high-risk melanoma patients (Hoon (2004) Nat. Clin. Pract. Oncol. 1:74-75).

The appearance of circulating tumor cells may also be indicative of long term prognosis for the patient. For example, breast cancer patients with levels of circulating tumor cells equal to or higher than 5 cells per 7.5 milliliters of blood have a shorter median progression-free survival (2.7 months vs. 7.0 months) and shorter overall survival (10.1 months versus greater than 18.0 months) as compared with breast cancer patients with less than 5 cells per 7.5 milliliters of blood (Cristofanilli et al. (2004) N. Engl. J. Med. 351:781-791).

The untethered device may also be used to monitor the effectiveness of a treatment regime. For example, the device may be used to monitor the titer of bacteria in the vasculature in response to antibiotic treatment. Similarly, the device may be used to monitor the white blood cell count of an HIV-AIDS patient in response to anti-viral treatments.

Alternatively, the device may be used to monitor side effects associated with a specific treatment regime. For example, treatment of HIV-AIDS with anti-viral nucleoside reverse transcriptase inhibitors (NRTIs) induces severe changes in lymphocyte mitochondrial morphology and function (Tolomeo et al. (2003) J. Clin. Pathol. 56:147-151). As such, the device may monitor lymphocyte mitochondria using the methods described herein to monitor the toxic effects of HIV treatment.

In another example, the device may monitor the effects of cancer therapy on normal blood components. Both chemotherapy and radiotherapy reduce white blood cell counts, making an individual more prone to infection. Similarly, red blood cell and platelet counts may be lowered in response to chemotherapy (Mayo Clinic (2005) Low blood cell counts: Side effect of cancer treatment). As such, the device may monitor the blood in real time and provide feedback to the physician and/or patient as to the blood cell counts, allowing for prompt treatment.

Example 13

Methods for at Least Partially Inactivating Biological Targets in Vessels

An untethered device configured to function in or proximal to a blood vessel or a lymph vessel may be used to at least partially inactivate a biological target in response to detection and recognition of the biological target as abnormal, for example. Alternatively, a second component downstream of the untethered device, for example, may be used to at least partially inactivate a biological target in the vessels and/or in a local bypass and/or reservoir. As such, once the abnormal cell has been detected and recognized by the untethered device, the untethered device may nearly simultaneously initiate an inactivation process while the cell is still effectively in the examination zone. Alternatively, once the abnormal cell has been detected and recognized by the untethered device, a downstream component may be signaled to initiate inactivation at a future time consistent with passage of the abnormal cell in proximity to the downstream component based, for example, on the measured flow rate within the vessel. In some instances, focused energy sufficient to at least partially inactivate an abnormal cell may be directed only at the cell of interest. Alternatively, a segment of the vessel lumen containing at least the abnormal cell may be targeted.

An untethered device configured to function in or proximal to a blood vessel or lymph vessel may use ultraviolet radiation to at least partially inactivate a biological target. For example, many pathogens are inactivated or killed by UV germicidal irradiation (Anderson et al. (2000) IEEE Transactions on Plasma Science 28:83-88; Hancock et al. (2004) IEEE Transactions on Plasma Science 32:2026-2031). UV light ranges from UVA (400-315 nm), also called long wave or 'blacklight'; UVB (315-280 nm), also called medium wave; and UVC (<280 nm), also called short wave or 'germicidal'." *Escherichia coli* may be partially or completely inactivated, for example, by exposure to a UV electromagnetic energy source at wavelengths of 100-280 nm (Anderson et al. (2000) IEEE Transactions on Plasma Science 28:83-88). Alternatively, *Escherichia coli* as well as *Salmonella enteritidis*, for example, may be inactivated using pulsed broad-spectrum electromagnetic energy with high UV content from, for example, a Xenon lamp (Anderson et al. (2000) IEEE Transactions on Plasma Science 28:83-88). In this instance, targeted bacteria are subjected to 100-1000 pulses of broad-spectrum light with each pulse lasting, for example, 85 ns and having, for example, a power output of 10 MW. Viruses may be inactivated using UV irradiation (Tseng & Li, (2007) J. Occup. Envirn. Hyg. 4:400-405). Fungi, such as *Aspergillus flavus* and *Aspergillus fumigatus*, may also be inactivated using UV germicidal irradiation at, for example, 12-98 mJ/cm$^2$ (Green et al. (2004) Can. J. Microbiol. 50:221-224).

Optionally, the device may emit electromagnetic energy at a wavelength or wavelengths within the visible spectrum to at least partially inactivate a biological target. For example, *Staphylococcus aureus* and *Pseudomonas aeruginosa* may be inactivated using a wavelength of 405 nm at doses ranging, for example, from 1-20 J/cm$^2$ (Guffey et al. (2006) Photomed. Laser Surg. 24:680-683). *Pseudomonas aeruginosa* as well as *Escherichia coli* may be partially inactivated using, for example, a wavelength of 630 nm at 1-20 J/cm$^2$ (Nussbaum et al. (2002) J. Clin. Laser Med. Surg. 20:325-333). Similarly, a number of oral bacteria, including *Acinobacillus actinomycetemcomitans, Fusobacterium nucleatum, Porphromonas gingivalis, Pnevotella intermedia,* and *Streptococcus sanguis,* may be partially inactivated using a diode 665 laser at 100 mW at energy densities ranging from 10 J/cm$^2$ to 22 J/cm$^2$ (Chan et al. (2003) Lasers Surg. Med. 18:51-55). Alternatively, a pathogen, for example *Escherichia coli*, may be at least partially inactivated or killed using a 810 nm diode laser with doses ranging from 130-260 J/cm$^2$ (Jawhara et al. (2006) Lasers Med. Sci. 21:153-159).

Similarly, visible light may be used to at least partially inactivate a virus. For example, a virus may be at least partially inactivated using a very low power laser emitting 80 femtosecond pulses at a wavelength of 425 nm and frequency of 80 MHz (Tsen et al. (2007) Virol. J. Vol. 4, published on line ahead of publication; Tsen et al. (2007) J. Physics: Condensed Matter Vol. 19, published on line ahead of publication). Under these conditions, the viruses are inactivated through impulsive stimulated Raman scattering, which induces vibrations within the microorganism sufficient to disrupt normal function.

Alternatively, energy may be used that disrupts the function of heme iron porphyrins associated with iron uptake and utilization, inactivating iron dependent bacteria such as *Escherichia coli* and *Salmonella* (U.S. Pat. No. 6,030,653). Pathogens may be inactivated by irradiating the surface with visible and near infrared light having wavelengths of approximately 465 nm, 600 nm, and 950 μm, respectively.

Optionally, visible light energy emitted from an untethered device may be combined, for example, with systemic administration of a photosensitive agent (Maisch (2007) Lasers Med. Sci. 22:83-91; Jori et al. (2006) Lasers Surg. Med. 38:468-481). For example, *Staphylococcus aureus* and *Pseudomonas aeruginosa* may be inactivated using either a 0.95-mW helium-neon laser (632 nm) or a 5-mW indium-gallium-aluminum-phosphate laser (670 nm) with exposure doses ranging from 0.1 to 10.0 J/cm$^2$ in combination with the bacterial sensitizing agent, toluidine blue 0 (DeSimone et al. (1999) Phys. Ther. 79:839-846). Similarly, inactivation of bacteria by a diode 665 laser may be enhanced, for example, by prestaining the bacteria with methylene blue (Chan et al. (2003) Lasers Surg. Med. 18:51-55). Alternatively, a fluorescing dye, for example, indocyanine green (ICG) may be used in combination with a diode laser with an emission wavelength, for example, of 808 nm, to inactive a pathogen or pathogens (Bartels et al. (1995) SPIE 2395:602-606). Optionally, a polycationic photosensitizer conjugated between, for example, poly-L-lysine and chlorin$_{e6}$, may be administered and subsequently irradiated with a diode laser at 665 nm at doses ranging from, for example, 40-160 J/cm$^2$ to kill bacteria (Hamblin et al. (2002) Photochem. Photobiol. 75:51-57). Optionally, pathogens in the vasculature, such as, for example, *Staphylococcus aureus* and *Staphylococcus epidermidis*, may be at least partially inactivated using energy from, for example, an argon-ion pumped dye laser (wavelength of 630 nm with total light dose of 180 J/cm2) in combination with 5-aminolevulinic acid or Photofrin (Karrer et al. (1999) Lasers Med. Sci. 14:54-61; Nitzan et al. (1999) Lasers Med. Sci. 14:269-277).

An untethered device configured to function in or proximal to a blood vessel or lymph vessel may use laser-induced thermal energy to at least partially inactivate a biological target. For example, lasers are commonly used to treat cancers, such as basal cell skin cancer and the very early stages of some cancers, such as cervical, penile, vaginal, vulvar, and non-small cell lung cancer (National Cancer Institute (2004) Laser in Cancer Treatment FactSheet). As such, circulating tumor cells, for example, may be at least partially inactivated by laser-induced thermal energy.

A variety of lasers with varied excitation wavelengths and penetration potential may be used to generate electromagnetic energy sufficient to at least partially inactivate, for example, a circulating tumor cell or cells (Burr et al. (2004) Interventional Technologies for Tissue Volume Reduction, October 2004). For example, circulating tumor cell or cells may be ablated using a carbon dioxide ($CO_2$) laser (10,600 nm, 0.1-0.2 mm penetration depth). Melanoma and cervical cancer cells may be ablated with a $CO_2$ laser using a power output ranging, for example, from 40 W to 80 W (Gibson, et al (2004) Br. J. Surg. 91:893-895; Bekassy et al. (1997) Lasers. Surg. Med. 20:461-466). Alternatively, cancer cells may be ablated by a Yttrium-Aluminium-Garnet (YAG) laser with Neodymium (Nd, 1064 nm or 1320 nm, 3-4 mm penetration depth), Erbium (Eb, 2940 nm, with <0.1 mm penetration depth), or Holmium (Ho, 2070 nm). For example, colorectal adenoma cells and lung cancer cells may be ablated using an Nd:YAG (1064 nm) with maximal power output of 100 W (Norberto et al. (2005) Surg. Endosc. 19:1045-1048; Hansen et al. (2006) Minim. Invasive Ther. Allied Technol. 15:4-8). Alternatively, cancer cells may be ablated by diode lasers (600-1600 nm), argon laser (488 nm and 514 nm, 1-1.5 mm penetration depth), or an excimer laser (180-350 nm, cell/tissue disintegration). As such, the untethered device may contain one or more of the lasers described herein as an optical energy source for use in at least partially inactivating a biological target such as, for example, a circulating tumor cells.

Alternatively, a circulating tumor cells or cells, for example, may be ablated by electromagnetic energy emitted from a laser in combination with a photosensitizing agent in a process termed photodynamic therapy (PDT; National Cancer Institute (2004) Laser in Cancer Treatment FactSheet). For example, a patient may be injected with a photosensitizing agent such as, for example, Photofrin or 5-aminolevulinic acid, which after a few days concentrates in the cancerous cells. Electromagnetic energy from, for example, a laser is then used to activate the photosensitizing agent which has a subsequent toxic effect on the cancer cell or cells and results in cell death.

Laser-induced thermal energy generated by a $CO_2$ or Nd:YAG laser may also be used to at least partially inactivate a pathogen in the vasculature (see, e.g. Bartels et al. (1995) SPIE 2395:602-606). *Escherichia coli* 0157:H7, for example, is extremely sensitive to heat with a maximum tolerance of approximately 35 degrees centigrade (U.S. Pat. No. 6,030, 653). *Staphylococcus aureus* may be partially inactivated or killed using high-power Nd:YAG laser radiation between 50 and 300 W with laser pulse frequencies of 5 to 30 Hz and pulse energies from 2 to 30 J, resulting in a range of energy densities from 800 to 270 J/cm$^2$ (Yeo et al. (1998) Pure Appl. Opt. 7:643-655). Similarly, *Staphylococcus epidermidis*, may be killed using pulsed radiation from a Nd:YAG laser with an exposure of 1000-2000 J/cm$^2$ (Gronqvist et al. (2000) Lasers Surg. Med. 27:336-340).

The untethered device may use electromagnetic energy in the form of x-rays to at least partially inactivate biological targets in the vasculature. As such, the device may contain a miniature X-ray emitter, such as that described in U.S. Patent Application 2004/0218724 A1. Alternatively, the device may contain radioisotopes such as cobalt 60, cesium 137, or europium 152, for example, that emit strong gamma rays and may be used to ablate cancerous cells. Optionally, the device may contain other intrinsically radioactive isotope such as those that might be used for brachytherapy, including, for example, iodine 125, iodine 131, strontium 89, phosphorous, palladium, or phosphate (National Cancer Institute (2004) Radiation Therapy for Cancer FactSheet).

X-ray therapy or radiotherapy is routinely used to treat almost every type of solid tumor, including cancers of the brain, breast, cervix, larynx, lung, pancreas, prostate, skin, spine, stomach, uterus, or soft tissue sarcomas (National Cancer Institute (2004) Radiation Therapy for Cancer FactSheet). For example, breast cancer cells may be ablated using a miniature electron beam-driven x-ray source at doses of 5 to 20 Gy (Ross et al. (2005) Breast Cancer Res. 7:110-112). As such, radiotherapy may be used to at least partially inactivate circulating tumor cells derived from, for example, these solid tumors.

Pathogens may also be at least partially inactivated by x-ray electromagnetic energy. For example, pathogens such as *Escherichia coli* 0157:H7, *Salmonella*, and *Campylobacter jejuni* may be at least partially inactivated or killed using cobalt-60 gamma radiation at doses of 0.5 to 3 kGy (Clavero et al. (1994) Applied Environ. Microbiol. 60:2069-2075).

Alternatively, particle beam energy may be used to at least partially inactivate a biological target. For example, *Salmonella*, *Yersinia*, and *Campylobacter* may be at least partially inactivated using accelerated electrons with doses of irradiation ranging from 1-3 kGy (Sarjeant et al. (2005) Poult. Sci. 84:955-958). Similarly, *Bacillus* endospores may be at least partially inactivated using electron beam irradiation with doses ranging from 5 to 40 kGy (Helfinstine et al. (2005) Applied Environ. Microbiol. 71:7029-7032).

Alternatively, a cancer cell or cells may be ablated by using particle beam energy using a type of linear accelerator. Medical LINAC (linear accelerator-based external beam radiotherapy), for example, accelerates electrons to kinetic energies from 4 to 25 MeV using microwave radiofrequency waves at $10^3$ to $10^4$ MHz (Podgorsak Chapter 5). A LINAC may provide X-rays in the low megavoltage range (4 to 6 MV). Alternatively, a LINAC may provide both X-rays and electrons at various megavoltage energies, for example, two photon energies (6 and 18 MV) and several electron energies (6, 9, 12, 16, and 22 MeV; Podgorsak Chapter 5).

The untethered device may use electromagnetic energy in the form microwave or radiofrequency waves to at least partially inactivate biological targets in the vessels. The microwave range includes ultra-high frequency (UHF) (0.3-3

GHz), super high frequency (SHF) (3-30 GHz), and extremely high frequency (EHF) (30-300 GHz) signals. Microwave radiation at a frequency of 29.8 GHz (Ka-band), for example, may be used to at selectively kill bacteria with minimal damage to healthy human cells (Ardnt et al. Microwave radiation—Therapeutic application for cure of subcutaneous bacterial infections. Space Life Sciences).

The untethered device may alternatively use the heating properties of focused ultrasound to at least partially inactivate biological targets in the vasculature. Ultrasound causes tissue damage through conversion of mechanical energy into heat and through cavitation. Above a threshold of 56 degrees centigrade, for example, rapid thermal toxicity is achieved and cells are irreversibly inactivated or killed. High-intensity focused ultrasound (HIFU) uses short exposures of focused ultrasound that rapidly increases cellular temperature above 80 degrees centigrade and is used for ablation, for example, of hepatocellular carcinoma, prostate carcinoma, bladder and kidney cancers (see, e.g., Kennedy et al. (2003) Br. J. Radiology 76:590-599). As such, it is anticipated that short exposures to high-intensity focused ultrasound may be used to at least partially ablate targeted cells within the vessels.

Optionally, an untethered device may emit a laser-generated stress wave sufficient to disrupt a biological target. For example, stress waves sufficient to disrupt cell membranes may be generated with an ArF (193 nm) or a KrF (248 nm) eximer laser. Peripheral blood mononuclear cells and red blood cells may be damaged using, for example, 5 pulses of pressure ranging from 700 to 1000 bar (Lee et al. (1999) IEEE Journal of Selected Topics in Quantum Electronics 5:997-1003). As such, the device may use a laser to generate a stress wave sufficient to at least partially ablate a targeted cell.

An untethered device may emit electrical energy in a focused area in the vasculature sufficient to ablate a biological target. For example, cancer cells in suspension may be at least partially ablated using electrical pulses sufficient to induce irreversible electroporation of the cells (Miller et al. (2005) Technol. Cancer Res. Treat. 4:699-705). As such, a cell or cells may be exposed, for example, to 10-30, 0.3 millisecond pulses at 500 to 2500 V/cm to induce at least partial inactivation.

Examples 14

Devices for Detection and Ablation of Biological Targets in Vessels

Figure 11:
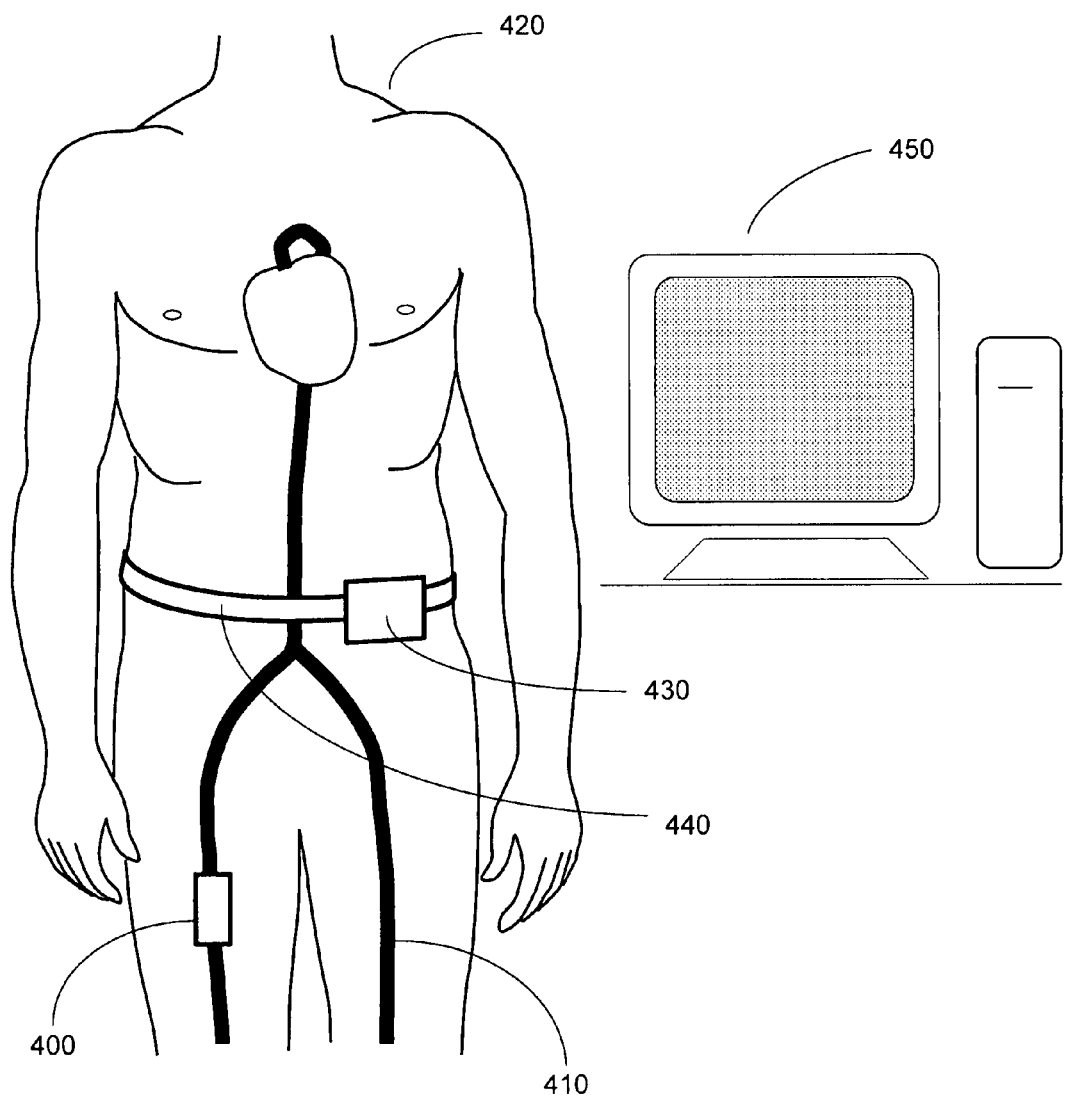
FIG. 11 shows a schematic of an illustrative embodiment of a system including a device in use on a subject.

An untethered device configured to function in or proximal to a blood vessel or a lymph vessel may be used to detect, register and at least partially inactivate a biological target. FIG. 11 shows an illustrative diagram of a system including a device 400. The device 400 is placed in or proximal to a vessel 410 of a patient 420. The device 400 may work autonomously, containing all of the components necessary to detect, register and/or inactive a biological target. Alternatively, the device 400 may be linked wirelessly to a remote (optionally portable), processor and/or power supply 430 and/or external computer processor 450 and/or power supply.

In one configuration, the processor and/or power supply 430 is worn externally by the patient 420 on, for example, a belt 440. Optionally, the processor and/or power supply 430 may be held by the patient 420 in, for example, a pocket, a backpack or a purse. Alternatively, the processor and/or power supply 430 may be surgically implanted in the patient 420 (see, e.g., U.S. Pat. No. 6,409,719). Optionally, the processor and/or power supply 430 may be linked to the device 400 via a wire or wires.

FIG. 12, FIG. 13, FIG. 14, and FIG. 15 show illustrative configurations of systems including one or more untethered devices configured to function in the lumen of a blood vessel or lymph vessel to detect, register and optionally at least partially inactivate a biological target.

FIG. 12A shows an illustrative configuration of an untethered device 460 for the detection and at least partial inactivation of a biological target in the lumen of a vessel 410. In this configuration, the untethered device 460 may be a hollow cylinder that when placed in a lumen of a vessel 410 allows for the flow of fluid and cells 500 and 510 through the central core 470 of the cylinder. The cylinder may be reversibly positioned in the vessel using inflatable pouches 480. Alternatively, the cylinder may be positioned in the vessel using one or more retractable hooks or barbs, for example, that latch on to the lumen of the vessel 410. The hollow cylinder contains a detection and/or ablation unit 490, which optionally contains one or more of a power source, control circuitry, one or more energy sources, one or more sensors and a processor. Control of the device may be completely self-contained or at least partially controlled wirelessly by an external user.

As normal cells 500 and abnormal cells 510 pass through the central core 470 of the untethered device 460, the detection and/or ablation unit 490 emits a first energy beam, such as, for example, an electromagnetic or acoustic energy which interacts with the cell in a characteristic manner. In this context, abnormal cells 510 may be, for example, pathogens, pathological cells or cancerous cells as described herein. The detection and ablation unit 490 processes the information regarding the interaction of the normal cell 500 and abnormal cell 510 with a first energy beam and analyzes whether the cell is normal or abnormal and almost simultaneously emits a second energy beam sufficient to at least partially inactivate the abnormal cell 510.

As illustrated in FIG. 12B, the system may include a second untethered device 465 positioned downstream from the first device 460. As such, the first device 460 emits an energy beam from the detection and/or ablation unit 490 to analyze a passing biological target, and determines whether the biological target is normal or abnormal. The first device 460 may send a signal to the second device 465 to initiate emission of an energy beam from a second detection and/or ablation unit 495 sufficient to at least partially inactivate a biological target at a time in the future consistent with the passage of an abnormal target through the second device 465.

FIG. 13 shows an illustrative configuration of a system including an untethered device 460 with the capability of controlling fluid and cell flow in the lumen of a vessel 410 for the detection and optionally at least partial inactivation of a biological target. In this configuration, the device 460 is a hollow tube with an exit aperture 520 that may be opened or closed to control the flow of fluid and cells in the vessel. As such, the exit aperture 520 of the device 460 may be in an open position 525 allowing for free flow of fluid and cells, as shown in FIG. 13A. Cells pass through the device 460 unabated and are monitored and optionally destroyed by the detection and/or ablation unit 490. Alternatively, as shown in FIG. 13B, the exit aperture 520 may periodically shift to the closed position 530 providing more time, for example, for the analysis of cells in the device 460 and/or opportunity for targeted inactivation. The device may automatically open and close the exit aperture 520 at a fixed rate. Alternatively, the exit aperture 520 may open and close depending upon signals sent from the detection and/or ablation unit 490 in response to detecting an abnormal cell, for example. Optionally, opening and closing of the exit aperture 520 may be dictated externally by the patient, physician, or other medical practitioner.

Figure 14:
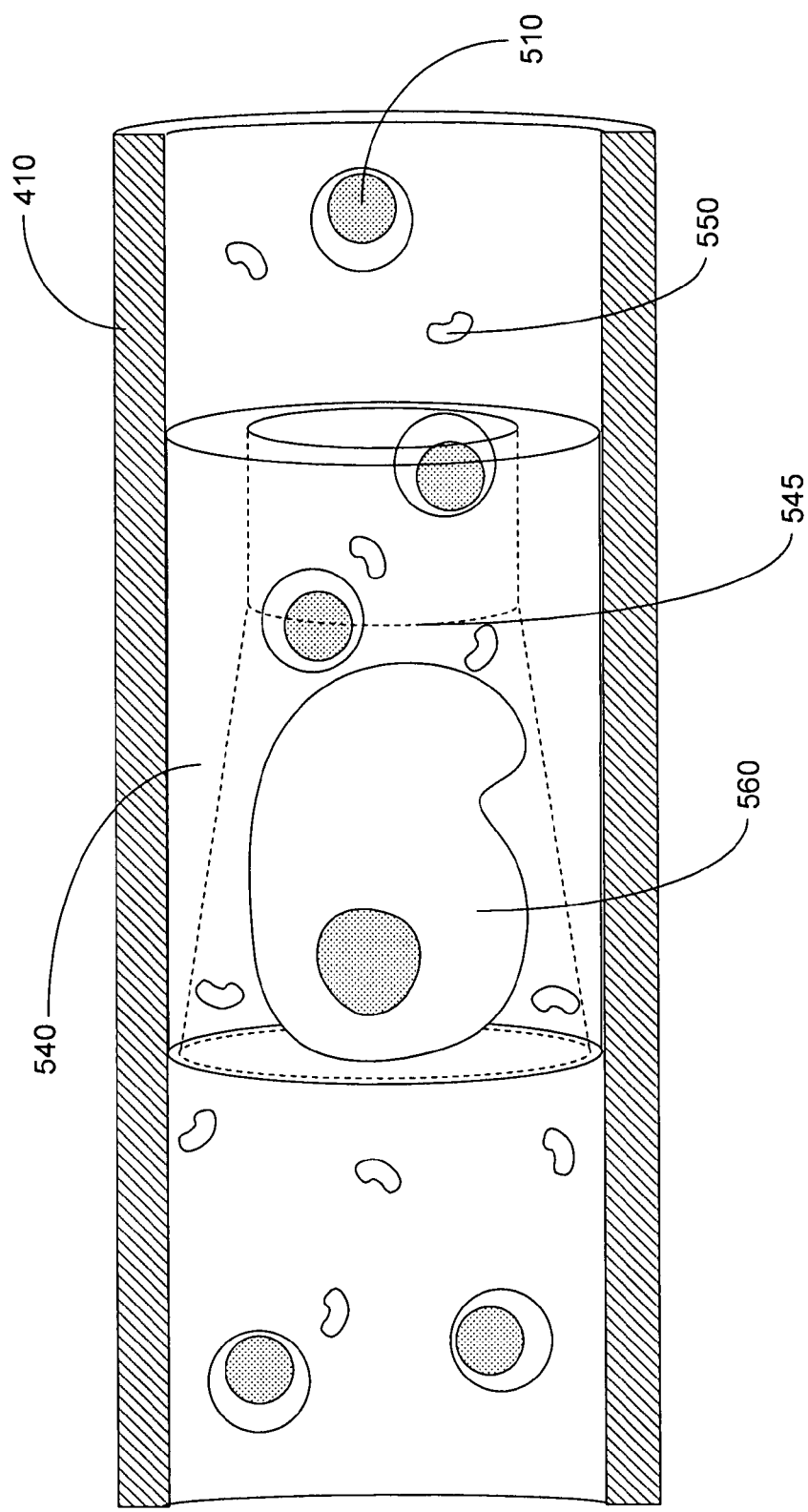

FIG. 14 shows an illustrative configuration of an untethered device 540 with the capability of temporarily trapping and at least partially inactivating abnormally large biological targets in the lumen of a vessel 410. In this configuration, size exclusion may be used to trap an abnormally large cell 560 such as, for example, a circulating tumor cell. As such, cells pass through the hollow tube of the device 540. Within the device 540 is a choke point 545 which narrows the diameter of the hollow tube. As such, smaller cells 510 and 550, such as, for example, red and white blood cells, may pass through the device whereas an abnormally large cell 560 will slowed down or become trapped, at which point the cell is bombarded with an energy beam sufficient to at least partially inactivate the target.

FIG. 15A and FIG. 15B show alternative illustrative configurations of systems including an untethered device for the detection and at least partial inactivation of a biological target in the lumen of a vessel 410.

FIG. 15A shows an illustrative configuration of an untethered device 570 in the lumen of a vessel 410 in which the main body of the device is a hollow tube configured using a diamond-patterned mesh structure similar to, for example, a stent (see, e.g. Lally et al. (2005) J. Biomechanics 38:1574-1581; U.S. Patent Application 2006/0074479 A1). In this configuration, one or more detection and/or ablation units 575 are distributed around the hollow tube. Each detection and/or ablation unit 575 may have the capability of emitting energy, sensing a response, inducing ablation, or a combination thereof. Optionally, the system may include an exterior (to the vessel lumen) unit 580 which may provide processing and/or power capabilities. The exterior unit 580 may be attached to the outer surface of the vessel with one or more hooks or barbs 585, for example.

FIG. 15B shows an illustrative configuration of system including an untethered device 590 in the lumen of a vessel 410 in which the main body of the device is a hollow tube configured from one or more parallel rings 595. Alternatively the hollow tube may be formed from a spiral, for example, of a single or multiple pieces of material. As shown, each ring 595 of the device 590 may include an energy emitting unit 600 and a sensing unit 610. Alternatively, units 600 and 610 may have both energy emitting and sensing capabilities. In this configuration, the device may have an ablating unit 620 downstream from the energy emitting units 600 and the sensing units 610. As such, a cell may pass through the hollow tube where the energy emitting unit 600 and the sensing unit 610 register the cell as normal or abnormal. If the cell is abnormal a signal is sent to the ablating unit 620 to initiate cell inactivation at a time in the future consistent with the time needed for a cell to move from one end of the tube to the other. The device 590 may be used in conjunction with an exterior unit 630 which optionally surrounds the exterior of the vessel 410 like a sleeve and provides, for example, additional processing and/or power capabilities.

FIG. 16 and FIG. 17 show illustrative configurations of systems including one or more untethered devices configured as units to function alone or together in the lumen of a blood vessel or lymph vessel to detect, register and optionally at least partially inactivate a biological target.

FIG. 16A shows an illustrative configuration of a device 640 which is attached to the interior surface of a vessel 410 by virtue of a hook or barb 650. The untethered device 640 may be configured to act autonomous or be controlled by an external user. The untethered device 640 may monitor the flow of fluid and normal cells 500 and abnormal cells 510. The device 640 detects abnormal cells 510 based on the characteristic response of normal cells 500 and abnormal cells 510 to a beam of energy 660. On detection of one or more abnormal cells, the device 640 emits a second beam of energy 660 sufficient to at least partially ablate the detected abnormal cell 510 before the cell exits the inactivation area.

In an alternative illustrative configuration of the system, an energy emitting unit 670 may be paired with a sensing unit 680, as shown in FIG. 16B. In this configuration, the energy emitting unit 670 and sensing unit 680 are each attached to the interior surface of a vessel 410 by virtue of one or more hook or barb 650. The energy emitting unit 670 emits a beam of energy 660 which irradiates, for example, an abnormal cell 510. The sensing unit 680 measures the response of the abnormal cell 510 to the beam of energy 660 and sends a signal back to the energy emitting unit 670 to initiate cell inactivation, whereupon the energy emitting unit 670 emits a second beam of energy 660 sufficient to at least partially inactivate a biological target.

Alternatively, one or more illustrative system may include an energy emitting and sensing unit 690 paired with a downstream ablating unit 700 as shown in FIG. 16C. The energy emitting and sensing unit 690 and the ablating unit 700 are optionally attached to the interior surface of a vessel 410 by virtue of one or more hook or barb 650. An abnormal cell 510 is irradiated by a beam of energy 660 emitted from the energy emitting and sensing unit 690 and registered as abnormal. A signal is sent to the ablating unit 700 to initiate cell inactivation at a time in the future consistent with the time needed for a cell to move from the energy emitting and sensing unit 690 to the ablating unit 700. The ablating unit 700 emits a second energy beam 710 sufficient to at least partially inactivate a biological target.

FIG. 17A shows an illustrative configuration of a system including three separate units; an energy emitting unit 720, a sensing unit 680, and a downstream ablating unit 700, all of which are attached to the interior surface of a vessel 410 by virtue of one or more hook or barb 650. In this configuration, an abnormal cell 510, for example, is irradiated by an energy beam 660 from an energy emitting unit 720. The response of the abnormal cell 510 to the energy beam 660 is detected by the sensing unit 680 which may relay information to the ablating unit 700 as to whether cell inactivation should be initiated. The ablating unit 700 emits an energy beam 710 at a time in the future consistent with the time needed for a cell to move from the sensing unit 680 to the ablating unit 700. The energy emitting unit 720, the sensing unit 680, and the downstream ablating unit 700 may be used in conjunction with an exterior unit 630 which optionally surrounds the exterior of the vessel 410 like a sleeve and provides, for example, processing and/or power capabilities.

FIG. 17B shows an alternative illustrative configuration of a system in which an energy emitting and sensing unit 690 is paired with a downstream ablating unit 730. In this configuration, the ablating unit 730 is a hollow tube positioned within a vessel 410 using inflatable pouches 480, for example. The ablating unit 730 has an aperture 740 which may be closed to trap biological targets identified for inactivation, and/or for additional sensing optionally prior to inactivation, for example. An abnormal cell 510, for example, is identified by the energy emitting and sensing unit 690 as abnormal and a signal is sent to the ablating unit 730. The downstream ablating unit 730 initiates closure of the aperture 740 at a time in the future consistent with the time needed for the abnormal cell 510 to reach the ablating unit 730. Once the abnormal cell 510 is trapped, the ablating unit 730 emits an energy beam 710 sufficient to at least partially inactive a biological target.

FIG. 18, FIG. 19, and FIG. 20 show illustrative configurations of systems configured to function proximal to a blood vessel or lymph vessel to detect, register and optionally at least partially inactivate a biological target. In these examples, the system may incorporate device including a sleeve which at least partially encircles a vessel.

FIG. 18A shows an illustrative configuration of a device 750 which at least partially encircles the exterior of a vessel 410 (see, e.g., U.S. Pat. No. 6,106,477). FIG. 18B shows an illustrative configuration of optional components of the device 750. A hinge 760 may be used to open the device 750 to enable it to at least partially encircle a vessel 410. The device may have an energy emitting unit 780 coupled with a sensing unit 770 which scans cells through the wall of a vessel 410. Methods have been described for imaging cells in vivo from the exterior of a vessel (see, e.g., Galanzha et al. (2007) World. J. Gastroenterol. 13:192-218; U.S. Pat. No. 7,264,794 B2). The device 750 may also contain a processing and/or power supply unit 790.

FIG. 19 shows various illustrative configurations of one or more systems including a device configured to function proximal to a blood vessel or lymph vessel. In these examples, a sleeve 810 constructed from a mesh-like, breathable, biocompatible material is used to encircle the exterior of a vessel 410 (see, e.g., U.S. Patent Application 2006/0149348 A1). Various components are optionally attached to this sleeve. In FIG. 19A, a device 800 consists of a sleeve 810 that is attached along a seam 820 to itself and/or the vessel 410 using a reversible wet/dry adhesive such as that derived from gecko and mussel (e.g. geckel), for example (see, e.g., Lee et al. (2007) Nature 448:338-342). Alternatively, a magnetic strip or Velcro-like material may be used to close the sleeve. Attached to the sleeve 810 is an energy emitting unit 830 and a sensing unit 840. Alternatively, a single unit capable of energy emitting and sensing may be attached to the sleeve 810.

In FIG. 19B, a device 801 may have a sleeve 810 attached to itself and/or to the vessel 410 using, for example, sutures 850 (optionally staples and/or another kind of medical closure known to those of skill in the art). In this configuration, a constrictor (e.g. compression) band 860 is positioned downstream from the sleeve 810. The constrictor band 860 may be used to restrict the flow of fluid and cells through the vessel 410 optionally for brief periods of time. The constrictor band 860 may be an inflatable tube that upon inflation closes down the diameter of the vessel 410. Alternatively, the constrictor band 860 may constitute a band of biocompatible material that may be controllably tightened and loosened, optionally using one or more ratchets, for example.

The constrictor band 860 may be activated by inputs from a wire 870 connected, for example, to the sensing unit 840. Alternatively, the constrictor band 860 may be activated by a wireless signal form the sensing unit 840, and/or from one or more external sources. The constrictor band 860 may be used to slow down cells to facilitate analysis by the energy emitting unit 830 and the sensing unit 840. Alternatively, the constrictor band 860 may be activated after an abnormal cell has been identified to trap the cell prior to inactivation from an energy beam emitted, for example, from the energy emitting unit 830.

In FIG. 19C, a device 802 is configured with a first sleeve 810 and a second sleeve 890 which is positioned downstream of the first. Attached to the second sleeve 890 is an ablating unit 900 that is optionally attached by a wire 870 to the sensing unit 840. In this configuration, the sleeve 810 is attached to itself and/or the vessel 410 using a closure device 880. A closure device may include, for example, a snap, a hook, or Velcro-like material. A cell or cells in the vessel 410 are analyzed, for example, by the energy emitting unit 830 and the sensing unit 840. When an abnormal cell is registered by the sensing unit 840, a signal is sent to the downstream ablating unit 900 by a wire 870. Alternatively, a wireless signal may be sent to activate the ablating unit 900. The ablating unit 900 emits an energy beam sufficient to at least partially inactivate a biological target at a time in the future consistent with the passage of the cell into the target zone of the ablating unit 900.

FIG. 20 shows various illustrative configurations of systems including a device configured to function proximal to a blood vessel or lymph vessel and optionally to sequester a biological target into a reservoir, for example, for future analysis. In FIG. 20A, a device 803 is configured with a sleeve 810 constructed from a breathable, biocompatible material. The sleeve 810 is used to encircle the exterior of a vessel 410. An expandable reservoir 930, for example, a sack constructed from biocompatible material, is attached to the sleeve 810 by a tube-like structure 920. The tube 920 opens into the vessel 410 through an adjustable valve 910. In this configuration, a constrictor band 860 may be positioned downstream of the sleeve 810 to restrict the flow of fluid and cells for brief periods of time. A cell in the vessel 410 is analyzed by the energy emitting unit 830 and the sensing unit 840. If a cell or cells is identified that should be sequestered, a signal is sent to the constrictor band 860 via a wire 870, for example. The constrictor band 860 closes down the diameter of the vessel 410, trapping cells in the vicinity of the valve 910. The valve 910 is triggered to open, allowing a cell or cells to flow into the tube 920 and into the reservoir 930. The movement of cells into the reservoir 930 may be passive, optionally driven by the flow pressure of the vessel 410.

FIG. 20B shows an alternative configuration in which device 804 includes a reservoir 940 located in a remote position relative to the vessel 410. For example, the remote reservoir 940, made from silicon or other biocompatible material, may be positioned on or near the surface of the skin, for example, allowing for easy access by a physician, veterinarian, or other medical practitioner using a syringe, for example (see, e.g. Diegelmann et al. (1987) J. Leukocyte Biol. 42:667-672). The remote reservoir 940 is attached to the sleeve 810 through a tube 920 that traverses the length between the position of the sleeve 810 on a vessel 410 and the position of the reservoir 940. As such, a cell or cells is analyzed by an energy emitting unit 830 and a sensing unit 840. If a cell or cells is identified that should be sequestered, a wireless signal is sent to the constrictor band 860. The constrictor band 860 closes down the diameter of the vessel 410, trapping cells in the vicinity of a valve 910. The valve 910 is triggered to open, allowing a cell or cells to flow into the tube 920 and down its length to the reservoir 940. The movement of cells into the remote reservoir 940 may be passive, optionally driven by the flow pressure of the vessel 410. Alternatively, a type of peristaltic motion, for example, may be used along the length of the tube 920 to move cells into the remote reservoir 940.

FIG. 21, FIG. 22, FIG. 23, and FIG. 24 show illustrative configurations of systems including a device configured to function proximal to a blood vessel or lymph vessel to detect, register and optionally at least partially inactivate a biological target. In these examples, the device may incorporate a shunt (e.g. local bypass), allowing for analysis of all or part of the cells flowing through a vessel 410.

FIG. 21 shows an illustrative configuration of a device 805 in which a sleeve 810 is combined with a shunt 960. FIG. 21A shows an exterior view of the device 805 encircling a vessel 410. The sleeve 810 is reversibly attached to itself and/or the vessel 410 along the seam 820 using the methods described herein. The shunt 960 may have sharp, optionally scalpel-like and/or large-bore needle-like ends 970 that pierce the vessel 410 as the sleeve 810 is closed around the vessel 410. In this manner, openings are created in the wall of the vessel 410 allowing for passage of some or all of the vessel contents into the shunt 960. Attached to the shunt may be an energy emitting unit 980 and a sensing unit 990. The shunt 960 itself may be made of clear, optically compatible material, allowing for unobstructed imaging of a cell or cells from the outside surface of the shunt 960. Alternatively, a portion of the energy emitting unit 980 and/or the sensing unit 990 may be incorporated into the inner surface of the shunt.

FIG. 21B shows an illustrative configuration of the interior view of a device 805 in which a sleeve 810 is combined with a shunt 960. As such, a subset of cells in vessel 410 may enter the shunt 960 through an opening 1000 generated by piercing the surface of the vessel 410 optionally as described in FIG. 21A and/or known in the art. An abnormal cell 510, for example, may be targeted with an energy beam 660 emitted from the energy emitting unit 980. The cellular response is detected by the sensing unit 990. The sensing unit 990 sends a signal to the energy emitting unit 980 to activate a second energy beam 660 configured to at least partially inactivate the abnormal cell 510. Untargeted cells pass through the shunt 960 and back into the flow of vessel 410.

FIG. 22A and FIG. 22B show illustrative configurations of systems showing the interior view of devices 950 and 955 configured with a shunt 960 (e.g. local bypass) to analyze all or a subset of cells in a vessel 410. In FIG. 22A, a device 950 includes a shunt 960 attached to a vessel 410 and contains an energy emitting unit 980 and a sensing unit 990. Access to and from the vessel 410 to the shunt 960 is controlled by valves 1005 at either end of the shunt 960. As such, when the valve 1005 is opened, a cell or cells may pass into the shunt 960. The cell, for example an abnormal cell 510, may pass through an examination zone 965 within the shunt 960.

Within the examination zone, the abnormal cell 510 is irradiated, for example, with electromagnetic energy from a laser unit 1010. The laser unit 1010 may be comprised of one or more quantum dot lasers or nanolasers, for example (see, e.g., PHYSORG (2007) news 95617101; Nozaki et al. (2007) Optics Express 15:7506-7514). Alternatively, acoustic energy may be emitted from laser unit 1010. A specific sensing device 1020, such as, for example, a CCD or CMOS sensor, captures information regarding the interaction of the abnormal cell 510 with the electromagnetic energy emitted by a laser unit 1010. Methods have been described, for example, for the scaling of CMOS sensor technology down to the nanometer scale (Chang et al. (2003) Proceedings of the IEEE 91:1860-1873). The shunt 960 may also contain a processor and/or power unit 1030. Alternatively, the shunt 960 may be connected wirelessly or by wire to a remote or external processor and/or power supply.

Once the abnormal cell 510 has been identified as abnormal, a signal is optionally sent to initiate cell inactivation. As such, the laser unit 1010 may emit a second energy beam sufficient to at least partially inactivate the abnormal cell 510. Optionally a second energy emitting unit 1040 may be used to emit energy sufficient to at least partially inactivate the abnormal cell 510.

In FIG. 22B, a device 955 includes a shunt 960 configured to allow for sequestering of specific biological targets into a reservoir. The shunt 960 is attached to a vessel 410 and contains an energy emitting unit 980 and a sensing unit 990. Access to and from the vessel 410 to the shunt 960 is controlled by valves 1005 at either end of the shunt 960. As such, when the valve 1005 is opened, a cell or cells may pass into the shunt 960. Additional valves 1005 may be placed at either end of the examination zone 965. The cell, for example an abnormal cell 510, may pass through an examination zone 965 within the shunt 960. The abnormal cell 510 is analyzed by the laser unit 1010 and the sensing unit 1020 as described in FIG. 22A.

The abnormal cell 510 may be targeted for sequestration. As such an additional valve 1005 may open into tube 1070 connected to a reservoir. The reservoir may be proximal or remote relative to the analysis device as described herein. The cell or cells may passively move into the tube 1070 based on flow pressure. Alternatively, a cell or cell may be specifically moved into the tube 1070 by a force 1060 emitted from a force unit 1050. The force may be part of an optical trap, a DEP trap or magnetic in nature, as described herein. Once the appropriate cell or cells have been sequestered, the valve 1005 associated with the tube 1070 may be closed and other valves 1005 downstream opened to allow untargeted cells in the shunt 960 to rejoin the flow in vessel 410.

FIG. 23 and FIG. 24 show illustrative configurations of systems including an artificial vessel shunt which is secured between the ends of a vessel 410. FIG. 23A shows an exterior view of this configuration in which the artificial vessel shunt 1080 is attached to the free ends of a vessel 410 by a connector 1090, such as, for example, a cinch. Alternatively, the artificial vessel shunt 1080 may be attached to the vessel 410, for example, by a tight fitting with the lumen of the vessel 410 and barbs on the end of the artificial vessel shunt 1080 (see, e.g. U.S. Pat. No. 7,175,637). The artificial vessel shunt 1080 has an energy emitting unit 980 and a sensing unit 990 associated with it.

FIG. 23B shows an illustrative configuration of the interior of an artificial vessel shunt 1080 attached to both ends of vessel 410 using connectors 1090. The artificial vessel shunt 1080 may have one or more valves 1005 to control the flow of fluid and cells. Within the examination zone, an abnormal cell 510 as referenced in FIG. 22 is irradiated, for example, with electromagnetic energy from a laser unit 1010. A specific sensing device 1020 captures information regarding the interaction of the abnormal cell 510 with the electromagnetic energy emitted by a laser unit 1010. Once the abnormal cell 510 has been identified as abnormal, a signal is sent to initiate cell inactivation. As such, the laser unit 1010 may emit a second energy beam sufficient to at least partially inactivate the abnormal cell 510. Optionally a second energy emitting unit 1040 may be used to emit energy sufficient to at least partially inactivate the abnormal cell 510. Optionally, the abnormal cell is targeted for sequestration and is moved through a valve 1005 into a tube 1070 for removal to a reservoir.

FIG. 24A and FIG. 24B show alternative configurations of systems including an artificial vessel in which all or a subset of the cells in the vessel flow are analyzed. For example, in FIG. 24A, a device 1100 is inserted between the two ends of a vessel 410 using connectors 1090. Associated with the device is a shunt 960. A cell or cells passing through the shunt may be analyzed by an energy emitting unit 980 and a sensing unit 990. If appropriate, a cell may be at least partially inactivated within the shunt 960. FIG. 24B shows an illustrative configuration of a device 1110 which is similar to that of device 1100 with the addition of a tube 1070 which allows for sequestration of targeted cells to a reservoir 940.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

For ease of reading, all values described herein, and all numerical ranges described herein are approximate and should be read as including the word "about" or "approximately" prior to each numeral, unless context indicates otherwise. For example, the range "0.0001 to 0.01" is meant to read as "about 0.0001 to about 0.01."

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references herein, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
    locally capturing image information associated with a lumen of a local bypass, the local bypass associated with one or more blood vessel or lymph vessel in a subject;
    analyzing the image information to at least partially identify a plurality of targets exhibiting a disease or disorder during an expected transit time of the plurality of targets through a detection area; and
    locally collecting the plurality of identified targets in one or more reservoirs having a plurality of different compartments; and
    segregating the plurality of identified targets into the plurality of different compartments at least partially based on the disease or disorder.

2. The method of claim 1, wherein segregating the plurality of identified targets into the plurality of different compartments at least partially based on the disease or disorder includes segregating one or more cancer cell types into one or more of the plurality of different compartments.

3. The method of claim 1, wherein segregating the plurality of identified targets into the plurality of different compartments at least partially based on the disease or disorder includes segregating one or more infectious agent types into one or more of the plurality of different compartments.

4. The method of claim 1, wherein segregating the plurality of identified targets into the plurality of different compartments at least partially based on the disease or disorder includes segregating cancer cells into one or more of the plurality of different compartments and segregating infectious agents into another one or more of the plurality of different compartments.

5. A system comprising:
    one or more reservoirs responsive to control circuitry, and configured to receive one or more targets and to function in one or more blood vessel or lymph vessel of a subject;
    one or more energy source located in the one or more reservoirs, and configured to provide energy to elicit one or more image responses associated with the one or more targets;
    one or more sensors configured to function in, or proximal to, the one or more reservoirs, and to capture the one or more image responses, wherein the one or more sensors are configured to orient to the one or more energy source; and
    control circuitry coupled to the one or more sensors, and responsive to at least partially identify the one or more targets during an expected transit time of the one or more targets through a detection area in, or proximal to, the one or more reservoirs at least partially based on the captured one or more image responses.

6. The system of claim 5 wherein the one or more sensors are located in the one or more reservoirs.

7. The system of claim 5, wherein the one or more energy source is further configured to provide ablation energy to the one or more targets responsive to the control circuitry at least partially identifying the one or more targets.

8. A system comprising:
    one or more reservoirs responsive to control circuitry, and configured to receive one or more targets and to function in, or proximal to, a local bypass, the local bypass configured to function in, or proximal to, one or more blood vessel or lymph vessel of a subject;
    one or more first energy source configured to function in, or proximal to, the one or more reservoirs, and to provide energy configured to elicit one or more image responses associated with the one or more targets;
    one or more sensors configured to function in, or proximal to, the one or more reservoirs, and to capture the one or more image responses, wherein the one or more sensors are configured to orient to the one or more first energy source;
    control circuitry coupled to the one or more sensors, and responsive to at least partially identify the one or more targets during an expected transit time of the one or more targets through a detection area in, or proximal to, the one or more reservoirs at least partially based on the captured one or more image responses; and
    one or more inserts responsive to the control circuitry, and configured to modulate a diameter of a lumen of the one or more reservoirs.

9. The system of claim 8, further comprising:
    one or more second energy source responsive to control circuitry, and configured to provide ablation energy to a target area during the expected transit time of the one or more targets through the target area.

10. The system of claim 8, wherein the one or more inserts are configured to modulate an inner and/or outer diameter of the lumen of the one or more reservoirs.

11. The system of claim 8, wherein the control circuitry is configured to modulate the diameter of the lumen of the one or more reservoirs at selected time intervals.

* * * * *